United States Patent
Lee et al.

(10) Patent No.: US 9,617,328 B2
(45) Date of Patent: *Apr. 11, 2017

(54) FUSION PROTEIN HAVING FACTOR IX ACTIVITY

(75) Inventors: Min Sun Lee, Yongin-si (KR); Hun-Taek Kim, Seoul (KR); Bong-yong Lee, Seoul (KR); Mahn Hoon Park, Yongin-si (KR); Yun Jung Lim, Seoul (KR)

(73) Assignee: SK CHEMICALS CO., LTD., Seongnam-si (KR)

( * ) Notice: Subject to any disclaimer, the term of this patent is extended or adjusted under 35 U.S.C. 154(b) by 443 days.

This patent is subject to a terminal disclaimer.

(21) Appl. No.: 13/880,239

(22) PCT Filed: Oct. 19, 2011

(86) PCT No.: PCT/KR2011/007795
§ 371 (c)(1),
(2), (4) Date: Jul. 29, 2013

(87) PCT Pub. No.: WO2012/053823
PCT Pub. Date: Apr. 26, 2012

(65) Prior Publication Data
US 2013/0296534 A1 Nov. 7, 2013

(30) Foreign Application Priority Data
Oct. 20, 2010 (KR) ........................ 10-2010-0102572

(51) Int. Cl.
*C07K 14/745* (2006.01)
*C07K 14/79* (2006.01)

(52) U.S. Cl.
CPC ............ *C07K 14/79* (2013.01); *C07K 14/745* (2013.01); *C07K 2319/00* (2013.01)

(58) Field of Classification Search
CPC .............................. C07K 14/79; C07K 14/745
See application file for complete search history.

(56) References Cited

U.S. PATENT DOCUMENTS

| | | | | |
|---|---|---|---|---|
| 5,403,484 A | * | 4/1995 | Ladner | C07K 1/047 435/235.1 |
| 8,129,504 B2 | | 3/2012 | Prior et al. | |
| 2004/0023334 A1 | * | 2/2004 | Prior | 435/69.7 |
| 2005/0147618 A1 | * | 7/2005 | Rivera et al. | 424/178.1 |

FOREIGN PATENT DOCUMENTS

| | | |
|---|---|---|
| CN | 101177456 A | 5/2008 |
| JP | 2008232916 A | 10/2008 |
| WO | 03062276 A2 | 7/2003 |
| WO | 2005003165 A2 | 1/2005 |
| WO | 2007112005 A2 | 10/2007 |

OTHER PUBLICATIONS

European Patent Office Communication dated Nov. 3, 2014, issued in counterpart Application No. 11834623.8.
State Intellectual Property Office of People's Republic of China, Communication dated May 22, 2014, issued in corresponding Chinese application No. 201180050731.1.
Stefan Schmidt, "Fusion-proteins as biopharmaceuticals—applications and challenges," PubMed—NCBI, Curr Opin Drug Discov Devel, Mar. 12, 2009, pp. 1-2, AstraZeneca R&D, Sodertalje, SE-15185 Sodertalje, Sweden.
Robert T. Peters, et al., "Prolonged activity of factor IX as a monomeric Fc fusion protein", Blood Journal, The American Society of Hematology, Mar. 11, 2010, pp. 2057-2064, vol. 115, No. 10.
David A. Roth, et al., "Human recombinant factor IX: safety and efficacy studies in hemophilia B patients previously treated with plasma-derived factor IX concentrates", Blood Journal, The American Society of Hematology, Dec. 15, 2001, pp. 3600-3606, vol. 98, No. 13.
Byung-Joon Kim, et al., "Transferrin Fusion Technology: A Novel Approach to Prolonging Biological Half-Life of Insulinotropic Peptides", The Journal of Pharmacology and Experimental Therapeutics, May 21, 2010, pp. 682-692, vol. 334, No. 3.
European Patent Office, Communication dated Mar. 24, 2016, issued in counterpart European application No. 11834623.8.
Chang et al., "Design, Engineering, and Production of Human Recombinant T Cell Receptor Ligands Derived from Human Leukocyte Antigen DR2," Journal of Biological Chemistry, American Society for Biochemistry and Molecular Biology, US, vol. 276 (26); pp. 24170-24176, Jun. 29, 2001, 7 pages in total.
Jang et al., "Ex Vivo Analysis of Thymic CD4 T Cells in Nonobese Diabetic Mice with Tetramers Generated from I-Ag7/Class II-Associated Invariant Chain Peptide Precursors," Journal of Immunology, vol. 171; pp. 4175-4186 (2003), 13 pages in total.
Chinese Patent Office, Communication dated Sep. 18, 2016 mailed in Chinese Patent Application No. 201180050731.1.
Han et al., Journal of Hebei Medical University, 28(3); pp. 224-227, 2007, with English abstract.

* cited by examiner

Primary Examiner — Marsha Tsay
(74) Attorney, Agent, or Firm — Sughrue Mion, PLLC

(57) ABSTRACT

Disclosed is a fusion protein comprising blood coagulation factor IX (FIX) and transferrin. The fusion protein exhibits improved specific FIX activity, as compared to native FIX, and can be useful in the treatment of FIX deficiency-associated diseases.

6 Claims, 12 Drawing Sheets

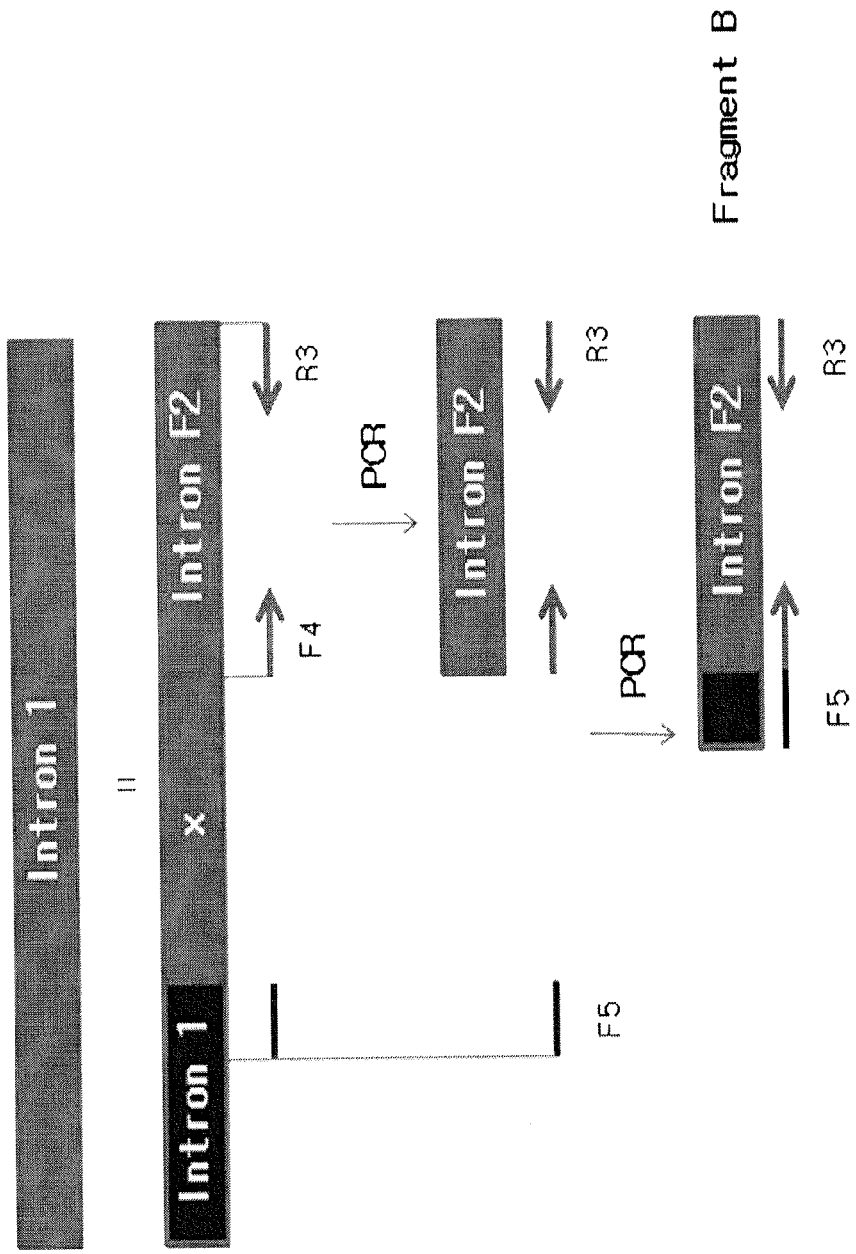

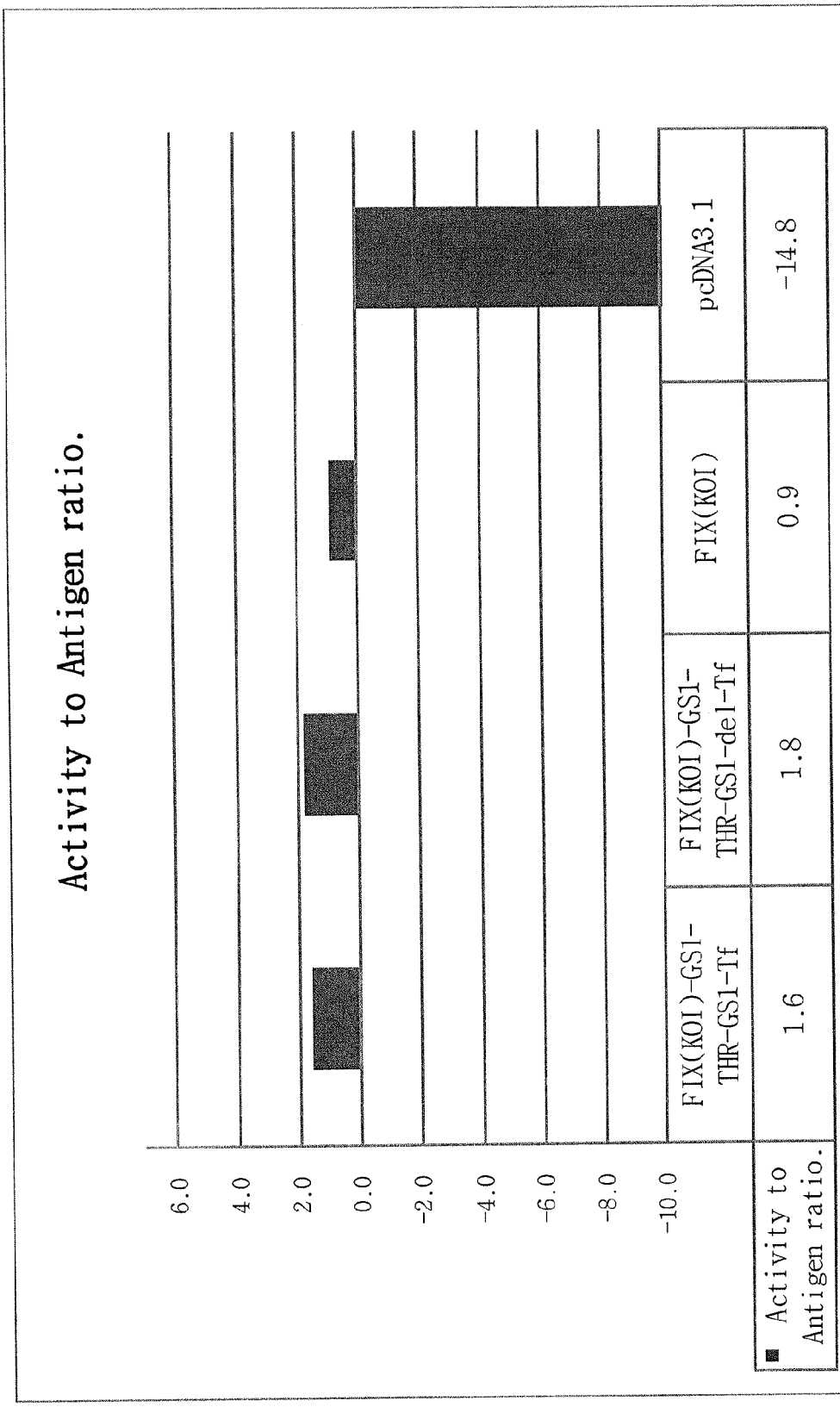

SEQUENCE LISTING

<160> NUMBER OF SEQ ID NOS: 64

<210> SEQ ID NO 1
<211> LENGTH: 461
<212> TYPE: PRT
<213> ORGANISM: Homo sapiens

<400> SEQUENCE: 1

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

```
Leu Gln Tyr Leu Arg Val Pro Leu Val Asp Arg Ala Thr Cys Leu Arg
    370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
            420                 425                 430
Glu Glu Cys Ala Met Lys Gly Lys Tyr Gly Ile Tyr Thr Lys Val Ser
        435                 440                 445
Arg Tyr Val Asn Trp Ile Lys Glu Lys Thr Lys Leu Thr
    450                 455                 460

<210> SEQ ID NO 2
<211> LENGTH: 679
<212> TYPE: PRT
<213> ORGANISM: Homo sapiens

<400> SEQUENCE: 2

Val Pro Asp Lys Thr Val Arg Trp Cys Ala Val Ser Glu His Glu Ala
1               5                   10                  15
Thr Lys Cys Gln Ser Phe Arg Asp His Met Lys Ser Val Ile Pro Ser
                20                  25                  30
Asp Gly Pro Ser Val Ala Cys Val Lys Lys Ala Ser Tyr Leu Asp Cys
            35                  40                  45
Ile Arg Ala Ile Ala Ala Asn Glu Ala Asp Ala Val Thr Leu Asp Ala
        50                  55                  60
Gly Leu Val Tyr Asp Ala Tyr Leu Ala Pro Asn Asn Leu Lys Pro Val
65                  70                  75                  80
Val Ala Glu Phe Tyr Gly Ser Lys Glu Asp Pro Gln Thr Phe Tyr Tyr
                85                  90                  95
Ala Val Ala Val Val Lys Lys Asp Ser Gly Phe Gln Met Asn Gln Leu
            100                 105                 110
Arg Gly Lys Lys Ser Cys His Thr Gly Leu Gly Arg Ser Ala Gly Trp
        115                 120                 125
Asn Ile Pro Ile Gly Leu Leu Tyr Cys Asp Leu Pro Glu Pro Arg Lys
    130                 135                 140
Pro Leu Glu Lys Ala Val Ala Asn Phe Phe Ser Gly Ser Cys Ala Pro
145                 150                 155                 160
Cys Ala Asp Gly Thr Asp Phe Pro Gln Leu Cys Gln Leu Cys Pro Gly
                165                 170                 175
Cys Gly Cys Ser Thr Leu Asn Gln Tyr Phe Gly Tyr Ser Gly Ala Phe
            180                 185                 190
Lys Cys Leu Lys Asp Gly Ala Gly Asp Val Ala Phe Val Lys His Ser
        195                 200                 205
Thr Ile Phe Glu Asn Leu Ala Asn Lys Ala Asp Arg Asp Gln Tyr Glu
    210                 215                 220
Leu Leu Cys Leu Asp Asn Thr Arg Lys Pro Val Asp Glu Tyr Lys Asp
225                 230                 235                 240
Cys His Leu Ala Gln Val Pro Ser His Thr Val Val Ala Arg Ser Met
                245                 250                 255
Gly Gly Lys Glu Asp Leu Ile Trp Glu Leu Leu Asn Gln Ala Gln Glu
            260                 265                 270
His Phe Gly Lys Asp Lys Ser Lys Glu Phe Gln Leu Phe Ser Ser Pro
        275                 280                 285
```

His Gly Lys Asp Leu Leu Phe Lys Asp Ser Ala His Gly Phe Leu Lys
    290                 295                 300
Val Pro Pro Arg Met Asp Ala Lys Met Tyr Leu Gly Tyr Glu Tyr Val
305                 310                 315                 320
Thr Ala Ile Arg Asn Leu Arg Glu Gly Thr Cys Pro Glu Ala Pro Thr
                325                 330                 335
Asp Glu Cys Lys Pro Val Lys Trp Cys Ala Leu Ser His His Glu Arg
            340                 345                 350
Leu Lys Cys Asp Glu Trp Ser Val Asn Ser Val Gly Lys Ile Glu Cys
        355                 360                 365
Val Ser Ala Glu Thr Thr Glu Asp Cys Ile Ala Lys Ile Met Asn Gly
370                 375                 380
Glu Ala Asp Ala Met Ser Leu Asp Gly Gly Phe Val Tyr Ile Ala Gly
385                 390                 395                 400
Lys Cys Gly Leu Val Pro Val Leu Ala Glu Asn Tyr Asn Lys Ser Asp
                405                 410                 415
Asn Cys Glu Asp Thr Pro Glu Ala Gly Tyr Phe Ala Val Ala Val Val
            420                 425                 430
Lys Lys Ser Ala Ser Asp Leu Thr Trp Asp Asn Leu Lys Gly Lys Lys
        435                 440                 445
Ser Cys His Thr Ala Val Gly Arg Thr Ala Gly Trp Asn Ile Pro Met
    450                 455                 460
Gly Leu Leu Tyr Asn Lys Ile Asn His Cys Arg Phe Asp Glu Phe Phe
465                 470                 475                 480
Ser Glu Gly Cys Ala Pro Gly Ser Lys Lys Asp Ser Ser Leu Cys Lys
                485                 490                 495
Leu Cys Met Gly Ser Gly Leu Asn Leu Cys Glu Pro Asn Asn Lys Glu
            500                 505                 510
Gly Tyr Tyr Gly Tyr Thr Gly Ala Phe Arg Cys Leu Val Glu Lys Gly
        515                 520                 525
Asp Val Ala Phe Val Lys His Gln Thr Val Pro Gln Asn Thr Gly Gly
    530                 535                 540
Lys Asn Pro Asp Pro Trp Ala Lys Asn Leu Asn Glu Lys Asp Tyr Glu
545                 550                 555                 560
Leu Leu Cys Leu Asp Gly Thr Arg Lys Pro Val Glu Glu Tyr Ala Asn
                565                 570                 575
Cys His Leu Ala Arg Ala Pro Asn His Ala Val Val Thr Arg Lys Asp
            580                 585                 590
Lys Glu Ala Cys Val His Lys Ile Leu Arg Gln Gln His Leu Phe
        595                 600                 605
Gly Ser Asn Val Thr Asp Cys Ser Gly Asn Phe Cys Leu Phe Arg Ser
    610                 615                 620
Glu Thr Lys Asp Leu Leu Phe Arg Asp Asp Thr Val Cys Leu Ala Lys
625                 630                 635                 640
Leu His Asp Arg Asn Thr Tyr Glu Lys Tyr Leu Gly Glu Glu Tyr Val
                645                 650                 655
Lys Ala Val Gly Asn Leu Arg Lys Cys Ser Thr Ser Ser Leu Leu Glu
            660                 665                 670
Ala Cys Thr Phe Arg Arg Pro
        675

<210> SEQ ID NO 3
<211> LENGTH: 5

-continued

```
<212> TYPE: PRT
<213> ORGANISM: Artificial Sequence
<220> FEATURE:
<223> OTHER INFORMATION: GS1 linker

<400> SEQUENCE: 3

Gly Gly Gly Gly Ser
 1               5

<210> SEQ ID NO 4
<211> LENGTH: 77
<212> TYPE: PRT
<213> ORGANISM: Artificial Sequence
<220> FEATURE:
<223> OTHER INFORMATION: GS15 linker

<400> SEQUENCE: 4

Gly Gly Gly Gly Ser Gly Gly Gly Gly Ser Gly Gly Gly Gly Ser Gly
 1               5                  10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser Gly Gly Gly Gly Ser Gly Gly Gly Gly Ser Gly Gly Gly Gly
        50                  55                  60

Ser Gly Gly Gly Gly Ser Gly Gly Gly Gly Ser Tyr Gly
 65                  70                  75

<210> SEQ ID NO 5
<211> LENGTH: 17
<212> TYPE: PRT
<213> ORGANISM: Artificial Sequence
<220> FEATURE:
<223> OTHER INFORMATION: GS1-THR-GS1 linker

<400> SEQUENCE: 5

Gly Gly Gly Gly Ser Leu Val Pro Arg Gly Ser Gly Gly Gly Ser Tyr
 1               5                  10                  15

Gly

<210> SEQ ID NO 6
<211> LENGTH: 78
<212> TYPE: PRT
<213> ORGANISM: Artificial Sequence
<220> FEATURE:
<223> OTHER INFORMATION: GS7-THR-GS7 linker

<400> SEQUENCE: 6

Gly Gly Gly Gly Ser Gly Gly Gly Gly Ser Gly Gly Gly Gly Ser Gly
 1               5                  10                  15

Gly Gly Gly Ser Gly Gly Gly Gly Ser Gly Gly Gly Gly Ser Gly Gly
                20                  25                  30

Gly Gly Ser Leu Val Pro Arg Gly Ser Gly Gly Gly Ser Gly Gly Gly
            35                  40                  45

Gly Gly Ser Gly Gly Gly Gly Ser Gly Gly Gly Gly Ser Gly Gly Gly
        50                  55                  60

Gly Ser Gly Gly Gly Gly Ser Gly Gly Gly Gly Ser Tyr Gly
 65                  70                  75

<210> SEQ ID NO 7
<211> LENGTH: 15
<212> TYPE: PRT
```

```
<213> ORGANISM: Artificial Sequence
<220> FEATURE:
<223> OTHER INFORMATION: GS1-THR-GS1-del linker

<400> SEQUENCE: 7

Gly Gly Gly Gly Ser Leu Val Pro Arg Gly Ser Gly Gly Gly Ser
 1               5                  10                  15

<210> SEQ ID NO 8
<211> LENGTH: 9
<212> TYPE: PRT
<213> ORGANISM: Artificial Sequence
<220> FEATURE:
<223> OTHER INFORMATION: GS1-FXa linker

<400> SEQUENCE: 8

Gly Gly Gly Gly Ser Ile Glu Gly Arg
 1               5

<210> SEQ ID NO 9
<211> LENGTH: 76
<212> TYPE: PRT
<213> ORGANISM: Artificial Sequence
<220> FEATURE:
<223> OTHER INFORMATION: GS7-FXa-GS7 linker

<400> SEQUENCE: 9

Gly Gly Gly Gly Ser Gly Gly Gly Gly Ser Gly Gly Gly Gly Ser Gly
 1               5                  10                  15

Gly Gly Ser Gly Gly Gly Ser Gly Gly Gly Ser Gly Gly Gly Ser Gly Gly
            20                  25                  30

Gly Gly Ser Ile Glu Gly Arg Gly Gly Gly Gly Ser Gly Gly Gly Gly
            35                  40                  45

Ser Gly Gly Gly Gly Ser Gly Gly Gly Gly Ser Gly Gly Gly Gly Ser
        50                  55                  60

Gly Gly Gly Gly Ser Gly Gly Gly Gly Ser Tyr Gly
 65                  70                  75

<210> SEQ ID NO 10
<211> LENGTH: 15
<212> TYPE: PRT
<213> ORGANISM: Artificial Sequence
<220> FEATURE:
<223> OTHER INFORMATION: GS1-FXIa linker

<400> SEQUENCE: 10

Gly Gly Gly Gly Ser Ser Lys Leu Thr Arg Ala Glu Thr Val Phe
 1               5                  10                  15

<210> SEQ ID NO 11
<211> LENGTH: 82
<212> TYPE: PRT
<213> ORGANISM: Artificial Sequence
<220> FEATURE:
<223> OTHER INFORMATION: GS7-FXIa-GS7 linker

<400> SEQUENCE: 11

Gly Gly Gly Gly Ser Gly Gly Gly Gly Ser Gly Gly Gly Gly Ser Gly
 1               5                  10                  15

Gly Gly Ser Gly Gly Gly Ser Gly Gly Gly Ser Gly Gly Gly Ser Gly Gly
            20                  25                  30

Gly Gly Ser Ser Lys Leu Thr Arg Ala Glu Thr Val Phe Gly Gly Gly
            35                  40                  45
```

Gly Ser Gly Gly Gly Gly Ser Gly Gly Gly Ser Gly Gly Gly Gly
          50                  55                  60

Ser Gly Gly Gly Ser Gly Gly Gly Ser Gly Gly Gly Ser
 65                  70                  75                  80

Tyr Gly

<210> SEQ ID NO 12
<211> LENGTH: 2840
<212> TYPE: DNA
<213> ORGANISM: Artificial Sequence
<220> FEATURE:
<223> OTHER INFORMATION: synthetic construct of gene encoding fusion
      protein FIX(KOI)-TF

<400> SEQUENCE: 12

| | | | | |
|---|---|---|---|---|
| gaattcgatt | accactttca | caatctagcc | accatggagc gcgtgaacat | gatcatggca | 60 |
| gaatcaccag | gcctcatcac | catctgcctt | ttaggatatc tactcagtgc | tgaatgtaca | 120 |
| ggtttgtttc | cttttttaaa | atacattgag | tatgcttgcc ttttagatat | agaaatatct | 180 |
| gatgctgtct | tcttcactaa | attttgatta | catgatttga cagcaatatt | gaagagtcta | 240 |
| acagccagca | cgcaggttgg | taagtactgg | ttctttgtta gctaggtttt | cttcttcttc | 300 |
| attttttaaaa | ctaaatagat | cgacaatgct | tatgatgcat ttatgtttaa | taaacactgt | 360 |
| tcagttcatg | atttggtcat | gtaattcctg | ttagaaaaca ttcatctcct | tggtttaaaa | 420 |
| aaattaaaag | tgggaaaaca | agaaatagc | agaatatagt gaaaaaaat | aaccacatta | 480 |
| tttttgtttg | gacttaccac | tttgaaatca | aatgggaaa caaaagcaca | acaatggcc | 540 |
| ttatttacac | aaaaagtctg | attttaagat | atatgacatt tcaaggtttc | agaagtatgt | 600 |
| aatgaggtgt | gtctctaatt | ttttaaatta | tatatcttca atttaaagtt | ttagttaaaa | 660 |
| cataaagatt | aaccctttcat | tagcaagctg | ttagttatca ccaaagcttt | tcatggatta | 720 |
| ggaaaaaatc | attttgtctc | tatgtcaaac | atcttggagt tgatatttgg | ggaaacacaa | 780 |
| tactcagttg | agttccctag | gggagaaaag | caagcttaag aattgacata | agagtagga | 840 |
| agttagctaa | tgcaacatat | atcactttgt | tttttcacaa ctacagtgac | tttatgtatt | 900 |
| tcccagagga | aggcatacag | ggaagaaatt | atcccatttg acaaacagc | atgttctcac | 960 |
| aggaagcatt | tatcacactt | acttgtcaac | tttctagaat caaatctagt | agctgacagt | 1020 |
| accaggatca | ggggtgccaa | ccctaagcac | ccccagaaag ctgactggcc | ctgtggttcc | 1080 |
| cactccagac | atgatgtcag | ctggaccata | attaggcttc tgttcttcag | gagacatttg | 1140 |
| ttcaaagtca | tttgggcaac | catattctga | aaacagccca gccagggtga | tggatcactt | 1200 |
| tgcaaagatc | ctcaatgagc | tattttcaag | tgatgacaaa gtgtgaagtt | aaccgctcat | 1260 |
| ttgagaactt | tctttttcat | ccaaagtaaa | ttcaaatatg attagaaatc | tgaccttta | 1320 |
| ttactggaat | tctcttgact | aaaagtaaaa | ttgaattta attcctaaat | ctccatgtgt | 1380 |
| atacagtact | gtgggaacat | cacagatttt | ggctccatgc cctaaagaga | aattggcttt | 1440 |
| cagattattt | ggattaaaaa | caaagacttt | cttaagagat gtaaattttt | catgatgttt | 1500 |
| tcttttttgc | taaaactaaa | gaattattct | tttacatttc agttttttctt | gatcatgaaa | 1560 |
| acgccaacaa | aattctgaat | cggccaaaga | ggtataattc aggtaaattg | gaagagtttg | 1620 |
| ttcaagggaa | ccttgagaga | gaatgtatgg | aagaaaagtg tagttttgaa | gaagcacgag | 1680 |
| aagttttga | aaaacactgaa | agaacaactg | aattttggaa gcagtatgtt | gatggagatc | 1740 |
| agtgtgagtc | caatccatgt | ttaaatggcg | gcagttgcaa ggatgacatt | aattcctatg | 1800 |

```
aatgttggtg tcccctttgga tttgaaggaa agaactgtga attagatgta acatgtaaca    1860
ttaagaatgg cagatgcgag cagttttgta aaaatagtgc tgataacaag gtggtttgct    1920
cctgtactga gggatatcga cttgcagaaa accagaagtc ctgtgaacca gcagtgccat    1980
ttccatgtgg aagagtttct gtttcacaaa cttctaagct cacccgtgct gaggctgttt    2040
ttcctgatgt ggactatgta aattctactg aagctgaaac cattttggat aacatcactc    2100
aaagcaccca atcatttaat gacttcactc gggttgttgg tggagaagat gccaaaccag    2160
gtcaattccc ttggcaggtt gttttgaatg gtaaagttga tgcattctgt ggaggctcta    2220
tcgttaatga aaaatggatt gtaactgctg cccactgtgt tgaaactggt gttaaaatta    2280
cagttgtcgc aggtgaacat aatattgagg agacagaaca tacagagcaa aagcgaaatg    2340
tgattcgaat tattcctcac cacaactaca atgcagctat taataagtac aaccatgaca    2400
ttgcccttct ggaactggac gaacccttag tgctaaacag ctacgttaca cctatttgca    2460
ttgctgacaa ggaatacacg aacatcttcc tcaaatttgg atctggctat gtaagtggct    2520
ggggaagagt cttccacaaa gggagatcag ctttagttct tcagtacctt agagttccac    2580
ttgttgaccg agccacatgt cttcgatcta caaagttcac catctataac aacatgttct    2640
gtgctggctt ccatgaagga ggtagagatt catgtcaagg agatagtggg ggaccccatg    2700
ttactgaagt ggaagggacc agtttcttaa ctggaattat tagctggggt gaagagtgtg    2760
caatgaaagg caaatatgga atatatacca aggtatcccg gtatgtcaac tggattaagg    2820
aaaaaacaaa gctcacttaa                                                2840

<210> SEQ ID NO 13
<211> LENGTH: 4892
<212> TYPE: DNA
<213> ORGANISM: Artificial Sequence
<220> FEATURE:
<223> OTHER INFORMATION: synthetic construct of gene encoding fusion
      protein FIX(KOI)-GS1-TF

<400> SEQUENCE: 13
gaattcgatt accactttca caatctagcc accatggagc gcgtgaacat gatcatggca     60
gaatcaccag gcctcatcac catctgcctt ttaggatatc tactcagtgc tgaatgtaca    120
ggtttgtttc cttttttaaa atacattgag tatgcttgcc ttttagatat agaaatatct    180
gatgctgtct tcttcactaa attttgatta catgatttga cagcaatatt gaagagtcta    240
acagccagca cgcaggttgg taagtactgg ttctttgtta gctaggtttt cttcttcttc    300
attttttaaaa ctaaatagat cgacaatgct tatgatgcat ttatgtttaa taaacactgt    360
tcagttcatg atttggtcat gtaattcctg ttagaaaaca ttcatctcct tggtttaaaa    420
aaattaaaag tgggaaaaca aagaaatagc agaatatagt gaaaaaaaat aaccacatta    480
tttttgtttg gacttaccac tttgaaatca aatgggaaa caaaagcaca acaatggcc     540
ttatttacac aaaaagtctg attttaagat atatgacatt tcaaggtttc agaagtatgt    600
aatgaggtgt gtctctaatt ttttaaatta tatatcttca atttaaagtt ttagttaaaa    660
cataaagatt aacctttcat tagcaagctg ttagttatca ccaaagcttt tcatggatta    720
ggaaaaaatc attttgtctc tatgtcaaac atcttggagt tgatatttgg ggaaacacaa    780
tactcagttg agttccctag gggagaaaag caagcttaag aattgacata agagtagga    840
agttagctaa tgcaacatat atcactttgt tttttcacaa ctacagtgac tttatgtatt    900
tcccagagga aggcatacag ggaagaaatt atcccatttg gacaaacagc atgttctcac    960
```

```
aggaagcatt tatcacactt acttgtcaac tttctagaat caaatctagt agctgacagt    1020
accaggatca ggggtgccaa ccctaagcac cccagaaag ctgactggcc ctgtggttcc     1080
cactccagac atgatgtcag ctggaccata attaggcttc tgttcttcag gagacatttg    1140
ttcaaagtca tttgggcaac catattctga aaacagccca gccagggtga tggatcactt    1200
tgcaaagatc ctcaatgagc tatttttcaag tgatgacaaa gtgtgaagtt aaccgctcat   1260
ttgagaactt tctttttcat ccaaagtaaa ttcaaatatg attagaaatc tgacctttta   1320
ttactggaat tctcttgact aaaagtaaaa ttgaatttta attcctaaat ctccatgtgt    1380
atacagtact gtgggaacat cacagatttt ggctccatgc cctaaagaga aattggcttt    1440
cagattattt ggattaaaaa caaagacttt cttaagagat gtaaaatttt catgatgttt    1500
tcttttttgc taaaactaaa gaattattct tttacatttc agttttttctt gatcatgaaa   1560 acgccaacaa aattctgaat cggccaaaga ggtataattc aggtaaattg aagagtttg     1620 ttcaagggaa ccttgagaga gaatgtatgg aagaaaagtg tagttttgaa gaagcacgag    1680 aagttttga aaacactgaa agaacaactg aattttggaa gcagtatgtt gatggagatc     1740
agtgtgagtc caatccatgt ttaaatggcg gcagttgcaa ggatgacatt aattcctatg    1800
aatgttggtg tccctttgga tttgaaggaa agaactgtga attagatgta acatgtaaca    1860
ttaagaatgg cagatgcgag cagttttgta aaaatagtgc tgataacaag gtggtttgct    1920
cctgtactga gggatatcga cttgcagaaa accagaagtc ctgtgaacca gcagtgccat    1980
ttccatgtgg aagagtttct gtttcacaaa cttctaagct cacccgtgct gaggctgttt    2040
ttcctgatgt ggactatgta aattctactg aagctgaaac catttggat aacatcactc     2100 aaagcaccca atcatttaat gacttcactc gggttgttgg tggagaagat gccaaccag     2160 gtcaattccc ttggcaggtt gttttgaatg gtaaagttga tgcattctgt ggaggctcta    2220
tcgttaatga aaaatggatt gtaactgctg cccactgtgt tgaaactggt gttaaaatta    2280
cagttgtcgc aggtgaacat aatattgagg agacagaaca tacagagcaa aagcgaaatg    2340
tgattcgaat tattcctcac cacaactaca atgcagctat taataagtac aaccatgaca    2400
ttgcccttct ggaactggac gaacccttag tgctaaacag ctacgttaca cctatttgca    2460
ttgctgacaa ggaatacacg aacatcttcc tcaaatttgg atctggctat gtaagtggct    2520
ggggaagagt cttccacaaa gggagatcag ctttagttct tcagtacctt agagttccac    2580 tgttgaccg agccacatgt cttcgatcta caaagttcac catctataac aacatgttct    2640
gtgctggctt ccatgaagga ggtagagatt catgtcaagg agatagtggg gaccccatg     2700 ttactgaagt ggaagggacc agtttcttaa ctggaattat tagctggggt gaagagtgtg    2760
caatgaaagg caaatatgga atatatacca aggtatcccg gtatgtcaac tggattaagg    2820 aaaaacaaa gctcaccggt ggaggcggat ccgtccctga taaaactgtg agatggtgtg    2880
cagtgtcgga gcatgaggcc actaagtgcc agagtttccg cgaccatatg aaaagcgtca    2940
ttccatccga tggtcccagt gttgcttgtg tgaagaaagc ctcctacctt gattgcatca    3000
gggccattgc ggcaaacgaa gcggatgctg tgacactgga tgcaggtttg gtgtatgatg    3060
cttacctggc tccaataac ctgaagcctg tggtggcaga gttctatggg tcaaaagagg     3120
atccacagac tttctattat gctgttgctg tggtgaagaa ggatagtggc ttccagatga    3180
accagcttcg aggcaagaag tcctgccaca cgggtctagg caggtccgct gggtggaaca    3240
tccccatagg cttactttac tgtgacttac ctgagccacg taaacctctt gagaaagcag    3300
tggccaattt cttctcgggc agctgtgccc cttgtgcgga tgggacggac ttcccccagc    3360
```

```
tgtgtcaact gtgtccaggg tgtggctgct ccacccttaa ccaatacttc ggctactcag    3420
gagccttcaa gtgtctgaag gatggtgctg gggatgtggc ctttgtcaag cactcgacta    3480
tatttgagaa cttggcaaac aaggctgaca gggaccagta tgagctgctt tgcctggaca    3540
acacccggaa gccggtagat gaatacaagg actgccactt ggcccaggtc ccttctcata    3600
ccgtcgtggc ccgaagtatg ggcggcaagg aggacttgat ctgggagctt ctcaaccagg    3660
cccaggaaca ttttgcaaaa gacaaatcaa agaattccca actattcagc tctcctcatg    3720
ggaaggacct gctgtttaag gactctgccc acgggttttt aaaagtcccc cccaggatgg    3780
atgccaagat gtacctgggc tatgagtatg tcactgccat ccggaatcta cgggaaggca    3840
catgcccaga agccccaaca gatgaatgca agcctgtgaa gtggtgtgcg ctgagccacc    3900
acgagaggct caagtgtgat gagtggagtg ttaacagtgt agggaaaata gagtgtgtat    3960
cagcagagac caccgaagac tgcatcgcca agatcatgaa tggagaagct gatgccatga    4020
gcttggatgg agggtttgtc tacatagcgg gcaagtgtgg tctggtgcct gtcttggcag    4080
aaaactacaa taagagcgat aattgtgagg ataccagagg gcagggtat tttgctgtag    4140 cagtggtgaa gaaatcagct tctgacctca cctgggacaa tctgaaaggc aagaagtcct    4200
gccatacggc agttggcaga accgctggct ggaacatccc catgggcctg ctctacaata    4260
agatcaacca ctgcagattt gatgaatttt tcagtgaagg ttgtgcccct gggtctaaga    4320
aagactccag tctctgtaag ctgtgtatgg gctcaggcct aaacctgtgt gaacccaaca    4380
acaaagaggg atactacggc tacacaggcg ctttcaggtg tctggttgag aagggagatg    4440
tggcctttgt gaaacaccag actgtcccac agaacactgg gggaaaaaac cctgatccat    4500
gggctaagaa tctgaatgaa aaagactatg agttgctgtg ccttgatggt accaggaaac    4560
ctgtggagga gtatgcgaac tgccacctgg ccagagcccc gaatcacgct gtggtcacac    4620
ggaaagataa ggaagcttgc gtccacaaga tattacgtca acagcagcac ctatttggaa    4680
gcaacgtaac tgactgctcg ggcaactttt gtttgttccg gtcggaaacc aaggaccttc    4740
tgttcagaga tgcacagta tgtttggcca aacttcatga cagaaacaca tatgaaaaat    4800
acttaggaga agaatatgtc aaggctgttg gtaacctgag aaaatgctcc acctcatcac    4860
tcctggaagc ctgcactttc cgtagacctt aa    4892
```

<210> SEQ ID NO 14
<211> LENGTH: 4928
<212> TYPE: DNA
<213> ORGANISM: Artificial Sequence
<220> FEATURE:
<223> OTHER INFORMATION: synthetic construct of gene encoding fusion
      protein FIX(KOI)-GS1-THR-GS1-TF

<400> SEQUENCE: 14

```
gaattcgatt accactttca caatctagcc accatggagc gcgtgaacat gatcatggca     60
gaatcaccag gcctcatcac catctgcctt ttaggatatc tactcagtgc tgaatgtaca    120
ggtttgtttc ctttttttaaa atacattgag tatgcttgcc ttttagatat agaaatatct    180
gatgctgtct tcttcactaa attttgatta catgatttga cagcaatatt gaagagtcta    240
acagccagca cgcaggttgg taagtactgg ttctttgtta gctaggtttt cttcttcttc    300
atttttaaaa ctaaatagat cgacaatgct tatgatgcat ttatgtttaa taaacactgt    360
tcagttcatg atttggtcat gtaattcctg ttagaaaaca ttcatctcct tggttttaaa    420
aaattaaaag tgggaaaaca agaaatagc agaatatagt gaaaaaaaat aaccacatta    480
```

```
tttttgtttg gacttaccac tttgaaatca aaatgggaaa caaaagcaca aacaatggcc      540
ttatttacac aaaaagtctg attttaagat atatgacatt tcaaggtttc agaagtatgt      600
aatgaggtgt gtctctaatt ttttaaatta tatatcttca atttaaagtt ttagttaaaa      660
cataaagatt aacctttcat tagcaagctg ttagttatca ccaaagcttt tcatggatta      720
ggaaaaaatc attttgtctc tatgtcaaac atcttggagt tgatatttgg ggaaacacaa      780
tactcagttg agttccctag gggagaaaag caagcttaag aattgacata agagtagga       840 agttagctaa tgcaacatat atcactttgt ttttcacaa ctacagtgac tttatgtatt       900
tcccagagga aggcatacag ggaagaaatt atcccatttg acaaacagc atgttctcac       960 aggaagcatt tatcacactt acttgtcaac tttctagaat caaatctagt agctgacagt     1020
accaggatca ggggtgccaa ccctaagcac ccccagaaag ctgactggcc ctgtggttcc     1080
cactccagac atgatgtcag ctggaccata attaggcttc tgttcttcag agacatttg     1140 ttcaaagtca tttgggcaac catattctga aaacagccca gccagggtga tggatcactt     1200
tgcaaagatc ctcaatgagc tattttcaag tgatgacaaa gtgtgaagtt aaccgctcat     1260
ttgagaactt tcttttcat ccaaagtaaa ttcaaatatg attagaaatc tgacctttta      1320
ttactggaat tctcttgact aaaagtaaaa ttgaatttta attcctaaat ctccatgtgt     1380
atacagtact gtgggaacat cacagatttt ggctccatgc cctaaagaga aattggcttt     1440
cagattattt ggattaaaaa caaagacttt cttaagagat gtaaaatttt catgatgttt     1500 tctttttgc taaaactaaa gaattattct tttacatttc agtttttctt gatcatgaaa     1560
acgccaacaa aattctgaat cggccaaaga ggtataattc aggtaaattg gaagagtttg     1620
ttcaagggaa ccttgagaga gaatgtatgg aagaaaagtg tagttttgaa gaagcacgag     1680
aagtttttga aaacactgaa agaacaactg aattttggaa gcagtatgtt gatggagatc     1740
agtgtgagtc caatccatgt ttaaatggcg gcagttgcaa ggatgacatt aattcctatg     1800
aatgttggtg tcccttttgga tttgaaggaa agaactgtga attagatgta acatgtaaca     1860
ttaagaatgg cagatgcgag cagttttgta aaaatagtgc tgataacaag gtggtttgct     1920
cctgtactga gggatatcga cttgcagaaa accagaagtc ctgtgaacca gcagtgccat     1980
ttccatgtgg aagagtttct gtttcacaaa cttctaagct cacccgtgct gaggctgttt     2040
ttcctgatgt ggactatgta aattctactg aagctgaaac cattttggat aacatcactc     2100
aaagcaccca atcatttaat gacttcactc gggttgttgg tggagaagat gccaaaccag     2160
gtcaattccc ttggcaggtt gtttttgaatg gtaaagttga tgcattctgt ggaggctcta     2220
tcgttaatga aaaatggatt gtaactgctg cccactgtgt tgaaactggt gttaaaatta     2280
cagttgtcgc aggtgaacat aatattgagg agacagaaca tacagagcaa aagcgaaatg     2340
tgattcgaat tattcctcac cacaactaca atgcagctat taataagtac aaccatgaca     2400
ttgcccttct ggaactggac gaaccccttag tgctaaacag ctacgttaca cctatttgca     2460
ttgctgacaa ggaatacacg aacatcttcc tcaaatttgg atctggctat gtaagtggct     2520
ggggaagagt cttccacaaa gggagatcag ctttagttct tcagtaccct agagttccac     2580
ttgttgaccg agccacatgt cttcgatcta caaagttcac catctataac aacatgttct     2640
gtgctggctt ccatgaagga ggtagagatt catgtcaagg agatagtggg ggaccccatg     2700
ttactgaagt ggaagggacc agtttcttaa ctggaattat tagctggggt gaagagtgtg     2760
caatgaaagg caaatatgga atatataacc aggtatcccg gtatgtcaac tggattaagg     2820
```

```
aaaaaacaaa gctcaccggt ggaggcggat ccctggtgcc gcgcggcagc ggaggcggtt      2880
caaccggtga taaaactgtg agatggtgtg cagtgtcgga gcatgaggcc actaagtgcc      2940
gtccctagag tttccgcgac catatgaaaa gcgtcattcc atccgatggt cccagtgttg      3000
cttgtgtgaa gaaagcctcc taccttgatt gcatcagggc cattgcggca aacgaagcgg      3060
atgctgtgac actggatgca ggtttggtgt atgatgctta cctggctccc aataacctga      3120
agcctgtggt ggcagagttc tatgggtcaa aagaggatcc acagactttc tattatgctg      3180
ttgctgtggt gaagaaggat agtggcttcc agatgaacca gcttcgaggc aagaagtcct      3240
gccacacggg tctaggcagg tccgctgggt ggaacatccc cataggctta ctttactgtg      3300
acttacctga gccacgtaaa cctcttgaga aagcagtggc caatttcttc tcgggcagct      3360
gtgcccttg tgcggatggg acggacttcc cccagctgtg tcaactgtgt ccagggtgtg      3420
gctgctccac ccttaaccaa tacttcggct actcaggagc cttcaagtgt ctgaaggatg      3480
gtgctgggga tgtggccttt gtcaagcact cgactatatt tgagaacttg gcaaacaagg      3540
ctgacaggga ccagtatgag ctgctttgcc tggacaacac ccggaagccg gtagatgaat      3600
acaaggactg ccacttggcc caggtcccct ctcataccgt cgtggcccga agtatgggcg      3660
gcaaggagga cttgatctgg gagcttctca accaggccca ggaacatttt ggcaaagaca      3720
aatcaaaaga attccaacta ttcagctctc ctcatgggaa ggacctgctg tttaaggact      3780
ctgcccacgg gtttttaaaa gtcccccccca ggatggatgc caagatgtac ctgggctatg      3840
agtatgtcac tgccatccgg aatctacggg aaggcacatg cccagaagcc caacagatg      3900
aatgcaagcc tgtgaagtgg tgtgcgctga gccaccacga gaggctcaag tgtgatgagt      3960
ggagtgttaa cagtgtaggg aaaatagagt gtgtatcagc agagaccacc gaagactgca      4020
tcgccaagat catgaatgga gaagctgatg ccatgagctt ggatggaggg tttgtctaca      4080
tagcgggcaa gtgtggtctg gtgcctgtct tggcagaaaa ctacaataag agcgataatt      4140
gtgaggatac accagaggca gggtattttg ctgtagcagt ggtgaagaaa tcagcttctg      4200
acctcacctg ggacaatctg aaaggcaaga agtcctgcca tacggcagtt ggcagaaccg      4260
ctggctggaa catccccatg ggcctgctct acaataagat caaccactgc agatttgatg      4320
aatttttcag tgaaggttgt gcccctgggt ctaagaaaga ctccagtctc tgtaagctgt      4380
gtatgggctc aggcctaaac ctgtgtgaac ccaacaacaa agagggatac tacggctaca      4440
caggcgcttt caggtgtctg gttgagaagg gagatgtggc ctttgtgaaa caccagactg      4500
tcccacagaa cactggggga aaaaaccctg atccatgggc taagaatctg aatgaaaaag      4560
actatgagtt gctgtgcctt gatggtacca ggaaacctgt ggaggagtat gcgaactgcc      4620
acctggccag agccccgaat cacgctgtgg tcacacggaa agataaggaa gcttgcgtcc      4680
acaagatatt acgtcaacag cagcaccat ttggaagcaa cgtaactgac tgctcgggca      4740
acttttgttt gttccggtcg gaaaccaagg accttctgtt cagagatgac acagtatgtt      4800
tggccaaaact tcatgacaga aacacatatg aaaaatactt aggagaagaa tatgtcaagg      4860
ctgttggtaa cctgagaaaa tgctccacct catcactcct ggaagcctgc actttccgta      4920
gaccttaa                                                              4928
```

<210> SEQ ID NO 15
<211> LENGTH: 4922
<212> TYPE: DNA
<213> ORGANISM: Artificial Sequence
<220> FEATURE:
<223> OTHER INFORMATION: synthetic construct of gene encoding fusion protein FIX(KOI)-GS1-THR-GS1-del-TF

<400> SEQUENCE: 15

```
gaattcgatt accactttca caatctagcc accatggagc gcgtgaacat gatcatggca      60
gaatcaccag gcctcatcac catctgcctt ttaggatatc tactcagtgc tgaatgtaca     120
ggtttgtttc cttttttaaa atacattgag tatgcttgcc ttttagatat agaaatatct     180
gatgctgtct tcttcactaa attttgatta catgatttga cagcaatatt gaagagtcta     240
acagccagca cgcaggttgg taagtactgg ttctttgtta gctaggtttt cttcttcttc     300
attttaaaa ctaaatagat cgacaatgct tatgatgcat ttatgtttaa taaacactgt     360
tcagttcatg atttggtcat gtaattcctg ttagaaaaca ttcatctcct tggtttaaaa     420
aaattaaaag tgggaaaaca agaaatagc agaatatagt gaaaaaaat aaccacatta     480
tttttgtttg gacttaccac tttgaaatca aatgggaaa caaaagcaca acaatggcc     540
ttatttacac aaaaagtctg attttaagat atatgacatt tcaaggtttc agaagtatgt     600
aatgaggtgt gtctctaatt ttttaaatta tatatcttca atttaaagtt ttagttaaaa     660
cataaagatt aaccttcat tagcaagctg ttagttatca ccaaagcttt tcatggatta     720
ggaaaaaatc attttgtctc tatgtcaaac atcttggagt tgatatttgg ggaaacacaa     780
tactcagttg agttccctag gggagaaaag caagcttaag aattgacata agagtagga     840
agttagctaa tgcaacatat atcactttgt ttttcacaa ctacagtgac tttatgtatt     900
tcccagagga aggcatacag ggaagaaatt atccatttg acaaacagc atgttctcac     960
aggaagcatt tatcacactt acttgtcaac tttctagaat caaatctagt agctgacagt    1020
accaggatca ggggtgccaa ccctaagcac ccccagaaag ctgactggcc ctgtggttcc    1080
cactccagac atgatgtcag ctggaccata attaggcttc tgttcttcag gagacatttg    1140
ttcaaagtca tttgggcaac catattctga aaacagccca gccagggtga tggatcactt    1200
tgcaaagatc ctcaatgagc tattttcaag tgatgacaaa gtgtgaagtt aaccgctcat    1260
ttgagaactt tcttttttcat ccaaagtaaa ttcaaatatg attagaaatc tgaccttta    1320
ttactggaat tctcttgact aaaagtaaaa ttgaatttta attcctaaat ctccatgtgt    1380
atacagtact gtgggaacat cacagatttt ggctccatgc cctaaagaga aattggcttt    1440
cagattattt ggattaaaaa caaagacttt cttaagagat gtaaaattt catgatgttt    1500
tctttttgc taaaactaaa gaattattct tttacatttc agttttttctt gatcatgaaa    1560
acgccaacaa aattctgaat cggccaaaga ggtataatt aggtaaattg aaagagtttg    1620
ttcaagggaa ccttgagaga gaatgtatgg aagaaaagtg tagttttgaa gaagcacgag    1680
aagttttga aaacactgaa agaacaactg aattttggaa gcagtatgtt gatggagatc    1740
agtgtgagtc caatccatgt ttaaatggcg gcagttgcaa ggatgacatt aattcctatg    1800
aatgttggtg tcccttgga tttgaaggaa agaactgtga attagatgta acatgtaaca    1860
ttaagaatgg cagatgcgag cagttttgta aaaatagtgc tgataacaag gtggtttgct    1920
cctgtactga gggatatcga cttgcagaaa accagaagtc ctgtgaacca gcagtgccat    1980
ttccatgtgg aagagtttct gtttcacaaa cttctaagct caccgtgct gaggctgttt    2040
ttcctgatgt ggactatgta aattctactg aagctgaaac cattttggat aacatcactc    2100
aaagcaccca atcattaat gacttcactc gggttgttgg tggagaagat gccaaaccag    2160
gtcaattccc ttggcaggtt gttttgaatg gtaaagttga tgcattctgt ggaggctcta    2220
```

```
tcgttaatga aaaatggatt gtaactgctg cccactgtgt tgaaactggt gttaaaatta    2280
cagttgtcgc aggtgaacat aatattgagg agacagaaca tacagagcaa aagcgaaatg    2340
tgattcgaat tattcctcac cacaactaca atgcagctat taataagtac aaccatgaca    2400
ttgcccttct ggaactggac gaacccttag tgctaaacag ctacgttaca cctatttgca    2460
ttgctgacaa ggaatacacg aacatcttcc tcaaatttgg atctggctat gtaagtggct    2520
ggggaagagt cttccacaaa gggagatcag ctttagttct tcagtacctt agagttccac    2580
ttgttgaccg agccacatgt cttcgatcta caaagttcac catctataac aacatgttct    2640
gtgctggctt ccatgaagga ggtagagatt catgtcaagg agatagtggg ggaccccatg    2700
ttactgaagt ggaagggacc agtttcttaa ctggaattat tagctggggt gaagagtgtg    2760
caatgaaagg caaatatgga atatatacca aggtatcccg gtatgtcaac tggattaagg    2820
aaaaaacaaa gctcaccggt ggaggcggat ccctggtgcc gcgcggcagc ggaggcggtt    2880
cagtccctga taaaactgtg agatggtgtg cagtgtcgga gcatgaggcc actaagtgcc    2940
agagtttccg cgaccatatg aaaagcgtca ttccatccga tggtcccagt gttgcttgtg    3000
tgaagaaagc ctcctacctt gattgcatca gggccattgc ggcaaacgaa gcggatgctg    3060
tgacactgga tgcaggtttg gtgtatgatg cttacctggc tcccaataac ctgaagcctg    3120
tggtggcaga gttctatggg tcaaaagagg atccacagac tttctattat gctgttgctg    3180
tggtgaagaa ggatagtggc ttccagatga accagcttcg aggcaagaag tcctgccaca    3240
cgggtctagg caggtccgct gggtggaaca tccccatagg cttactttac tgtgacttac    3300
ctgagccacg taaacctctt gagaaagcag tggccaattt cttctcgggc agctgtgccc    3360
cttgtgcgga tgggacggac ttcccccagc tgtgtcaact gtgtccaggg tgtggctgct    3420 ccaccctta a ccaatacttc ggctactcag gagccttcaa gtgtctgaag gatggtgctg    3480
gggatgtggc ctttgtcaag cactcgacta tatttgagaa cttggcaaac aaggctgaca    3540
gggaccagta tgagctgctt tgcctggaca cacccggaa gccggtagat gaatacaagg    3600
actgccactt ggcccaggtc ccttctcata ccgtcgtggc ccgaagtatg ggcggcaagg    3660
aggacttgat ctgggagctt ctcaaccagg cccaggaaca ttttggcaaa gacaaatcaa    3720
aagaattcca actattcagc tctcctcatg ggaaggacct gctgtttaag gactctgccc    3780
acgggttttt aaaagtcccc cccaggatgg atgccaagat gtacctgggc tatgagtatg    3840
tcactgccat ccggaatcta cgggaaggca catgcccaga agccccaaca gatgaatgca    3900
agcctgtgaa gtggtgtgcg ctgagccacc acgagaggct caagtgtgat gagtggagtg    3960
ttaacagtgt agggaaaata gagtgtgtat cagcagagac caccgaagac tgcatcgcca    4020
agatcatgaa tggagaagct gatgccatga gcttggatgg aggg tttgtc tacatagcgg    4080 gcaagtgtgg tctggtgcct gtcttggcag aaaactacaa taagagcgat aattgtgagg    4140
atacaccaga ggcagggtat tttgctgtag cagtggtgaa gaaatcagct tctgacctca    4200
cctgggacaa tctgaaaggc aagaagtcct gccatacggc agttggcaga accgctggct    4260
ggaacatccc catgggcctg ctctacaata gatcaaccca ctgcagattt gatgaatttt    4320
tcagtgaagg ttgtgcccct gggtctaaga agactccag tctctgtaag ctgtgtatgg    4380
gctcaggcct aaacctgtgt gaacccaaca caaagaggg atactacggc tacacaggcg    4440 cttt caggtg tctggttgag aagggagatg tggccttt gt gaaacaccag actgtcccac    4500
agaacactgg gggaaaaaac cctgatccat gggctaagaa tctgaatgaa aaagactatg    4560
```

-continued

```
agttgctgtg ccttgatggt accaggaaac ctgtggagga gtatgcgaac tgccacctgg   4620
ccagagcccc gaatcacgct gtggtcacac ggaaagataa ggaagcttgc gtccacaaga   4680
tattacgtca acagcagcac ctatttggaa gcaacgtaac tgactgctcg ggcaactttt   4740
gtttgttccg gtcggaaacc aaggaccttc tgttcagaga tgacacagta tgtttggcca   4800
aacttcatga cagaaacaca tatgaaaaat acttaggaga agaatatgtc aaggctgttg   4860
gtaacctgag aaaatgctcc acctcatcac tcctggaagc ctgcactttc cgtagacctt   4920
aa                                                                  4922
```

<210> SEQ ID NO 16
<211> LENGTH: 4910
<212> TYPE: DNA
<213> ORGANISM: Artificial Sequence
<220> FEATURE:
<223> OTHER INFORMATION: synthetic construct of gene encoding fusion protein FIX(KOI)-GS1-FXa-TF

<400> SEQUENCE: 16

```
gaattcgatt accactttca caatctagcc accatggagc gcgtgaacat gatcatggca     60
gaatcaccag gcctcatcac catctgcctt ttaggatatc tactcagtgc tgaatgtaca    120
ggtttgtttc ctttttttaaa atacattgag tatgcttgcc ttttagatat agaaatatct   180
gatgctgtct tcttcactaa attttgatta catgatttga cagcaatatt gaagagtcta    240
acagccagca cgcaggttgg taagtactgg ttctttgtta gctaggtttt cttcttcttc    300
atttttaaaa ctaaatagat cgacaatgct tatgatgcat ttatgtttaa taaacactgt    360
tcagttcatg atttggtcat gtaattcctg ttagaaaaca ttcatctcct tggtttaaaa    420
aaattaaaag tgggaaaaca aagaaatagc agaatatagt gaaaaaaaat aaccacatta    480
tttttgtttg gacttaccac tttgaaatca aaatgggaaa caaaagcaca aacaatggcc    540
ttatttacac aaaaagtctg attttaagat atatgacatt tcaaggtttc agaagtatgt    600
aatgaggtgt gtctctaatt ttttaaatta tatatcttca atttaaagtt ttagttaaaa    660
cataaagatt aacctttcat tagcaagctg ttagttatca ccaaagcttt tcatggatta    720
ggaaaaaatc attttgtctc tatgtcaaac atcttggagt tgatatttgg ggaaacacaa    780
tactcagttg agttccctag ggagagaaag caagcttaag aattgacata aagagtagga    840
agttagctaa tgcaacatat atcactttgt tttttcacaa ctacagtgac tttatgtatt    900
tcccagagga aggcatacag ggaagaaatt atcccatttg gacaaacagc atgttctcac    960
aggaagcatt tatcacactt acttgtcaac tttctagaat caaatctagt agctgacagt   1020
accaggatca ggggtgccaa ccctaagcac ccccagaaag ctgactggcc ctgtggttcc   1080
cactccagac atgatgtcag ctggaccata attaggcttc tgttcttcag gagacatttg   1140
ttcaaagtca tttgggcaac catattctga aaacagccca gccagggtga tggatcactt   1200
tgcaaagatc ctcaatgagc tattttcaag tgatgacaaa gtgtgaagtt aaccgctcat   1260
ttgagaactt tctttttcat ccaaagtaaa ttcaaatatg attagaaatc tgacctttta   1320
ttactggaat tctcttgact aaaagtaaaa ttgaatttta attcctaaat ctccatgtgt   1380
atacagtact gtgggaacat cacagatttt ggctccatgc cctaaagaga aattggcttt   1440
cagattattt ggattaaaaa caaagacttt cttaagagat gtaaaatttt catgatgttt   1500
tctttttgc taaaactaaa gaattattct tttacatttc agtttttctt gatcatgaaa    1560
acgccaacaa aattctgaat cggccaaaga ggtataattc aggtaaattg gaagagtttg   1620
```

```
ttcaaggaa  ccttgagaga  gaatgtatgg  aagaaaagtg  tagttttgaa  gaagcacgag   1680
aagttttga  aaacactgaa  agaacaactg  aattttggaa  gcagtatgtt  gatggagatc   1740
agtgtgagtc  caatccatgt  ttaaatggcg  gcagttgcaa  ggatgacatt  aattcctatg   1800
aatgttggtg  tcccttttgga  tttgaaggaa  agaactgtga  attagatgta  acatgtaaca   1860
ttaagaatgg  cagatgcgag  cagttttgta  aaaatagtgc  tgataacaag  gtggtttgct   1920
cctgtactga  gggatatcga  cttgcagaaa  accagaagtc  ctgtgaacca  gcagtgccat   1980
ttccatgtgg  aagagtttct  gtttcacaaa  cttctaagct  cacccgtgct  gaggctgttt   2040
ttcctgatgt  ggactatgta  aattctactg  aagctgaaac  catttggat  aacatcactc    2100
aaagcaccca  atcatttaat  gacttcactc  gggttgttgg  tggagaagat  gccaaaccag   2160
gtcaattccc  ttggcaggtt  gttttgaatg  gtaaagttga  tgcattctgt  ggaggctcta   2220
tcgttaatga  aaaatggatt  gtaactgctg  cccactgtgt  tgaaactggt  gttaaaatta   2280
cagttgtcgc  aggtgaacat  aatattgagg  agacagaaca  tacagagcaa  aagcgaaatg   2340
tgattcgaat  tattcctcac  cacaaactaca  atgcagctat  taataagtac  aaccatgaca   2400
ttgcccttct  ggaactggac  gaaccttag   tgctaaacag  ctacgttaca  cctatttgca   2460
ttgctgacaa  ggaatacacg  aacatcttcc  tcaaatttgg  atctggctat  gtaagtggct   2520
ggggaagagt  cttccacaaa  gggagatcag  ctttagttct  tcagtacctt  agagttccac   2580
ttgttgaccg  agccacatgt  cttcgatcta  caaagttcac  catctataac  aacatgttct   2640
gtgctggctt  ccatgaagga  ggtagagatt  catgtcaagg  agatagtggg  ggaccccatg   2700
ttactgaagt  ggaagggacc  agtttcttaa  ctggaattat  tagctggggt  gaagagtgtg   2760
caatgaaagg  caaatatgga  atatatacca  aggtatcccg  gtatgtcaac  tggattaagg   2820
aaaaaacaaa  gctcaccggt  ggaggcgat  ctatagaagg  ccgaggatcc  gtccctgata   2880
aaactgtgag  atggtgtgca  gtgtcggagc  atgaggccac  taagtgccag  agtttccgcg   2940
accatatgaa  aagcgtcatt  ccatccgatg  gtcccagtgt  tgcttgtgtg  aagaaagcct   3000
cctaccttga  ttgcatcagg  gccattgcgg  caaacgaagc  ggatgctgtg  acactggatg   3060
caggtttggt  gtatgatgct  tacctggctc  ccaataaccct  gaagcctgtg  gtggcagagt   3120
tctatgggtc  aaaagaggat  ccacagactt  tctattatgc  tgttgctgtg  gtgaagaagg   3180
atagtggctt  ccagatgaac  cagcttcgag  gcaagaagtc  ctgccacacg  ggtctaggca   3240
ggtccgctgg  gtgaacatc   cccataggct  tactttactg  tgacttacct  gagccacgta   3300
aacctcttga  gaaagcagtg  gccaatttct  tctcgggcag  ctgtgcccct  tgtgcggatg   3360
ggacggactt  cccccagctg  tgtcaactgt  gtccaggtg   tggctgctcc  acccttaacc   3420
aatacttcgg  ctactcagga  gccttcaagt  gtctgaagga  tggtgctggg  gatgtggcct   3480
tgtcaagca   ctcgactata  tttgagaact  tggcaaacaa  ggctgacagg  gaccagtatg   3540
agctgctttg  cctggacaac  acccggaagc  cggtagatga  atacaaggac  tgccacttgg   3600
cccaggtccc  ttctcatacc  gtcgtggccc  gaagtatggg  cggcaaggag  gacttgatct   3660
gggagcttct  caaccaggcc  caggaacatt  ttgcaaaga   caaatcaaaa  gaattccaac   3720
tattcagctc  tcctcatggg  aaggacctgc  tgtttaagga  ctctgcccac  gggttttaa   3780
aagtcccccc  caggatggat  gccaagatgt  acctgggcta  tgagtatgtc  actgccatcc   3840
ggaatctacg  ggaaggcaca  tgcccagaag  ccccaacaga  tgaatgcaag  cctgtgaagt   3900
ggtgtgcgct  gagccaccac  gagagggctca  agtgtgatga  gtggagtgtt  aacagtgtag   3960
ggaaaataga  gtgtgtatca  gcagagacca  ccgaagactg  catcgccaag  atcatgaatg   4020
```

```
gagaagctga tgccatgagc ttggatggag ggtttgtcta catagcgggc aagtgtggtc    4080
tggtgcctgt cttggcagaa aactacaata agagcgataa ttgtgaggat acaccagagg    4140
cagggtattt tgctgtagca gtggtgaaga aatcagcttc tgacctcacc tgggacaatc    4200
tgaaaggcaa gaagtcctgc catacggcag ttggcagaac cgctggctgg aacatcccca    4260
tgggcctgct ctacaataag atcaaccact gcagatttga tgaattttc agtgaaggtt     4320 gtgcccctgg gtctaagaaa gactccagtc tctgtaagct gtgtatgggc tcaggcctaa    4380
acctgtgtga acccaacaac aaagagggat actacggcta cacaggcgct ttcaggtgtc    4440
tggttgagaa gggagatgtg gcctttgtga acaccagac tgtcccacag aacactgggg     4500 gaaaaaccc tgatccatgg gctaagaatc tgaatgaaaa agactatgag ttgctgtgcc     4560
ttgatggtac caggaaacct gtggaggagt atgcgaactg ccacctggcc agagccccga    4620
atcacgctgt ggtcacacgg aaagataagg aagcttgcgt ccacaagata ttacgtcaac    4680
agcagcacct atttggaagc aacgtaactg actgctcggg caacttttgt ttgttccggt    4740
cggaaaccaa ggaccttctg ttcagagatg acacagtatg tttggccaaa cttcatgaca    4800
gaaacacata tgaaaatac ttaggagaag aatatgtcaa ggctgttggt aacctgagaa      4860
aatgctccac ctcatcactc ctggaagcct gcactttccg tagaccttaa                4910
```

<210> SEQ ID NO 17
<211> LENGTH: 4928
<212> TYPE: DNA
<213> ORGANISM: Artificial Sequence
<220> FEATURE:
<223> OTHER INFORMATION: synthetic construct of gene encoding fusion
      protein F IX(KOI)-GS1-FXIa-TF

<400> SEQUENCE: 17

```
gaattcgatt accactttca caatctagcc accatggagc gcgtgaacat gatcatggca      60
gaatcaccag gcctcatcac catctgcctt ttaggatatc tactcagtgc tgaatgtaca     120
ggtttgtttc cttttttaaa atacattgag tatgcttgcc ttttagatat agaaatatct     180
gatgctgtct tcttcactaa attttgatta catgatttga cagcaatatt gaagagtcta     240
acagccagca cgcaggttgg taagtactgg ttctttgtta gctaggtttt cttcttcttc     300 attttttaaaa ctaaatagat cgacaatgct tatgatgcat ttatgtttaa taaacactgt    360
tcagttcatg atttggtcat gtaattcctg ttagaaaaca ttcatctcct tggtttaaaa     420
aaattaaaag tgggaaaaca aagaaatagc agaatatagt gaaaaaaat aaccacatta      480 tttttgtttg gacttaccac tttgaaatca aatgggaaa caaaagcaca aacaatggcc      540
ttatttacac aaaaagtctg atttaagat atatgacatt tcaaggtttc agaagtatgt     600
aatgaggtgt gtctctaatt ttttaaatta tatatcttca atttaaagtt ttagttaaaa     660
cataaagatt aacctttcat tagcaagctg ttagttatca ccaaagcttt tcatggatta     720
ggaaaaaatc attttgtctc tatgtcaaac atcttggagt tgatatttgg ggaaacacaa     780
tactcagttg agttccctag gggagaaaag caagcttaag aattgacata aagagtagga     840
agttagctaa tgcaacatat atcactttgt tttttcacaa ctacagtgac tttatgtatt     900
tcccagagga aggcatacag ggaagaaatt atcccatttg acaaacagc atgttctcac      960 aggaagcatt tatcacactt acttgtcaac tttctagaat caaatctagt agctgacagt    1020
accaggatca ggggtgccaa ccctaagcac ccccagaaag ctgactggcc ctgtggttcc    1080
cactccagac atgatgtcag ctggaccata attaggcttc tgttcttcag gagacatttg    1140
```

-continued

| | |
|---|---|
| ttcaaagtca tttgggcaac catattctga aaacagccca gccagggtga tggatcactt | 1200 |
| tgcaaagatc tcaatgagc tattttcaag tgatgacaaa gtgtgaagtt aaccgctcat | 1260 |
| ttgagaactt tcttttcat ccaaagtaaa ttcaaatatg attagaaatc tgaccttta | 1320 |
| ttactggaat tctcttgact aaaagtaaaa ttgaatttta attcctaaat ctccatgtgt | 1380 |
| atacagtact gtgggaacat cacagatttt ggctccatgc cctaaagaga aattggcttt | 1440 |
| cagattattt ggattaaaaa caaagacttt cttaagagat gtaaaattt catgatgttt | 1500 |
| tcttttttgc taaaactaaa gaattattct tttacatttc agtttttctt gatcatgaaa | 1560 |
| acgccaacaa aattctgaat cggccaaaga ggtataattc aggtaaattg gaagagtttg | 1620 |
| ttcaagggaa ccttgagaga gaatgtatgg aagaaagtg tagttttgaa gaagcacgag | 1680 |
| aagtttttga aaacactgaa agaacaactg aattttggaa gcagtatgtt gatggagatc | 1740 |
| agtgtgagtc caatccatgt ttaaatggcg gcagttgcaa ggatgacatt aattcctatg | 1800 |
| aatgttggtg tccctttgga tttgaaggaa agaactgtga attagatgta acatgtaaca | 1860 |
| ttaagaatgg cagatgcgag cagttttgta aaaatagtgc tgataacaag gtggtttgct | 1920 |
| cctgtactga gggatatcga cttgcagaaa accagaagtc ctgtgaacca gcagtgccat | 1980 |
| tccatgtgg aagagtttct gtttcacaaa cttctaagct cacccgtgct gaggctgttt | 2040 |
| ttcctgatgt ggactatgta aattctactg aagctgaaac cattttggat aacatcactc | 2100 |
| aaagcaccca atcatttaat gacttcactc gggttgttgg tggagaagat gccaaaccag | 2160 |
| gtcaattccc ttggcaggtt gttttgaatg gtaaagttga tgcattctgt ggaggctcta | 2220 |
| tcgttaatga aaaatggatt gtaactgctg cccactgtgt tgaaactggt gttaaaatta | 2280 |
| cagttgtcgc aggtgaacat aatattgagg agacagaaca tacagagcaa aagcgaaatg | 2340 |
| tgattcgaat tattcctcac cacaactaca atgcagctat taataagtac aaccatgaca | 2400 |
| ttgcccttct ggaactggac gaaccttag tgctaaacag ctacgttaca cctatttgca | 2460 |
| ttgctgacaa ggaatacacg aacatcttcc tcaaatttgg atctggctat gtaagtggct | 2520 |
| ggggaagagt cttccacaaa gggagatcag ctttagttct tcagtacctt agagttccac | 2580 |
| ttgttgaccg agccacatgt cttcgatcta caaagttcac catctataac aacatgttct | 2640 |
| gtgctggctt ccatgaagga ggtagagatt catgtcaagg agatagtggg ggaccccatg | 2700 |
| ttactgaagt ggaagggacc agtttcttaa ctggaattat tagctggggt gaagagtgtg | 2760 |
| caatgaaagg caaatatgga atatatacca aggtatcccg gtatgtcaac tggattaagg | 2820 |
| aaaaaacaaa gctcaccggt ggaggcggat cttctaagct cacccgtgct gagactgttt | 2880 |
| ttggatccgt ccctgataaa actgtgagat ggtgtgcagt gtcggagcat gaggccacta | 2940 |
| agtgccagag tttccgcgac catatgaaaa gcgtcattcc atccgatggt cccagtgttg | 3000 |
| cttgtgtgaa gaaagcctcc taccttgatt gcatcagggc cattgcggca acgaagcgg | 3060 |
| atgctgtgac actggatgca ggtttggtgt atgatgctta cctggctccc aataacctga | 3120 |
| agcctgtggt ggcagagttc tatgggtcaa agaggatcc acagactttc tattatgctg | 3180 |
| ttgctgtggt gaagaaggat agtggcttcc agatgaacca gcttcgaggc aagaagtcct | 3240 |
| gccacacggg tctaggcagg tccgctgggt ggaacatccc cataggctta ctttactgtg | 3300 |
| acttacctga gccacgtaaa cctcttgaga agcagtggc caatttcttc tcgggcagct | 3360 |
| gtgccccttg tgcggatggg acggacttcc cccagctgtg tcaactgtgt ccagggtgtg | 3420 |
| gctgctccac ccttaaccaa tacttcggct actcaggagc cttcaagtgt ctgaaggatg | 3480 |

-continued

```
gtgctgggga tgtggccttt gtcaagcact cgactatatt tgagaacttg gcaaacaagg    3540
ctgacaggga ccagtatgag ctgctttgcc tggacaacac ccggaagccg gtagatgaat    3600
acaaggactg ccacttggcc caggtccctt ctcataccgt cgtggcccga agtatgggcg    3660
gcaaggagga cttgatctgg gagcttctca accaggccca ggaacatttt ggcaaagaca    3720
aatcaaaaga attccaacta ttcagctctc ctcatgggaa ggacctgctg tttaaggact    3780
ctgcccacgg gttttaaaa gtcccccca ggatggatgc caagatgtac ctgggctatg     3840
agtatgtcac tgccatccgg aatctacggg aaggcacatg cccagaagcc ccaacagatg    3900
aatgcaagcc tgtgaagtgg tgtgcgctga gccaccacga gaggctcaag tgtgatgagt    3960
ggagtgttaa cagtgtaggg aaaatagagt gtgtatcagc agagaccacc gaagactgca    4020
tcgccaagat catgaatgga gaagctgatg ccatgagctt ggatggaggg tttgtctaca    4080
tagcgggcaa gtgtggtctg gtgcctgtct tggcagaaaa ctacaataag agcgataatt    4140
gtgaggatac accagaggca gggtattttg ctgtagcagt ggtgaagaaa tcagcttctg    4200
acctcacctg ggacaatctg aaaggcaaga agtcctgcca tacggcagtt ggcagaaccg    4260
ctggctggaa catccccatg ggcctgctct acaataagat caaccactgc agatttgatg    4320
aattttttcag tgaaggttgt gcccctgggt ctaagaaaga ctccagtctc tgtaagctgt    4380
gtatgggctc aggcctaaac ctgtgtgaac ccaacaacaa agagggatac tacggctaca    4440
caggcgcttt caggtgtctg gttgagaagg gagatgtggc ctttgtgaaa caccagactg    4500
tcccacagaa cactggggga aaaaccctg atccatgggc taagaatctg aatgaaaaag    4560
actatgagtt gctgtgcctt gatggtacca ggaaacctgt ggaggagtat gcgaactgcc    4620
acctggccag agccccgaat cacgctgtgg tcacacggaa agataaggaa gcttgcgtcc    4680
acaagatatt acgtcaacag cagcacctat ttggaagcaa cgtaactgac tgctcgggca    4740
acttttgttt gttccggtcg gaaaccaagg accttctgtt cagagatgac acagtatgtt    4800
tggccaaaact tcatgacaga aacacatatg aaaaatactt aggagaagaa tatgtcaagg    4860
ctgttggtaa cctgagaaaa tgctccacct catcactcct ggaagcctgc actttccgta    4920
gaccttaa                                                             4928
```

<210> SEQ ID NO 18
<211> LENGTH: 5102
<212> TYPE: DNA
<213> ORGANISM: Artificial Sequence
<220> FEATURE:
<223> OTHER INFORMATION: synthetic construct of gene encoding fusion
      protein F IX(KOI)-GS15-TF

<400> SEQUENCE: 18

```
gaattcgatt accactttca caatctagcc accatggagc gcgtgaacat gatcatggca     60
gaatcaccag gcctcatcac catctgcctt ttaggatatc tactcagtgc tgaatgtaca    120
ggtttgtttc cttttttaaa atacattgag tatgcttgcc ttttagatat agaaatatct    180
gatgctgtct tcttcactaa attttgatta catgatttga cagcaatatt gaagagtcta    240
acagccagca cgcaggttgg taagtactgg ttctttgtta gctaggtttt cttcttcttc    300
atttttaaaa ctaaatagat cgacaatgct tatgatgcat ttatgtttaa taaacactgt    360
tcagttcatg atttggtcat gtaattcctg ttagaaaaca ttcatctcct tggttttaaaa   420
aaattaaaag tgggaaaaca aagaaatagc agaatatagt gaaaaaaaat aaccacatta   480
tttttgtttg gacttaccac tttgaaatca aatgggaaa caaaagcaca aacaatggcc    540
```

| | |
|---|---|
| ttatttacac aaaaagtctg attttaagat atatgacatt tcaaggtttc agaagtatgt | 600 |
| aatgaggtgt gtctctaatt tttaaatta tatatcttca atttaaagtt ttagttaaaa | 660 |
| cataaagatt aacctttcat tagcaagctg ttagttatca ccaaagcttt tcatggatta | 720 |
| ggaaaaaatc attttgtctc tatgtcaaac atcttggagt tgatatttgg ggaaacacaa | 780 |
| tactcagttg agttccctag gggagaaaag caagcttaag aattgacata agagtagga | 840 |
| agttagctaa tgcaacatat atcactttgt tttttcacaa ctacagtgac tttatgtatt | 900 |
| tcccagagga aggcatacag ggaagaaatt atcccatttg acaaacagc atgttctcac | 960 |
| aggaagcatt tatcacactt acttgtcaac tttctagaat caaatctagt agctgacagt | 1020 |
| accaggatca ggggtgccaa ccctaagcac ccccagaaag ctgactggcc ctgtggttcc | 1080 |
| cactccagac atgatgtcag ctggaccata attaggcttc tgttcttcag agacatttg | 1140 |
| ttcaaagtca tttgggcaac catattctga aaacagccca gccagggtga tggatcactt | 1200 |
| tgcaaagatc ctcaatgagc tattttcaag tgatgacaaa gtgtgaagtt aaccgctcat | 1260 |
| ttgagaactt tcttttcat ccaaagtaaa ttcaaatatg attagaaatc tgaccttta | 1320 |
| ttactggaat tctcttgact aaaagtaaaa ttgaatttta attcctaaat ctccatgtgt | 1380 |
| atacagtact gtgggaacat cacagatttt ggctccatgc cctaaagaga aattggcttt | 1440 |
| cagattattt ggattaaaaa caaagacttt cttaagagat gtaaaatttt catgatgttt | 1500 |
| tcttttttgc taaaactaaa gaattattct tttacatttc agtttttctt gatcatgaaa | 1560 |
| acgccaacaa aattctgaat cggccaaaga ggtataattc aggtaaattg gaagagtttg | 1620 |
| ttcaagggaa ccttgagaga gaatgtatgg aagaaaagtg tagttttgaa gaagcacgag | 1680 |
| aagttttga aaacactgaa agaacaactg aattttggaa gcagtatgtt gatggagatc | 1740 |
| agtgtgagtc caatccatgt ttaaatggcg gcagttgcaa ggatgacatt aattcctatg | 1800 |
| aatgttggtg tccctttgga tttgaaggaa agaactgtga attagatgta acatgtaaca | 1860 |
| ttaagaatgg cagatgcgag cagttttgta aaaatagtgc tgataacaag gtggtttgct | 1920 |
| cctgtactga gggatatcga cttgcagaaa accagaagtc ctgtgaacca gcagtgccat | 1980 |
| ttccatgtgg aagagtttct gtttcacaaa cttctaagct cacccgtgct gaggctgttt | 2040 |
| ttcctgatgt ggactatgta aattctactg aagctgaaac cattttggat aacatcactc | 2100 |
| aaagcaccca atcatttaat gacttcactc gggttgttgg tggagaagat gccaaaccag | 2160 |
| gtcaattccc ttggcaggtt gttttgaatg gtaaagttga tgcattctgt ggaggctcta | 2220 |
| tcgttaatga aaaatggatt gtaactgctg cccactgtgt tgaaactggt gttaaaatta | 2280 |
| cagttgtcgc aggtgaacat aatattgagg agacagaaca tacagagcaa aagcgaaatg | 2340 |
| tgattcgaat tattcctcac cacaactaca atgcagctat aataagtac aaccatgaca | 2400 |
| ttgcccttct ggaactggac gaacccttag tgctaaacag ctacgttaca cctatttgca | 2460 |
| ttgctgacaa ggaatacacg aacatcttcc tcaaatttgg atctggctat gtaagtggct | 2520 |
| ggggaagagt cttccacaaa gggagatcag ctttagttct tcagtaccct agagttccac | 2580 |
| ttgttgaccg agccacatgt cttcgatcta caagttcac catctataac aacatgttct | 2640 |
| gtgctggctt ccatgaagga ggtagagatt catgtcaagg agatagtggg ggaccccatg | 2700 |
| ttactgaagt ggaagggacc agtttcttaa ctggaattat tagctggggt gaagagtgtg | 2760 |
| caatgaaagg caaatatgga atatatacca aggtatcccg gtatgtcaac tggattaagg | 2820 |
| aaaaaacaaa gctcaccggt ggaggcggtt caggcggagg tggctctggc ggtggcggat | 2880 |
| ctggcggagg tggctctggc ggtggcggat ctggcggagg tggctctggc ggtggcggat | 2940 |

```
ctggcggagg tggctctggc ggtggcggat ctggcggagg tggctctggc ggtggcggat    3000
ctggcggagg tggctctggc ggtggcggat ctggcggagg tggctctggc ggtggcggat    3060
ccaccggtga taaaactgtg agatggtgtg cagtgtcgga gcatgaggcc actaagtgcc    3120
agagtttccg cgaccatatg aaaagcgtca ttccatccga tggtcccagt gttgcttgtg    3180
tgaagaaagc ctcctacctt gattgcatca gggccattgc ggcaaacgaa gcggatgctg    3240
tgacactgga tgcaggtttg gtgtatgatg cttacctggc tcccaataac ctgaagcctg    3300
tggtggcaga gttctatggg tcaaaagagg atccacagac tttctattat gctgttgctg    3360
tggtgaagaa ggatagtggc ttccagatga accagcttcg aggcaagaag tcctgccaca    3420
cgggtctagg caggtccgct gggtggaaca tccccatagg cttactttac tgtgacttac    3480
ctgagccacg taaacctctt gagaaagcag tggccaattt cttctcgggc agctgtgccc    3540
cttgtgcgga tgggacggac ttcccccagc tgtgtcaact gtgtccaggg tgtggctgct    3600
ccacccttaa ccaatacttc ggctactcag gagccttcaa gtgtctgaag gatggtgctg    3660
gggatgtggc ctttgtcaag cactcgacta tatttgagaa cttggcaaac aaggctgaca    3720
gggaccagta tgagctgctt tgcctggaca cacccggaa gccggtagat gaatacaagg    3780
actgccactt ggcccaggtc ccttctcata ccgtcgtggc ccgaagtatg ggcggcaagg    3840
aggacttgat ctgggagctt ctcaaccagg cccaggaaca ttttggcaaa gacaaatcaa    3900
aagaattcca actattcagc tctcctcatg ggaaggacct gctgtttaag gactctgccc    3960
acgggttttt aaaagtcccc cccaggatgg atgccaagat gtacctgggc tatgagtatg    4020
tcactgccat ccggaatcta cgggaaggca catgcccaga agccccaaca gatgaatgca    4080
agcctgtgaa gtggtgtgcg ctgagccacc acgagaggct caagtgtgat gagtggagtg    4140
ttaacagtgt agggaaaata gagtgtgtat cagcagagac caccgaagac tgcatcgcca    4200
agatcatgaa tggagaagct gatgccatga gcttggatgg agggtttgtc tacatagcgg    4260
gcaagtgtgg tctggtgcct gtcttggcag aaaactacaa taagagcgat aattgtgagg    4320
atacaccaga ggcagggtat tttgctgtag cagtggtgaa gaaatcagct tctgacctca    4380
cctgggacaa tctgaaaggc aagaagtcct gccatacggc agttggcaga accgctggct    4440
ggaacatccc catgggcctg ctctacaata agatcaacca ctgcagattt gatgaattttt    4500
tcagtgaagg ttgtgcccct gggtctaaga agactccag tctctgtaag ctgtgtatgg    4560
gctcaggcct aaacctgtgt gaacccaaca caaagaggg atactacggc tacacaggcg    4620
cttttcaggtg tctggttgag aagggagatg tggcctttgt gaaacaccag actgtcccac    4680
agaacactgg gggaaaaaac cctgatccat gggctaagaa tctgaatgaa aaagactatg    4740
agttgctgtg ccttgatggt accaggaaac ctgtggagga gtatgcgaac tgccacctgg    4800
ccagagcccc gaatcacgct gtggtcacac ggaaagataa ggaagcttgc gtccacaaga    4860
tattacgtca acagcagcac ctatttggaa gcaacgtaac tgactgctcg ggcaactttt    4920
gtttgttccg gtcggaaacc aaggaccttc tgttcagaga tgacacagta tgttttggcca    4980
aacttcatga cagaaacaca tatgaaaaat acttaggaga agaatatgtc aaggctgttg    5040
gtaacctgag aaaatgctcc acctcatcac tcctggaagc ctgcactttc cgtagacctt    5100
aa                                                                    5102
```

<210> SEQ ID NO 19
<211> LENGTH: 5111
<212> TYPE: DNA

<213> ORGANISM: Artificial Sequence
<220> FEATURE:
<223> OTHER INFORMATION: synthetic construct of gene encoding fusion
      protein FIX(KOI)-GS7-THR-GS7-TF

<400> SEQUENCE: 19

```
gaattcgatt accactttca caatctagcc accatggagc gcgtgaacat gatcatggca      60
gaatcaccag gcctcatcac catctgcctt ttaggatatc tactcagtgc tgaatgtaca     120
ggtttgtttc cttttttaaa atacattgag tatgcttgcc ttttagatat agaaatatct     180
gatgctgtct tcttcactaa attttgatta catgatttga cagcaatatt gaagagtcta     240
acagccagca cgcaggttgg taagtactgg ttctttgtta gctaggtttt cttcttcttc     300
attttttaaaa ctaaatagat cgacaatgct tatgatgcat ttatgtttaa taaacactgt     360
tcagttcatg atttggtcat gtaattcctg ttagaaaaca ttcatctcct tggtttaaaa     420
aaattaaaag tgggaaaaca aagaaatagc agaatatagt gaaaaaaaat aaccacatta     480
tttttgtttg gacttaccac tttgaaatca aatgggaaa caaaagcaca acaatggcc      540
ttatttacac aaaaagtctg attttaagat atatgacatt tcaaggtttc agaagtatgt     600
aatgaggtgt gtctctaatt ttttaaatta tatatcttca atttaaagtt ttagttaaaa     660
cataaagatt aacctttcat tagcaagctg ttagttatca ccaaagcttt tcatggatta     720
ggaaaaaatc attttgtctc tatgtcaaac atcttggagt tgatatttgg ggaaacacaa     780
tactcagttg agttccctag gggagaaaag caagcttaag aattgacata agagtagga      840
agttagctaa tgcaacatat atcactttgt tttttcacaa ctacagtgac tttatgtatt     900
tcccagagga aggcatacag ggaagaaatt atcccatttg acaaacagc atgttctcac      960
aggaagcatt tatcacactt acttgtcaac tttctagaat caaatctagt agctgacagt    1020
accaggatca ggggtgccaa ccctaagcac ccccagaaag ctgactggcc ctgtggttcc    1080
cactccagac atgatgtcag ctggaccata ttaggcttc tgttcttcag agacatttg     1140
ttcaaagtca tttgggcaac catattctga aaacagccca gccagggtga tggatcactt    1200
tgcaaagatc ctcaatgagc tattttcaag tgatgacaaa gtgtgaagtt aaccgctcat    1260
ttgagaactt tctttttcat ccaaagtaaa ttcaaatatg attagaaatc tgaccttta    1320
ttactggaat tctcttgact aaaagtaaaa ttgaatttta attcctaaat ctccatgtgt    1380
atacagtact gtgggaacat cacagatttt ggctccatgc cctaaagaga aattggcttt    1440
cagattattt ggattaaaaa caaagacttt cttaagagat gtaaaattt catgatgttt     1500
tcttttttgc taaaactaaa gaattattct tttacatttc agttttctt gatcatgaaa     1560
acgccaacaa aattctgaat cggccaaaga ggtataattc aggtaaattg gaagagtttg    1620
ttcaagggaa ccttgagaga gaatgtatgg aagaaaagtg tagttttgaa gaagcacgag    1680
aagtttttga aaacactgaa agaacaactg aattttggaa gcagtatgtt gatggagatc    1740
agtgtgagtc caatccatgt ttaaatggcg cagttgcaa ggatgacatt aattcctatg    1800
aatgttggtg tccctttgga tttgaaggaa agaactgtga attagatgta acatgtaaca    1860
ttaagaatgg cagatgcgag cagttttgta aaaatagtgc tgataacaag gtggtttgct    1920
cctgtactga gggatatcga cttgcagaaa accagaagtc ctgtgaacca gcagtgccat    1980
ttccatgtgg aagagtttct gtttcacaaa cttctaagct cacccgtgct gaggctgttt    2040
ttcctgatgt ggactatgta aattctactg aagctgaaac catttggat aacatcactc     2100
aaagcaccca atcatttaat gacttcactc gggttgttgg tggagaagat gccaaaccag    2160
```

```
gtcaattccc ttggcaggtt gttttgaatg gtaaagttga tgcattctgt ggaggctcta    2220
tcgttaatga aaaatggatt gtaactgctg cccactgtgt tgaaactggt gttaaaatta    2280
cagttgtcgc aggtgaacat aatattgagg agacagaaca tacagagcaa aagcgaaatg    2340
tgattcgaat tattcctcac cacaactaca atgcagctat taataagtac aaccatgaca    2400
ttgcccttct ggaactggac gaacccttag tgctaaacag ctacgttaca cctatttgca    2460
ttgctgacaa ggaatacacg aacatcttcc tcaaatttgg atctggctat gtaagtggct    2520
ggggaagagt cttccacaaa gggagatcag ctttagttct tcagtacctt agagttccac    2580
ttgttgaccg agccacatgt cttcgatcta caaagttcac catctataac aacatgttct    2640
gtgctggctt ccatgaagga ggtagagatt catgtcaagg agatagtggg ggaccccatg    2700
ttactgaagt ggaagggacc agtttcttaa ctggaattat tagctggggt gaagagtgtg    2760
caatgaaagg caaatatgga atatatacca aggtatcccg gtatgtcaac tggattaagg    2820
aaaaaacaaa gctcaccggt ggaggcggtt caggcggagg tggctctggc ggtggcggat    2880
ctggcggagg tggctctggc ggtggcggat ctggcggagg tggctctggc ggtggcggat    2940
ctctggtgcc gcgcggatct ggtggaggcg gttcaggcgg aggtggctct ggcggtggcg    3000
gatctggcgg aggtggctct ggcggtggcg gatctggcgg aggtggctct ggcggtggcg    3060
gatccaccgg tgtccctgat aaaactgtga atggtgtgc agtgtcggag catgaggcca    3120
ctaagtgcca gagtttccgc gaccatatga aaagcgtcat tccatccgat ggtcccagtg    3180
ttgcttgtgt gaagaaagcc tcctaccttg attgcatcag ggccattgcg gcaaacgaag    3240
cggatgctgt gacactggat gcaggtttgg tgtatgatgc ttacctggct cccaataacc    3300
tgaagcctgt ggtggcagag ttctatgggt caaaagagga tccacagact ttctattatg    3360
ctgttgctgt ggtgaagaag gatagtggct tccagatgaa ccagcttcga ggcaagaagt    3420
cctgccacac gggtctaggc aggtccgctg ggtggaacat ccccataggc ttactttact    3480
gtgacttacc tgagccacgt aaacctcttg agaaagcagt ggccaatttc ttctcgggca    3540
gctgtgcccc ttgtgcggat gggacggact cccccagct gtgtcaactg tgtccagggt    3600
gtggctgctc cacccttaac caatacttcg gctactcagg agccttcaag tgtctgaagg    3660
atggtgctgg ggatgtggcc tttgtcaagc actcgactat atttgagaac ttggcaaaca    3720
aggctgacag ggaccagtat gagctgcttt gcctggacaa cacccggaag ccggtagatg    3780
aatacaagga ctgccacttg gcccaggtcc cttctcatac cgtcgtggcc cgaagtatgg    3840
gcggcaagga ggacttgatc tgggagcttc tcaaccaggc ccaggaacat tttggcaaag    3900
acaaatcaaa agaattccaa ctattcagct ctcctcatgg gaaggacctg ctgtttaagg    3960
actctgccca cggtttttta aaagtccccc ccaggatgga tgccaagatg tacctgggct    4020
atgagtatgt cactgccatc cggaatctac gggaaggcac atgcccagaa gccccaacag    4080
atgaatgcaa gcctgtgaag tggtgtgcgc tgagccacca cgagaggctc aagtgtgatg    4140
agtggagtgt taacagtgta gggaaaatag agtgtgtatc agcagagacc accgaagact    4200
gcatcgccaa gatcatgaat ggagaagctg atgccatgag cttggatgga gggtttgtct    4260
acatagcggg caagtgtggt ctggtgcctg tcttggcaga aaactacaat aagagcgata    4320
attgtgagga tacaccagag gcagggtatt ttgctgtagc agtggtgaag aaatcagctt    4380
ctgacctcac ctgggacaat ctgaaaggca agaagtcctg ccatacggca gttggcagaa    4440
ccgctggctg gaacatcccc atgggcctgc tctacaataa gatcaaccac tgcagatttg    4500
atgaattttt cagtgaaggt tgtgcccctg ggtctaagaa agactccagt ctctgtaagc    4560
```

```
tgtgtatggg ctcaggccta aacctgtgtg aacccaacaa caaagaggga tactacggct    4620
acacaggcgc tttcaggtgt ctggttgaga agggagatgt ggcctttgtg aaacaccaga    4680
ctgtcccaca gaacactggg ggaaaaaacc ctgatccatg ggctaagaat ctgaatgaaa    4740
aagactatga gttgctgtgc cttgatggta ccaggaaacc tgtggaggag tatgcgaact    4800
gccacctggc cagagccccg aatcacgctg tggtcacacg gaaagataag gaagcttgcg    4860
tccacaagat attacgtcaa cagcagcacc tatttggaag caacgtaact gactgctcgg    4920
gcaacttttg tttgttccgg tcggaaacca aggaccttct gttcagagat gacacagtat    4980
gtttggccaa acttcatgac agaaacacat atgaaaaata cttaggagaa gaatatgtca    5040
aggctgttgg taacctgaga aaatgctcca cctcatcact cctggaagcc tgcactttcc    5100
gtagacctta a                                                         5111

<210> SEQ ID NO 20
<211> LENGTH: 5105
<212> TYPE: DNA
<213> ORGANISM: Artificial Sequence
<220> FEATURE:
<223> OTHER INFORMATION: synthetic construct of gene encoding fusion
      protein FIX(KOI)-GS7-FXa-GS7-TF

<400> SEQUENCE: 20
gaattcgatt accactttca caatctagcc accatggagc gcgtgaacat gatcatggca     60
gaatcaccag gcctcatcac catctgcctt ttaggatatc tactcagtgc tgaatgtaca    120
ggtttgtttc ctttttttaaa atacattgag tatgcttgcc ttttagatat agaaatatct    180
gatgctgtct tcttcactaa attttgatta catgatttga cagcaatatt gaagagtcta    240
acagccagca cgcaggttgg taagtactgg ttctttgtta gctaggtttt cttcttcttc    300
atttttaaaa ctaaatagat cgacaatgct tatgatgcat ttatgtttaa taaacactgt    360
tcagttcatg atttggtcat gtaattcctg ttagaaaaca ttcatctcct tggtttaaaa    420
aaattaaaag tgggaaaaca aagaaatagc agaatatagt gaaaaaaaat aaccacatta    480
tttttgtttg gacttaccac tttgaaatca aatgggaaa caaaagcaca acaatggcc     540 ttatttacac aaaaagtctg attttaagat atatgacatt tcaaggtttc agaagtatgt    600
aatgaggtgt gtctctaatt tttttaaatta tatatcttca atttaaagtt ttagttaaaa    660
cataaagatt aaccttttcat tagcaagctg ttagttatca ccaaagcttt tcatggatta    720
ggaaaaaatc attttgtctc tatgtcaaac atcttggagt tgatatttgg ggaaacacaa    780
tactcagttg agttccctag gggagaaaag caagcttaag aattgacata agagtagga    840 agttagctaa tgcaacatat atcactttgt tttttcacaa ctacagtgac tttatgtatt    900
tcccagagga aggcatacag ggaagaaatt atcccatttg acaaacagc atgttctcac    960 aggaagcatt tatcacactt acttgtcaac tttctagaat caaatctagt agctgacagt    1020
accaggatca ggggtgccaa ccctaagcac ccccagaaag ctgactggcc ctgtggttcc    1080
cactccagac atgatgtcag ctggaccata attaggcttc tgttcttcag gagacatttg    1140
ttcaaagtca tttgggcaac catattctga aaacagccca gccagggtga tggatcactt    1200
tgcaaagatc ctcaatgagc tatttcaag tgatgacaaa gtgtgaagtt aaccgctcat    1260
ttgagaactt tcttttcat ccaaagtaaa ttcaaatatg attagaaatc tgacctttta    1320
ttactggaat tctcttgact aaaagtaaaa ttgaatttta attcctaaat ctccatgtgt    1380
atacagtact gtgggaacat cacagatttt ggctccatgc cctaaagaga aattggcttt    1440
```

```
cagattattt ggattaaaaa caaagacttt cttaagagat gtaaaatttt catgatgttt    1500
tcttttttgc taaaactaaa gaattattct tttacatttc agttttctct gatcatgaaa    1560
acgccaacaa aattctgaat cggccaaaga ggtataattc aggtaaattg aagagtttg     1620 ttcaagggaa ccttgagaga gaatgtatgg aagaaaagtg tagttttgaa gaagcacgag    1680
aagtttttga aaacactgaa agaacaactg aatttggaa gcagtatgtt gatggagatc     1740
agtgtgagtc caatccatgt ttaaatggcg gcagttgcaa ggatgacatt aattcctatg    1800
aatgttggtg tccctttgga tttgaaggaa agaactgtga attagatgta acatgtaaca    1860
ttaagaatgg cagatgcgag cagttttgta aaaatagtgc tgataacaag gtggtttgct    1920
cctgtactga gggatatcga cttgcagaaa accagaagtc ctgtgaacca gcagtgccat    1980
ttccatgtgg aagagtttct gtttcacaaa cttctaagct cacccgtgct gaggctgttt    2040
ttcctgatgt ggactatgta aattctactg aagctgaaac cattttggat aacatcactc    2100
aaagcaccca atcatttaat gacttcactc gggttgttgg tggagaagat gccaaaccag    2160
gtcaattccc ttggcaggtt gttttgaatg gtaaagttga tgcattctgt ggaggctcta    2220
tcgttaatga aaaatggatt gtaactgctg cccactgtgt tgaaactggt gttaaaatta    2280
cagttgtcgc aggtgaacat aatattgagg agacagaaca tacagagcaa aagcgaaatg    2340
tgattcgaat tattcctcac cacaactaca atgcagctat taataagtac aaccatgaca    2400
ttgcccttct ggaactggac gaacccttag tgctaaacag ctacgttaca cctatttgca    2460
ttgctgacaa ggaatacacg aacatcttcc tcaaatttgg atctggctat gtaagtggct    2520
ggggaagagt cttccacaaa gggagatcag ctttagttct tcagtacctt agagttccac    2580
ttgttgaccg agccacatgt cttcgatcta caaagttcac catctataac aacatgttct    2640
gtgctggctt ccatgaagga ggtagagatt catgtcaagg agatagtggg ggaccccatg    2700
ttactgaagt ggaagggacc agtttcttaa ctggaattat tagctggggt gaagagtgtg    2760
caatgaaagg caaatatgga atatatacca aggtatcccg gtatgtcaac tggattaagg    2820
aaaaaacaaa gctcaccggt ggaggcggtt caggcggagg tggctctggc ggtggcggat    2880
ctggcggagg tggctctggc ggtggcggat ctggcggagg tggctctggc ggtggcggat    2940
ctatagaagg ccgaggtgga ggcggttcag gcggaggtgg ctctggcggt ggcggatctg    3000
gcggaggtgg ctctggcggt ggcggatctg gcggaggtgg ctctggcggt ggcggatcca    3060
ccggtgtccc tgataaaact gtgagatggt gtgcagtgtc ggagcatgag gccactaagt    3120
gccagagttt ccgcgaccat atgaaaagcg tcattccatc cgatggtccc agtgttgctt    3180
gtgtgaagaa agcctcctac cttgattgca tcagggccat tgcggcaaac gaagcggatg    3240
ctgtgacact ggatgcaggt ttggtgtatg atgcttacct ggctcccaat aacctgaagc    3300
ctgtggtggc agagttctat gggtcaaaag aggatccaca gactttctat tatgctgttg    3360
ctgtggtgaa gaaggatagt ggcttccaga tgaaccagct cgaggcaag aagtcctgcc     3420 acacgggtct aggcaggtcc gctgggtgga acatccccat aggcttactt tactgtgact    3480
tacctgagcc acgtaaacct cttgagaaag cagtggccaa tttcttctcg ggcagctgtg    3540 cccttgtgc ggatgggacg gacttccccc agctgtgtca actgtgtcca gggtgtggct      3600
gctccaccct taaccaatac ttcggctact caggagcctt caagtgtctg aaggatggtg    3660
ctggggatgt ggcctttgtc aagcactcga ctatatttga gaacttggca acaaggctg      3720 acagggacca gtatgagctg ctttgcctgg acaacacccg gaagccggta gatgaataca    3780
```

```
aggactgcca cttggcccag gtcccttctc ataccgtcgt ggcccgaagt atgggcggca    3840
aggaggactt gatctgggag cttctcaacc aggcccagga acattttggc aaagacaaat    3900
caaaagaatt ccaactattc agctctcctc atgggaagga cctgctgttt aaggactctg    3960
cccacgggtt tttaaaagtc ccccccagga tggatgccaa gatgtacctg ggctatgagt    4020
atgtcactgc catccggaat ctacgggaag gcacatgccc agaagcccca acagatgaat    4080
gcaagcctgt gaagtggtgt gcgctgagcc accacgagag gctcaagtgt gatgagtgga    4140
gtgttaacag tgtagggaaa atagagtgtg tatcagcaga gaccaccgaa gactgcatcg    4200
ccaagatcat gaatgagaa gctgatgcca tgagcttgga tggagggttt gtctacatag    4260
cgggcaagtg tggtctggtg cctgtcttgg cagaaaacta caataagagc gataattgtg    4320
aggatacacc agaggcaggg tattttgctg tagcagtggt gaagaaatca gcttctgacc    4380
tcacctggga caatctgaaa ggcaagaagt cctgccatac ggcagttggc agaaccgctg    4440
gctggaacat cccccatggg ctgctctaca ataagatcaa ccactgcaga tttgatgaat    4500
ttttcagtga aggttgtgcc cctgggtcta agaaagactc cagtctctgt aagctgtgta    4560
tgggctcagg cctaaacctg tgtgaaccca caacaaaga gggatactac ggctacacag    4620
gcgctttcag gtgtctggtt gagaagggag atgtggcctt tgtgaaacac cagactgtcc    4680
cacagaacac tgggggaaaa aaccctgatc catgggctaa gaatctgaat gaaaaagact    4740
atgagttgct gtgccttgat ggtaccagga acctgtgga ggagtatgcg aactgccacc    4800
tggccagagc cccgaatcac gctgtggtca cacggaaaga taaggaagct tgcgtccaca    4860
agatattacg tcaacagcag cacctatttg aagcaacgt aactgactgc tcgggcaact    4920
tttgtttgtt ccggtcggaa accaaggacc ttctgttcag agatgacaca gtatgtttgg    4980
ccaaacttca tgacagaaac acatatgaaa atacttagg agaagaatat gtcaaggctg    5040
ttggtaacct gagaaaatgc tccacctcat cactcctgga agcctgcact tccgtagac    5100
cttaa                                                              5105

<210> SEQ ID NO 21
<211> LENGTH: 5123
<212> TYPE: DNA
<213> ORGANISM: Artificial Sequence
<220> FEATURE:
<223> OTHER INFORMATION: synthetic construct of gene encoding fusion
      protein FIX(KOI)-GS7-FXIa-GS7-TF

<400> SEQUENCE: 21
gaattcgatt accactttca caatctagcc accatggagc gcgtgaacat gatcatggca      60
gaatcaccag gcctcatcac catctgcctt ttaggatatc tactcagtgc tgaatgtaca    120
ggtttgtttc cttttttaaa atacattgag tatgcttgcc ttttagatat agaaatatct    180
gatgctgtct tcttcactaa attttgatta catgatttga cagcaatatt gaagagtcta    240
acagccagca cgcaggttgg taagtactgg ttctttgtta gctaggtttt cttcttcttc    300
attttttaaaa ctaaatagat cgacaatgct tatgatgcat ttatgtttaa taaacactgt    360
tcagttcatg atttggtcat gtaattcctg ttagaaaaca ttcatctcct tggttttaaaa    420
aaattaaaag tgggaaaaca aagaaatagc agaaatagt gaaaaaaat aaccacatta    480
tttttgtttg gacttaccac tttgaaatca aaatgggaaa caaaagcaca acaatggcc    540
ttatttacac aaaaagtctg attttaagat atatgacatt tcaaggtttc agaagtatgt    600
aatgaggtgt gtctctaatt ttttaaatta tatatcttca atttaaagtt ttagttaaaa    660
```

| | |
|---|---|
| cataaagatt aacctttcat tagcaagctg ttagttatca ccaaagctttt tcatggatta | 720 |
| ggaaaaaatc attttgtctc tatgtcaaac atcttggagt tgatatttgg ggaaacacaa | 780 |
| tactcagttg agttccctag gggagaaaag caagcttaag aattgacata aagagtagga | 840 |
| agttagctaa tgcaacatat atcactttgt tttttcacaa ctacagtgac tttatgtatt | 900 |
| tcccagagga aggcatacag ggaagaaatt atcccatttg acaaacagc atgttctcac | 960 |
| aggaagcatt tatcacactt acttgtcaac tttctagaat caaatctagt agctgacagt | 1020 |
| accaggatca ggggtgccaa ccctaagcac ccccagaaag ctgactggcc ctgtggttcc | 1080 |
| cactccagac atgatgtcag ctggaccata attaggcttc tgttcttcag gagacatttg | 1140 |
| ttcaaagtca tttgggcaac catattctga aaacagccca gccagggtga tggatcactt | 1200 |
| tgcaaagatc tcaatgagc tattttcaag tgatgacaaa gtgtgaagtt aaccgctcat | 1260 |
| ttgagaactt tcttttcat ccaaagtaaa ttcaaatatg attagaaatc tgaccttta | 1320 |
| ttactggaat tctcttgact aaaagtaaaa ttgaatttta attcctaaat ctccatgtgt | 1380 |
| atacagtact gtgggaacat cacagatttt ggctccatgc cctaaagaga aattggcttt | 1440 |
| cagattattt ggattaaaaa caaagacttt cttaagagat gtaaaatttt catgatgttt | 1500 |
| tcttttttgc taaaactaaa gaattattct tttacatttc agtttttctt gatcatgaaa | 1560 |
| acgccaacaa aattctgaat cggccaaaga ggtataattc aggtaaattg gaagagtttg | 1620 |
| ttcagggaa ccttgagaga gaatgtatgg aagaaaagtg tagttttgaa gaagcacgag | 1680 |
| aagttttga aaacactgaa agaacaactg aattttggaa gcagtatgtt gatggagatc | 1740 |
| agtgtgagtc caatccatgt ttaaatggcg gcagttgcaa ggatgacatt aattcctatg | 1800 |
| aatgttggtg tccctttgga tttgaaggaa agaactgtga attagatgta acatgtaaca | 1860 |
| ttaagaatgg cagatgcgag cagttttgta aaaatagtgc tgataacaag gtggtttgct | 1920 |
| cctgtactga gggatatcga cttgcagaaa accagaagtc ctgtgaacca gcagtgccat | 1980 |
| ttccatgtgg aagagtttct gtttcacaaa cttctaagct cacccgtgct gaggctgttt | 2040 |
| ttcctgatgt ggactatgta aattctactg aagctgaaac cattttggat aacatcactc | 2100 |
| aaagcaccca atcatttaat gacttcactc gggttgttgg tggagaagat gccaaaccag | 2160 |
| gtcaattccc ttggcaggtt gttttgaatg gtaaagttga tgcattctgt ggaggctcta | 2220 |
| tcgttaatga aaaatggatt gtaactgctg cccactgtgt tgaaactggt gttaaaatta | 2280 |
| cagttgtcgc aggtgaacat aatattgagg agacagaaca tacagagcaa aagcgaaatg | 2340 |
| tgattcgaat tattcctcac cacaactaca atgcagctat taataagtac aaccatgaca | 2400 |
| ttgcccttct ggaactggac gaacccttag tgctaaacag ctacgttaca cctatttgca | 2460 |
| ttgctgacaa ggaatacacg aacatcttcc tcaaatttgg atctggctat gtaagtggct | 2520 |
| ggggaagagt cttccacaaa gggagatcag ctttagttct tcagtacctt agagttccac | 2580 |
| ttgttgaccg agccacatgt cttcgatcta caaagttcac catctataac aacatgttct | 2640 |
| gtgctggctt ccatgaagga ggtagagatt catgtcaagg agatagtggg ggaccccatg | 2700 |
| ttactgaagt ggaagggacc agtttcttaa ctggaattat tagctggggt gaagagtgtg | 2760 |
| caatgaaagg caaatatgga atatatacca aggtatcccg gtatgtcaac tggattaagg | 2820 |
| aaaaaacaaa gctcaccggt ggaggcggtt caggcggagg tggctctggc ggtggcggat | 2880 |
| ctggcggagg tggctctggc ggtggcggat ctggcggagg tggctctggc ggtggcggat | 2940 |
| cttctaagct cacccgtgct gagactgttt ttggtggagg cggttcaggc ggaggtggct | 3000 |
| ctggcggtgg cggatctggc ggaggtggct ctggcggtgg cggatctggc ggaggtggct | 3060 |

```
ctggcggtgg cggatccacc ggtgtccctg ataaaactgt gagatggtgt gcagtgtcgg      3120
agcatgaggc cactaagtgc cagagtttcc gcgaccatat gaaaagcgtc attccatccg      3180
atggtcccag tgttgcttgt gtgaagaaag cctcctacct tgattgcatc agggccattg      3240
cggcaaacga agcggatgct gtgacactgg atgcaggttt ggtgtatgat gcttacctgg      3300
ctcccaataa cctgaagcct gtggtggcag agttctatgg gtcaaaagag gatccacaga      3360 cttttctatta tgctgttgct gtggtgaaga aggatagtgg cttccagatg aaccagcttc      3420
gaggcaagaa gtcctgccac acgggtctag gcaggtccgc tgggtggaac atccccatag      3480
gcttacttta ctgtgactta cctgagccac gtaaacctct tgagaaagca gtggccaatt      3540
tcttctcggg cagctgtgcc ccttgtgcgg atgggacgga cttcccccag ctgtgtcaac      3600
tgtgtccagg gtgtggctgc tccacccta accaatactt cggctactca ggagccttca      3660
agtgtctgaa ggatggtgct ggggatgtgg cctttgtcaa gcactcgact atatttgaga      3720
acttggcaaa caaggctgac agggaccagt atgagctgct tgcctggac aacacccgga      3780 agccggtaga tgaatacaag gactgccact tggcccaggt ccttctcat accgtcgtgg      3840 cccgaagtat gggcggcaag gaggacttga tctgggagct tctcaaccag gcccaggaac      3900
attttggcaa agacaaatca aaagaattcc aactattcag ctctcctcat gggaaggacc      3960
tgctgtttaa ggactctgcc cacgggtttt taaaagtccc ccccaggatg gatgccaaga      4020
tgtacctggg ctatgagtat gtcactgcca tccggaatct acgggaaggc acatgcccag      4080
aagccccaac agatgaatgc aagcctgtga agtggtgtgc gctgagccac cacgagaggc      4140
tcaagtgtga tgagtggagt gttaacagtg tagggaaaat agagtgtgta tcagcagaga      4200
ccaccgaaga ctgcatcgcc aagatcatga atggagaagc tgatgccatg agcttggatg      4260
gagggtttgt ctacatagcg ggcaagtgtg gtctggtgcc tgtcttggca gaaaactaca      4320
ataagagcga taattgtgag gatacaccag aggcagggta ttttgctgta gcagtggtga      4380
agaaatcagc ttctgacctc acctgggaca atctgaaagg caagaagtcc tgccatacgg      4440
cagttggcag aaccgctggc tggaacatcc ccatgggcct gctctacaat aagatcaacc      4500
actgcagatt tgatgaattt ttcagtgaag ttgtgccc tgggtctaag aaaagactcca      4560 gtctctgtaa gctgtgtatg ggctcaggcc taaacctgtg tgaacccaac aacaaagagg      4620
gatactacgg ctacacaggc gctttcaggt gtctggttga aagggagat gtggcctttg      4680 tgaaacacca gactgtccca cagaacactg ggggaaaaaa ccctgatcca tgggctaaga      4740
atctgaatga aaaagactat gagttgctgt gccttgatgg taccaggaaa cctgtggagg      4800
agtatgcgaa ctgccacctg gccagagccc cgaatcacgc tgtggtcaca cggaaagata      4860
aggaagcttg cgtccacaag atattacgtc aacagcagca cctatttgga agcaacgtaa      4920
ctgactgctc gggcaacttt tgtttgttcc ggtcggaaac caaggacctt ctgttcagag      4980
atgacacagt atgtttggcc aaacttcatg acagaaacac atatgaaaaa tacttaggag      5040
aagaatatgt caaggctgtt ggtaacctga gaaaatgctc cacctcatca ctcctggaag      5100
cctgcacttt ccgtagacct taa                                              5123
```

<210> SEQ ID NO 22
<211> LENGTH: 54
<212> TYPE: DNA
<213> ORGANISM: Artificial Sequence
<220> FEATURE:
<223> OTHER INFORMATION: Primer F1

<400> SEQUENCE: 22
accactttca caatctgcta gcagccacca tggagcgcgt gaacatgatc atgg      54

<210> SEQ ID NO 23
<211> LENGTH: 24
<212> TYPE: DNA
<213> ORGANISM: Artificial Sequence
<220> FEATURE:
<223> OTHER INFORMATION: Primer R1

<400> SEQUENCE: 23
gtgattagtt agtgagaggc cctg      24

<210> SEQ ID NO 24
<211> LENGTH: 40
<212> TYPE: DNA
<213> ORGANISM: Artificial Sequence
<220> FEATURE:
<223> OTHER INFORMATION: Primer F2

<400> SEQUENCE: 24
aattggatcc gaattcgatt accactttca caatctagcc      40

<210> SEQ ID NO 25
<211> LENGTH: 40
<212> TYPE: DNA
<213> ORGANISM: Artificial Sequence
<220> FEATURE:
<223> OTHER INFORMATION: Primer R2

<400> SEQUENCE: 25
aattactagt ttaagtgagc tttgtttttt ccttaatcca      40

<210> SEQ ID NO 26
<211> LENGTH: 36
<212> TYPE: DNA
<213> ORGANISM: Artificial Sequence
<220> FEATURE:
<223> OTHER INFORMATION: Primer F3

<400> SEQUENCE: 26
aattgcatgc tgatcatgaa aacgccaaca aaattc      36

<210> SEQ ID NO 27
<211> LENGTH: 30
<212> TYPE: DNA
<213> ORGANISM: Artificial Sequence
<220> FEATURE:
<223> OTHER INFORMATION: Primer F4

<400> SEQUENCE: 27
aattgggccc gaccataatt aggcttctgt      30

<210> SEQ ID NO 28
<211> LENGTH: 30
<212> TYPE: DNA
<213> ORGANISM: Artificial Sequence
<220> FEATURE:
<223> OTHER INFORMATION: Primer R3

<400> SEQUENCE: 28
aattgggccc gaccataatt aggcttctgt      30

<210> SEQ ID NO 29
<211> LENGTH: 34

```
<212> TYPE: DNA
<213> ORGANISM: Artificial Sequence
<220> FEATURE:
<223> OTHER INFORMATION: Primer F5

<400> SEQUENCE: 29
cactccagac atgatgtcag ctgaccataa ttag                           34

<210> SEQ ID NO 30
<211> LENGTH: 39
<212> TYPE: DNA
<213> ORGANISM: Artificial Sequence
<220> FEATURE:
<223> OTHER INFORMATION: Primer F6

<400> SEQUENCE: 30
attgcatgcg aattcgatta ccactttcac aatctagcc                      39

<210> SEQ ID NO 31
<211> LENGTH: 34
<212> TYPE: DNA
<213> ORGANISM: Artificial Sequence
<220> FEATURE:
<223> OTHER INFORMATION: Primer R4

<400> SEQUENCE: 31
aattcagctg acatcatgtc tggagtggga acca                           34

<210> SEQ ID NO 32
<211> LENGTH: 40
<212> TYPE: DNA
<213> ORGANISM: Artificial Sequence
<220> FEATURE:
<223> OTHER INFORMATION: Primer R5

<400> SEQUENCE: 32
aattctcgag ttaagtgagc tttgtttttt ccttaatcca                     40

<210> SEQ ID NO 33
<211> LENGTH: 35
<212> TYPE: DNA
<213> ORGANISM: Artificial Sequence
<220> FEATURE:
<223> OTHER INFORMATION: Primer F7

<400> SEQUENCE: 33
aattagatct gaattcgatt accactttca caatc                          35

<210> SEQ ID NO 34
<211> LENGTH: 44
<212> TYPE: DNA
<213> ORGANISM: Artificial Sequence
<220> FEATURE:
<223> OTHER INFORMATION: Primer R6

<400> SEQUENCE: 34
aattctcgag tctagaaccg gtgagctttg ttttttcctt aatc                44

<210> SEQ ID NO 35
<211> LENGTH: 35
<212> TYPE: DNA
<213> ORGANISM: Artificial Sequence
<220> FEATURE:
<223> OTHER INFORMATION: Primer F8

<400> SEQUENCE: 35
```
ccttcaagtg tctgaaggat ggtgctgggg atgtg                          35

<210> SEQ ID NO 36
<211> LENGTH: 35
<212> TYPE: DNA
<213> ORGANISM: Artificial Sequence
<220> FEATURE:
<223> OTHER INFORMATION: Primer R7

<400> SEQUENCE: 36
cacatcccca gcaccatcct tcagacactt gaagg                          35

<210> SEQ ID NO 37
<211> LENGTH: 35
<212> TYPE: DNA
<213> ORGANISM: Artificial Sequence
<220> FEATURE:
<223> OTHER INFORMATION: Primer F9

<400> SEQUENCE: 37
ggaaggcaca tgcccagaag ccccaacaga tgaat                          35

<210> SEQ ID NO 38
<211> LENGTH: 35
<212> TYPE: DNA
<213> ORGANISM: Artificial Sequence
<220> FEATURE:
<223> OTHER INFORMATION: Primer R8

<400> SEQUENCE: 38
attcatctgt tggggcttct gggcatgtgc cttcc                          35

<210> SEQ ID NO 39
<211> LENGTH: 18
<212> TYPE: DNA
<213> ORGANISM: Artificial Sequence
<220> FEATURE:
<223> OTHER INFORMATION: Primer F10

<400> SEQUENCE: 39
ggactttcca aaatgtcg                                             18

<210> SEQ ID NO 40
<211> LENGTH: 18
<212> TYPE: DNA
<213> ORGANISM: Artificial Sequence
<220> FEATURE:
<223> OTHER INFORMATION: Primer R9

<400> SEQUENCE: 40
tcttgcctcg aagctggt                                             18

<210> SEQ ID NO 41
<211> LENGTH: 18
<212> TYPE: DNA
<213> ORGANISM: Artificial Sequence
<220> FEATURE:
<223> OTHER INFORMATION: Primer F11

<400> SEQUENCE: 41
ggtggcagag ttctatgg                                             18

<210> SEQ ID NO 42
<211> LENGTH: 18
<212> TYPE: DNA
<213> ORGANISM: Artificial Sequence

```
<220> FEATURE:
<223> OTHER INFORMATION: Primer R10

<400> SEQUENCE: 42
cccatgagga gagctgaa                                                 18

<210> SEQ ID NO 43
<211> LENGTH: 18
<212> TYPE: DNA
<213> ORGANISM: Artificial Sequence
<220> FEATURE:
<223> OTHER INFORMATION: Primer F12

<400> SEQUENCE: 43
acaaggactg ccacttgg                                                 18

<210> SEQ ID NO 44
<211> LENGTH: 18
<212> TYPE: DNA
<213> ORGANISM: Artificial Sequence
<220> FEATURE:
<223> OTHER INFORMATION: Primer R11

<400> SEQUENCE: 44
ggtgaggtca gaagctga                                                 18

<210> SEQ ID NO 45
<211> LENGTH: 18
<212> TYPE: DNA
<213> ORGANISM: Artificial Sequence
<220> FEATURE:
<223> OTHER INFORMATION: Primer F13

<400> SEQUENCE: 45
atagcgggca agtgtggt                                                 18

<210> SEQ ID NO 46
<211> LENGTH: 18
<212> TYPE: DNA
<213> ORGANISM: Artificial Sequence
<220> FEATURE:
<223> OTHER INFORMATION: Primer R12

<400> SEQUENCE: 46
cttccaaata ggtgctgc                                                 18

<210> SEQ ID NO 47
<211> LENGTH: 20
<212> TYPE: DNA
<213> ORGANISM: Artificial Sequence
<220> FEATURE:
<223> OTHER INFORMATION: Primer F14

<400> SEQUENCE: 47
gagtatgcga actgccacct                                               20

<210> SEQ ID NO 48
<211> LENGTH: 20
<212> TYPE: DNA
<213> ORGANISM: Artificial Sequence
<220> FEATURE:
<223> OTHER INFORMATION: Primer XL39

<400> SEQUENCE: 48
attaggacaa ggctggtggg                                               20
```

<210> SEQ ID NO 49
<211> LENGTH: 34
<212> TYPE: DNA
<213> ORGANISM: Artificial Sequence
<220> FEATURE:
<223> OTHER INFORMATION: Primer F15

<400> SEQUENCE: 49 ataccggt gataaaactg tgagatggtg tgca                              34

<210> SEQ ID NO 50
<211> LENGTH: 34
<212> TYPE: DNA
<213> ORGANISM: Artificial Sequence
<220> FEATURE:
<223> OTHER INFORMATION: Primer R13

<400> SEQUENCE: 50
aattctcgag ttaaggtcta cggaaagtgc aggc                            34

<210> SEQ ID NO 51
<211> LENGTH: 40
<212> TYPE: DNA
<213> ORGANISM: Artificial Sequence
<220> FEATURE:
<223> OTHER INFORMATION: Primer F16

<400> SEQUENCE: 51
ggtggaggcg gatccgtccc tgataaaact gtgagatggt                      40

<210> SEQ ID NO 52
<211> LENGTH: 34
<212> TYPE: DNA
<213> ORGANISM: Artificial Sequence
<220> FEATURE:
<223> OTHER INFORMATION: Primer F17

<400> SEQUENCE: 52
cctgcgagcc ccatttaccg gtggaggcgg atcc                            34

<210> SEQ ID NO 53
<211> LENGTH: 31
<212> TYPE: DNA
<213> ORGANISM: Artificial Sequence
<220> FEATURE:
<223> OTHER INFORMATION: Primer F18

<400> SEQUENCE: 53
gaggcggttc agtccctgat aaaactgtga g                               31

<210> SEQ ID NO 54
<211> LENGTH: 31
<212> TYPE: DNA
<213> ORGANISM: Artificial Sequence
<220> FEATURE:
<223> OTHER INFORMATION: Primer R14

<400> SEQUENCE: 54
ctcacagttt tatcagggac tgaaccgcct c                               31

<210> SEQ ID NO 55
<211> LENGTH: 35
<212> TYPE: DNA
<213> ORGANISM: Artificial Sequence
<220> FEATURE:
<223> OTHER INFORMATION: Primer F19

<400> SEQUENCE: 55
atgtcttcga tctacagcat tcaccatcta taaca                              35

<210> SEQ ID NO 56
<211> LENGTH: 30
<212> TYPE: DNA
<213> ORGANISM: Artificial Sequence
<220> FEATURE:
<223> OTHER INFORMATION: Primer Oa

<400> SEQUENCE: 56
gatctataga aggccgagga tccaattgtt                                    30

<210> SEQ ID NO 57
<211> LENGTH: 26
<212> TYPE: DNA
<213> ORGANISM: Artificial Sequence
<220> FEATURE:
<223> OTHER INFORMATION: Primer Ob

<400> SEQUENCE: 57
aacaattgga tcctcggcct tctata                                        26

<210> SEQ ID NO 58
<211> LENGTH: 48
<212> TYPE: DNA
<213> ORGANISM: Artificial Sequence
<220> FEATURE:
<223> OTHER INFORMATION: Primer Oc

<400> SEQUENCE: 58
gatcttctaa gctcacccgt gctgagactg tttttggatc caattgtt                48

<210> SEQ ID NO 59
<211> LENGTH: 44
<212> TYPE: DNA
<213> ORGANISM: Artificial Sequence
<220> FEATURE:
<223> OTHER INFORMATION: Primer Od

<400> SEQUENCE: 59
aacaattgga tccaaaaaca gtctcagcac gggtgagctt agaa                    44

<210> SEQ ID NO 60
<211> LENGTH: 31
<212> TYPE: DNA
<213> ORGANISM: Artificial Sequence
<220> FEATURE:
<223> OTHER INFORMATION: Primer F20

<400> SEQUENCE: 60
gtgggatccg atgcacacaa gagtgaggtt g                                  31

<210> SEQ ID NO 61
<211> LENGTH: 35
<212> TYPE: DNA
<213> ORGANISM: Artificial Sequence
<220> FEATURE:
<223> OTHER INFORMATION: Primer R15

<400> SEQUENCE: 61
cacggatccc tataagccta aggcagcttg acttg                              35

<210> SEQ ID NO 62

```
<211> LENGTH: 39
<212> TYPE: DNA
<213> ORGANISM: Artificial Sequence
<220> FEATURE:
<223> OTHER INFORMATION: Primer F21

<400> SEQUENCE: 62
accggtggag gcggaggcgg tgtggatgca cacaagagt                               39

<210> SEQ ID NO 63
<211> LENGTH: 37
<212> TYPE: DNA
<213> ORGANISM: Artificial Sequence
<220> FEATURE:
<223> OTHER INFORMATION: Primer R16

<400> SEQUENCE: 63
aattctcgag ttataagcct aaggcagctt gacttgc                                 37

<210> SEQ ID NO 64
<211> LENGTH: 7
<212> TYPE: PRT
<213> ORGANISM: Artificial Sequence
<220> FEATURE:
<223> OTHER INFORMATION: GS linker G6V

<400> SEQUENCE: 64

Gly Gly Gly Gly Gly Gly Val
1               5
```

FUSION PROTEIN HAVING FACTOR IX ACTIVITY

CROSS REFERENCE TO RELATED APPLICATIONS

This application is a National Stage of International Application No. PCT/KR2011/007795 filed Oct. 19, 2011, claiming priority based on Korean Patent Application No. 10-2010-0102572 filed Oct. 20, 2010, the contents of all of which are incorporated herein by reference in their entirety.

FIELD OF THE INVENTION

The present invention relates to a fusion protein with blood coagulation factor IX (FIX) activity. More particularly, the present invention relates to fusion protein comprising FIX and transferrin which exhibits specific activity twice as high as that of non-fusion, and native FIX, a gene encoding the fusion protein, a recombinant vector comprising the gene, and a host cell comprising the recombinant vector.

BACKGROUND OF THE INVENTION

Hemophilia is a bleeding disorder caused by a hereditary genetic mutation on the X chromosome that leads to a deficiency of a blood coagulation factor. Coagulation is a process of stopping blood loss from a damaged blood vessel wherein the damaged blood vessel wall is covered by a fibrin-containing clot formed through a complex coagulation cascade associated with various coagulation factors. Of the coagulation factors, factor VIII (herein referred to as FVIII) and factor IX (FIX) are associated with the onset of hemophilia A and B, respectively, when they are deficient.

Hemophilia B occurs when FIX is so deficient or inactive that the coagulation cascade for clot formation does not take place. To treat hemophilia B, FIX is administered in various amounts depending on the level of coagulation factors and the type of hemorrhage.

For use in the treatment of hemophilia B, FIX may be typically produced by two methods: purification from human blood; and genetic recombination. A recombinant protein, although producible in a large amount, is poorer in activity and stability than a protein obtained by plasma fractionation.

Various attempts including random mutagenesis, structure-activity relationship comparison, PEGylation, and n-glycosylation have been made on recombinant proteins to overcome the disadvantages, but most of them have failed to achieve special effects.

Transferrin is a blood plasma protein that transports iron through the blood. This plasma protein is the third most abundant in the blood, has a half-life of 8 days, which is relatively long although shorter than that of albumin or immunoglobulin G (IgG), and is featured by receptor-mediated circulation. There have been several fusion proteins that employ transferrin as a fusion partner, but neither the use of transferrin in fusion to FIX nor an effect thereof has been found in any report ever published.

Therefore, the present inventors have endeavored to improve the activity and stability of FIX; and have found that when linked directly or via a linker to transferrin, FIX was notably increased in specific activity and blood stability, compared to non-fused, native FIX, and thus accomplished the present invention.

SUMMARY OF THE INVENTION

Accordingly, it is an object of the present invention to provide a fusion protein that retains the biological activity of native factor IX.

It is another object of the present invention to provide a gene encoding the fusion protein.

It is a further object of the present invention to provide a recombinant vector comprising the gene.

It is a still further object of the present invention to provide a host cell comprising the recombinant vector.

In accordance with an aspect thereof, the present invention provides a fusion protein comprising human-derived factor IX (FIX) and human-derived transferrin.

In accordance with another aspect thereof, the present invention provides a gene encoding the fusion protein.

In accordance with a further aspect thereof, the present invention provides a recombinant vector comprising the gene.

In accordance with a still further aspect thereof, the present invention provides a host cell comprising the recombinant vector therein.

BRIEF DESCRIPTION OF THE DRAWINGS

The above and other objects and features of the present invention will become apparent from following description of the invention, when taken in conjunction with the accompanying drawings, which respectively show:

FIG. 1b: a schematic view illustrating the structure of intron 1 and the process of constructing fragment B;

FIG. 8b: a graph showing the specific FIX activity calculated on the basis of the results of FIG. 8a;

FIG. 8d: a graph showing specific FIX activities calculated on the basis of the results of FIG. 8c.

DETAILED DESCRIPTION OF THE INVENTION

Figure 1A:
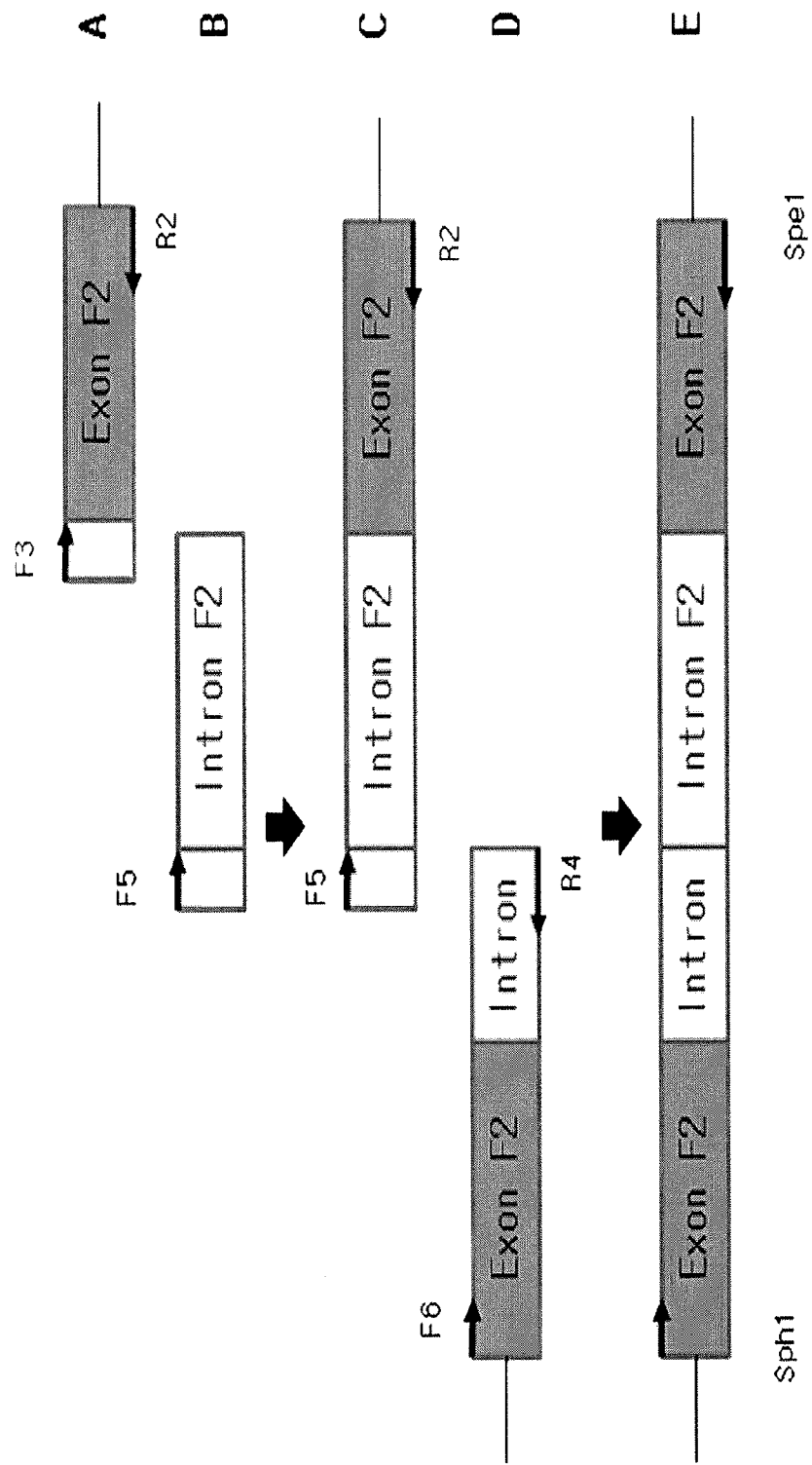
FIG. 1a: a schematic view illustrating the process of constructing a FIX fragment using overlapping PCR.

Hereinafter, the present invention is described in detail.

The present invention provides a fusion protein comprising factor IX (FIX) and transferrin.

The FIX and the transferrin employed in the fusion protein of the present invention may be derived from any mammal, and preferably from humans. More preferably, the FIX and the transferrin share a homology of 95% or higher with their respective native proteins. Most preferably, the FIX and the transferrin have amino sequences represented by SEQ ID NOS: 1 and 2, respectively.

In one embodiment of the present invention, the fusion protein may comprise functional equivalents or derivatives of the FIX and transferrin. "Functional equivalents" may have one or more amino acid deletions, insertions, non-conserved or conserved substitutions, or combinations thereof on the amino acid sequences of SEQ ID NOS: 1 and 2, it being possible for said mutations to occur in any sequence position as long as they result in no substantial alterations of the active site or domain responsible for the biological activity of FIX.

Depending on the situation, the fusion protein of the present invention may undergo such modifications so as to increase or decrease physical and chemical properties thereof, such as phosphorylation, sulfation, acrylation, glycosylation, methylation, farnesylation, acetylation, amidation, etc. So long as they retain the substantial biological activity of FIX, the modified fusion proteins fall within the scope of the present invention.

In the fusion protein of the present invention, the N-terminus of transferrin may be coupled to the C-terminus of FIX.

Alternatively, the fusion protein of the present invention may further comprise a linker between FIX and transferrin. That is, the C-terminus of FIX may be coupled through the linker to the N-terminus of transferrin.

Acting to minimize potential interference between the two fusion partners, the linker can increase the activity of FIX of the fusion protein. The linker is preferably a peptide ranging in length from 1 to 100 amino acids, but is not limited to the length. So long as it separates FIX from transferrin in the fusion protein, any peptide may be employed as a linker in the present invention. Although no particular limitations are imparted to the amino acid sequence of the linker, it may preferably comprise glycine (G) and serine (S) residues in a repetitive or random pattern. For example, the linker may preferably comprise the amino acid sequence of (GGGGS)$_N$ (SEQ ID NO: 3) (wherein N is an integer of 1 or higher, preferably, 1 to 20), and more preferably the amino acid sequence of SEQ ID NO: 3 or 4 (see Table 2).

Moreover, the linker may have a cleavage site that can be recognized and digested by proteases, which are abundantly found in damaged tissue. The digestion site may be recognized by a protease selected from the group consisting of thrombin, factor Xa, and factor XIa. At a working site, the fusion protein comprising the linker with such a protease digestion site is divided into the fusion partners, FIX and transferrin, which can perform their respective functions. Preferably, the linker has any one of amino acid sequences of SEQ ID NOS: 5 to 11 (see Table 2).

The FIX-transferrin fusion protein according to the present invention has a specific FIX activity at least 1.5-times as high as that of non-fusion, native FIX. In one embodiment, the fusion protein of the present invention was found to exhibit a specific FIX activity of about 0.5- to 2-fold larger, compared to non-fusion, native FIX (see Tables 3-1 and 3-2, and FIGS. 7B and 7D).

In accordance with another aspect thereof, the present invention provides a gene encoding the fusion protein.

The gene encoding the fusion protein of the present invention may have various modifications made in the encoding region within the extent that they do not change the amino acid sequence of the fusion protein, due to codon degeneracy or in consideration of the codons preferred by the organism in which they are to be expressed, and various modifications or alterations may be introduced even in regions other than the coding region so long as they have no influence on the expression of the gene. The mutant genes also fall within the scope of the present invention.

Preferably, the gene may comprise a part of the intron of FIX to increase the expression of FIX. More preferably, the gene may contain a 981 bp sequence of the 5'-end region of FIX intron 1 and a 443 bp sequence of the 3'-end region of FIX intron 1, both inserted at the site of $88^{th}$ base in FIX exon 1.

In one embodiment, the gene of the present invention may comprise a gene coding for the linker.

In the present invention, the gene encoding the fusion protein preferably has the nucleotide sequence of one of SEQ ID NOS: 12 to 21. The gene encoding the fusion protein in accordance with the present invention may be carried by an expression vector.

Thus, the present invention provides a recombinant expression vector comprising the gene encoding the fusion protein.

As used herein, the term "vector" refers to a vehicle for introducing a DNA encoding the fusion protein into a host cell and expressing the fusion protein in the host cell. Conventional vectors including plasmid vectors, cosmid vectors, bacteriophage vectors, and viral vectors may be employed, with preference for plasmid vectors.

A suitable expression vector may be constructed in such a way to encompass a signal sequence for membrane targeting or secretion or a leader sequence as well as regulatory sequences such as a promoter, an operator, an initiation codon, a termination codon, a polyadenylation signal, an enhancer, etc., depending on the purpose. When the genetic construct is applied, the initiation codon and the termination codon must work and be present in-frame with the coding sequence. In addition, the expression vector may comprise a selection marker for selecting host cells transformed with the expression vector and a replication origin in case of a replicable expression vector. The vector can replicate by itself or can be incorporated into a chromosome of the host cell.

In detail, the recombinant expression vector according to the present invention may be constructed by inserting a gene encoding the fusion protein into a pcDNA3.1-hygro vector.

Also, the present invention provides a host cell, transformed with the recombinant expression vector, for expressing the fusion protein.

Since host cells differ in expression level and protein modification from one to another, it is important to select host cells most suitable for the purpose of the present invention. Examples of the host cells useful in the present invention include Chinese hamster ovary (CHO) cells, human embryonic kidney cells (HEK293), baby hamster kidney cells (BHK-21), and the human hepatic carcinoma cell line (HepG2), but are not limited thereto.

The recombinant expression vector of the present invention can be introduced into host cells using conventional techniques known in the art, examples of which include electroporation, protoplast fusion, calcium phosphate ($CaPO_4$) co-precipitation, and calcium chloride ($CaCl_2$) precipitation, but are not limited thereto.

The fusion protein with FIX activity in accordance with the present invention exhibits higher biological activity of FIX than that of native FIX, and thus can be usefully applied to the therapy of FIX deficiency-associated diseases.

The following Examples are intended to further illustrate the present invention without limiting its scope.

Hereinafter, the present invention is described more specifically by the following examples, but these are provided only for illustration purposes and the present invention is not limited thereto.

Example 1

Construction of FIX Expression Vector

For use in constructing a FIX expression vector, as shown in FIG. 1A, a polynucleotide fragment E encoding a FIX protein was prepared. The fragment E was generated by inserting parts of a FIX intron into a FIX exon to increase the expression efficiency of FIX. In this regard, respective 981 and 443 bp sequences of 5'- and 3'-end regions of FIX intron 1 were inserted at the site of $88^{th}$ base in FIX exon 1 (JBC, vol. 270, pp. 5276-5281). A detailed description of the procedure will be given below.

<1-1> Generation of Fragment A

The FIX (Kozak+ORF) was inserted into a pcDNA3.1/Hygro/lacZ vector (Invitrogen) to give a recombinant vector, named pcDNA3.1 FIX pDNA. Specifically, a sense primer (F1, SEQ ID NO: 22) containing the Kozak sequence (gccaccatggag) and an antisense primer (R1, SEQ ID NO: 23) were synthesized and used for PCR in HepG2 to give FIX (kozak+ORF). The PCR was performed in the presence of pfu turbo DNA polymerase (Invitrogen, 2.5 unit/μL #600252) with 30 cycles of annealing at 56° C. and extension at 68° C. for 3 min. The PCR product thus obtained was cloned into pGEM T-easy vector (Promega, Madison, Wis., Cat. No. A1360) for base sequencing. While this vector served as a template, a FIX (kozak+ORF) insert was amplified by PCR using a sense primer (F2, SEQ ID NO: 24) and an antisense primer (R2, SEQ ID NO: 25). The PCR was performed in the presence of pfu turbo DNA polymerase (Invitrogen, 2.5 unit/μL #600252), with 30 cycles of annealing at 58° C. and extension at 68° C. for 3 min. After digestion with BamHI/SpeI, the insert was ligated to pcDNA3.1/Hygro/lacZ which was previously treated with BamHI/XbaI, using T4 DNA ligase (Takara, #2011A) to yield a recombinant expression vector, named "pcDNA3.1-hygro-FIX(KOI)."

While pcDNA3.1 FIX pDNA served as a template, the fragment A of FIG. 1a was amplified by PCR using a sense primer (F3, SEQ ID NO: 26) and an antisense primer (R2, SEQ ID NO: 25) in the presence of pfu turbo DNA polymerase (Invitrogen, 2.5 unit/μL #600252). The PCR was performed in the presence of pfu turbo DNA polymerase (Invitrogen, 2.5 unit/μL #600252) with 30 cycles of annealing at 58° C. and extension at 68° C. for 2 min.

<1-2> Generation of Fragment B

According to the procedure illustrated in FIG. 1b, fragment B (composed of "a part of intron F1+intron F2") of FIG. 1b was generated from intron 1 (composed of "intron F1+X+intron F2") of FIX. Specifically, PCR was performed on HEK 293 genomic DNA using a sense primer (F4, SEQ ID NO: 27) and an antisense primer (R3, SEQ ID NO: 28) in the presence of pfu turbo DNA polymerase (Invitrogen, 2.5 unit/μL #600252), with 30 cycles of annealing at 58° C. and extension at 68° C. for 2 min to give an intron F2 PCR product. While this intron F2 PCR product served as a template, PCR was performed in the presence of pfu turbo DNA polymerase (Invitrogen, 2.5 unit/μL #600252) using a sense primer (F5, SEQ ID NO: 29) and an antisense primer (R3, SEQ ID NO: 28), with 30 cycles of annealing at 58° C. and extension at 68° C. for 2 min to yield fragment B consisting of a part of intron F1, and intron F2.

<1-3> Generation of Fragment C

Fragment C consisting of a part of intron F1, intron F2, and exon F2 was amplified from fragments A and B, obtained respectively in Examples <1-1> and <1-2>, by PCR using a sense primer (F5, SEQ ID NO: 29) and an antisense primer (R2, SEQ ID NO: 25) in the presence of pfu turbo DNA polymerase (Invitrogen, 2.5 unit/μL #600252). The PCR was performed using pfu turbo DNA polymerase (Invitrogen, 2.5 unit/μL #600252) with 30 cycles of annealing at 58° C. and extension at 68° C. for 3 min.

<1-4> Generation of Fragment D

Fragment D consisting of exon F1 and intron F1 was amplified from HEK 293 genome DNA by PCR using a sense primer (F6, SEQ ID NO: 30) and an antisense primer (R4, SEQ ID NO: 31). The PCR was performed in the presence of pfu turbo DNA polymerase (Invitrogen, 2.5 unit/μL #600252) with 30 cycles of annealing at 58° C. and extension at 68° C. for 2 min.

<1-5> Generation of Fragment E

Fragment E was amplified from fragments C and D, obtained respectively in Examples <1-3> and <1-4>, by PCR using a sense primer (F6; SEQ ID NO: 30) and an antisense primer (R2; SEQ ID NO: 25) in the presence of pfu turbo DNA polymerase (Invitrogen, 2.5 unit/μL #600252). The PCR was performed with 30 cycles of annealing at 58° C. and extension at 68° C. for 3 min. The PCR product was cloned into a pGEM T-easy vector (Promega, Madison, Wis., Cat. No. A1360) and subjected to base sequencing. The fragment E was composed of the Kozak sequence, an ORF, and a part of intron1, and was named "FIX(KOI)."

<1-6> Construction of Expression Vector

After starting at 98° C. for 30 sec for denaturation, PCR was performed on FIX(KOI) obtained in Example <1-5> using a sense primer (F2, SEQ ID NO: 24) and an antisense primer (R5, SEQ ID NO: 32) in the presence of Phusion® High-Fidelity DNA polymerase (Finnzyme, 2 units/μL, #F-530S), with 30 thermal cycles of 98° C. for 10 sec, 58° C. for 45 sec, and 72° C. for 2 min, followed by final extension at 72° C. for 7 min. The PCR product thus obtained was treated with BamHI and XhoI, and then ligated to pcDNA3.1/hygro vector previously digested with the same enzymes, using T4 DNA ligase (Takara, #2011A) to construct the recombinant expression vector "pcDNA3.1-hygro-FIX(KOI)."

Primers used in PCR for the construction of the FIX(KOI) expression vector are summarized in Table 1, below.

TABLE 1

| Primer | Sequence | SEQ ID NO: |
|---|---|---|
| <1-1> Generation of Fragment A | | |
| F1 | ACCACTTTCACAATCTGCTAGCAGCCACCATGGAGCGCGTGAACATGATCATGG | 22 |
| R1 | GTGATTAGTTAGTGAGAGGCCCTG | 23 |
| F2 | AATTGGATCCGAATTCGATTACCACTTTCACAATCTAGCC | 24 |
| R2 | AATTACTAGTTTAAGTGAGCTTTGTTTTTTCCTTAATCCA | 25 |
| F3 | AATTGCATGCTGATCATGAAAACGCCAACAAAATTC | 26 |
| R2 | AATTACTAGTTTAAGTGAGCTTTGTTTTTTCCTTAATCCA | 25 |
| <1-2> Generation of Fragment B | | |
| F4 | AATTGGGCCCGACCATAATTAGGCTTCTGT | 27 |
| R3 | AATTTGATCAAGAAAAACTGAAATGTAAAAGAATAATTC | 28 |
| F5 | CACTCCAGACATGATGTCAGCTGACCATAATTAG | 29 |
| R3 | AATTTGATCAAGAAAAACTGAAATGTAAAAGAATAATTC | 28 |
| <1-3> Generation of Fragment C | | |
| F5 | CACTCCAGACATGATGTCAGCTGACCATAATTAG | 29 |
| R2 | AATTACTAGTTTAAGTGAGCTTTGTTTTTTCCTTAATCCA | 25 |
| <1-4> Generation of Fragment D | | |
| F6 | AATTGCATGCGAATTCGATTACCACTTTCACAATCTAGCC | 30 |
| R4 | AATTCAGCTGACATCATGTCTGGAGTGGGAACCA | 31 |
| <1-5> Generation of Fragment E | | |
| F6 | AATTGCATGCGAATTCGATTACCACTTTCACAATCTAGCC | 30 |
| R2 | AATTACTAGTTTAAGTGAGCTTTGTTTTTTCCTTAATCCA | 25 |
| <1-6> Construction of Expression Vector | | |
| F2 | AATTGGATCCGAATTCGATTACCACTTTCACAATCTAGCC | 24 |
| R5 | AATTCTCGAGTTAAGTGAGCTTTGTTTTTTCCTTAATCCA | 32 |

Example 2

Construction of FIX(KOI)-Tf Expression Vector (pcDNA3.1-hygro-FIX(KOI)-Tf)

A vector capable of expressing a fusion protein in which FIX(KOI) was linked to human transferrin (Tf) was constructed.

Figure 2:
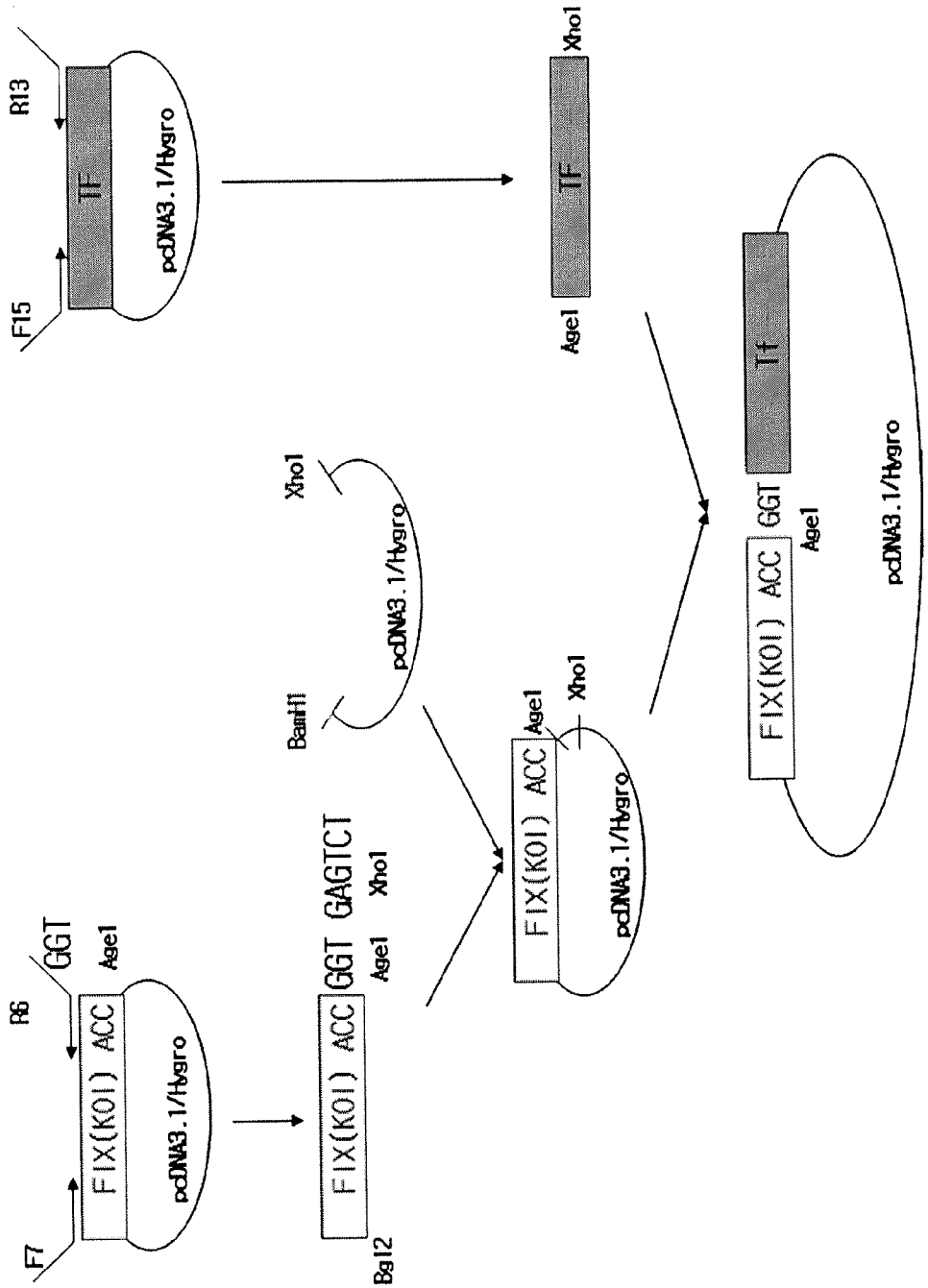
FIG. 2: a schematic view illustrating the process of constructing a FIX-Tf expression vector from vectors which carry a FIX(KOI)-encoding cDNA and a transferrin (Tf)-encoding cDNA, respectively.

The construction of the expression vector is schematically illustrated in FIG. 2. For this, a FIX(KOI) fragment was amplified by PCR using the pcDNA3.1-hygro-FIX(KOI) expression vector obtained in Example 1 as a template. For PCR, in order to eliminate the stop codon from FIX(KOI) and insert various sizes of a linker between FIX(KOI) and Tf, a sense primer (F7; SEQ ID NO: 33) containing a BglII site which is translatable into threonine (Thr) and glycine (Gly), and an antisense primer (R6; SEQ ID NO: 34) which eliminates a stop codon, both based on a sequence containing an AgeI (ACCGGT) and XhoI site (GAGTCT), were synthesized. Phusion® High-Fidelity DNA polymerase (Finnzyme, 2 units/μL, #F-530S) was employed as PCR polymerase. A PCR mix (a total of 50 μL, 1 μL vector template, 2 μL primers F7 and R6 (each 10 pmol/μL), 10 μL 5× Phusion® HF buffer, 1 μL dNTP, 0.5 μL Phusion® DNA polymerase, and 35.5 μL water) was subjected to a reaction at 98° C. for 30 sec, then 30 cycles of 98° C. for 10 sec, 58° C. for 45 sec, and 72° C. for 2 min, followed by 72° C. for 7 min. The amplified PCR product (FIX(KOI)-AgeI-XhoI) was digested with BglII and XhoI at 37° C. and then cloned into a pcDNA3.1/Hygro vector previously treated with BamHI and XhoI.

Separately, in order to obtain human transferring (Tf), the recombinant vector pCMV6-NEO carrying human transferrin (Tf) was prepared. Specifically, a cDNA for human C-type transferrin (GenBank accession No. NM_001063.2) was purchased from Origene (Cat #: SC322130), and found to have mutations GAT→AAT(Asp197Asn) and CCA→CAA(Pro332Gln) as analyzed by base sequencing. This mutant sequence was restored by PCR-based mutagenesis using mutagenic primers F8, R7, F9, and R8 (SEQ ID NOS: 35 to 38). In this PCR, a PCR mix (a total of 20 μL, 1 μL human cDNA clone-containing plasmid DNA (Origene, Cat #: SC322130), 1 μL F8 or R7 primer (10 μM), 1 μL F9 or R8 primer (10 μM), 0.4 μL dNTP (10 mM), 2 μL 10×Pfu turbo PCR buffer (Stratagene), 14.2 μL distilled water, and 0.4 μL Pfu turbo DNA polymerase (Stratagene, #600252, 2.5 units/μL)) was reacted at 94° C. for 5 min, and subjected to 17 cycles of 94° C. for 30 sec, 58° C. for 1 min, and 72° C. for 10.5 min, followed by the final treatment at 72° C. for 7 min. The PCR product was digested with the restriction enzyme DpnI (NEB, #R0176S) at 37° C. for 1 hr to remove unmutated plasmid templates. The recombinant vector thus constructed was amplified in E. coli (HIT competent cell, DH5α, #RH617), followed by selection by mini-preparation and restriction digestion. The selected positive clones were sequenced using F10, R9, F11, R10, F12, R11, F13, R12, F14 and Primer XL39 (Origene) (SEQ ID NOS: 39 to 48). As a result, the mutation in the coding region was restored, and the clone was found to have a nucleotide sequence completely identical to human transferrin cDNA (GenBank accession #: NM_001063.2). PCR was performed on the human transferrin cDNA using a sense primer (F15, SEQ ID NO: 49), and an antisense primer (R13, SEQ ID NO: 50) in the presence of Phusion® High-Fidelity DNA polymerase (Finnzyme, 2 units/μL, #F-530S) under the same condition as in the FIX(KOI) PCR with the exception that the primers F15 and R13 (each 20 pmol) were employed. The amplified PCR product (Tf) was treated with AgeI and XhoI at 37° C., and ligated to pcDNA3.1/hygro vector treated previously with the same restriction enzymes, using DNA ligase (Takara, #2011A) to afford the recombinant expression vector FIX(KOI)-Tf.

Example 3

Construction of FIX(KOI)-GS-Tf Expression Vector

A recombinant vector for expressing a fusion protein in which FIX(KOI) was coupled to Tf through a linker was constructed. The linker was made of one or more repeating units composed of four glycine residues and one serine residue, i.e., GGGGS (SEQ ID NO: 3), and was named "GS linker." GS1 (or 1 GS), GS2 (or 2 GS), GS3 (or 3 GS), and GS4 (or 4 GS) represent GS linkers containing one, two, three, and four repeating units, respectively. In this Example, GS1, GS7, and GS15 linkers were used.

<3-1> Construction of FIX(KOI)-GS1-Tf Expression Vector (pcDNA3.1-hygro-FIX(KOI)-GS1-Tf)

Figure 3:
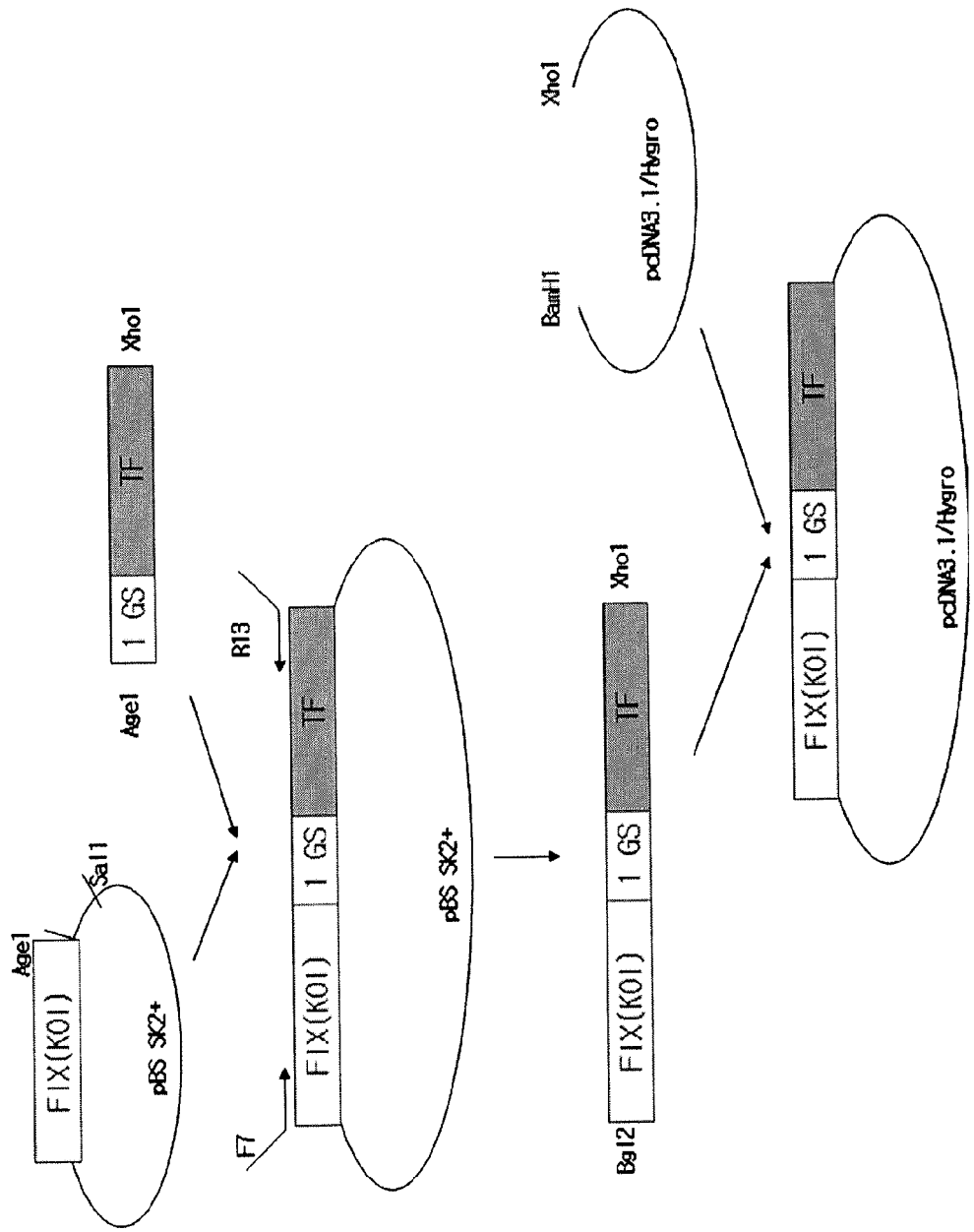
FIG. 3: a schematic view illustrating the process of constructing a FIX(KOI)-GS1-Tf expression vector.

A vector capable of expressing a fusion protein in which FIX(KOI) was coupled to Tf through GS1 linker was constructed as follows. The construction procedure is schematically illustrated in FIG. 3.

Specifically, the connection of Tf to GS-1 linker was achieved by PCR using F16 (SEQ ID NO: 51) and R13 (SEQ ID NO: 50) primers. PCR was allowed to start with reaction at 98° C. for 30 sec in the presence of Phusion® High-Fidelity DNA polymerase (Finnzyme, 2 units/μL, #F-530S) and proceed with 30 thermal cycles of 98° C. for 10 sec, 58° C. for 45 sec, and 72° C. for 2 min, followed by the final thermal treatment at 72° C. for 7 min. From the PCR product, a GS1-Tf fragment was amplified by PCR using a sense primer (F17, SEQ ID NO: 52) and an antisense primer (R13, SEQ ID NO: 50) in the presence of Phusion® High-Fidelity DNA polymerase (Finnzyme, 2 units/μL, #F-530S). The PCR condition was the same as in the Tf PCR condition of Example 2. The resulting PCR product (GS1-Tf) was treated with AgeI and XhoI at 37° C. while a FIX(KOI)-cloned pBluescript SKII+ vector was digested with AgeI and SalI, and the PCR product thus obtained was ligated to the resulting pBluescript SKII+ vector using T4 DNA ligase (Takara, #2011A). The FIX(KOI)-cloned pBluescript SKII+ was constructed as follows. A FIX PCR product free of a stop codon (FIX(KOI)-AgeI-XhoI) was prepared in the same manner as in Example 2, treated with the restriction enzyme BamHI, and ligated to the BamHI/EcoRV-treated pBluescript SKII+ using T4 DNA ligase (Takara, #2011A).

A FIX(KOI)-GS1-Tf fragment was inserted into pcDNA3.1/hygro vector as follows. First, PCR was performed by employing the above constructed vector as a template, a sense primer (F7; SEQ ID NO: 33), and an antisense primer (R13; SEQ ID NO: 50) in the presence of Phusion® High-Fidelity DNA polymerase (Finnzyme, 2 units/μL, #F-530S) under the same condition as in the Tf PCR condition of Example 2, with the exception of using the primers F7 and R13 (each 20 pmol), to amplify the FIX (KOI)-GS1-Tf fragment. This PCR product (FIX(KOI)-GS1-Tf) was digested with BglII and XhoI at 37° C. for 2 hrs while the pcDNA3.1/Hygro vector was treated with BamHI and XhoI, and the FIX(KOI)-GS1-Tf fragment was ligated to the resulting vector using T4 DNA ligase (Takara, #2011A) to construct a FIX(KOI)-Tf expression vector.

<3-2> Construction of FIX(KOI)-G515-Tf Expression Vector (pcDNA3.1-hygro-FIX(KOI)-GS15-Tf)

Figure 4:
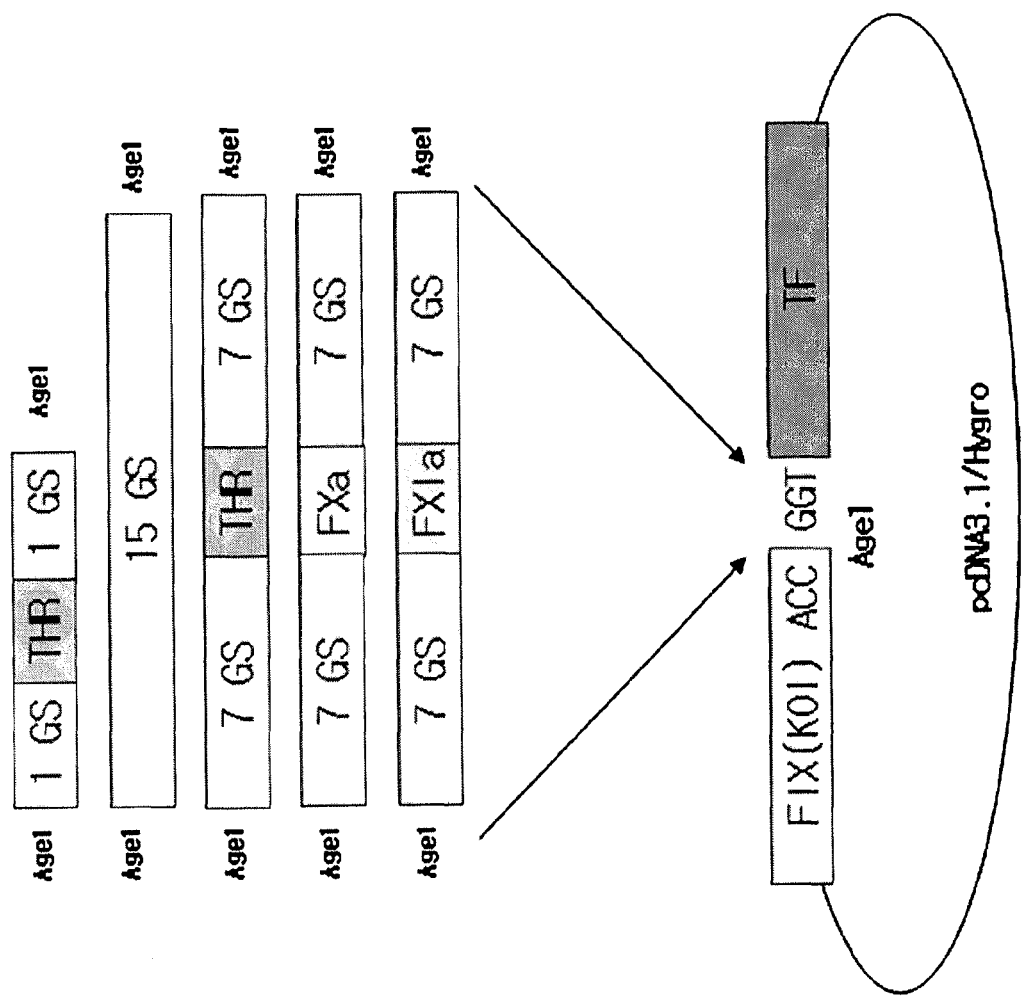
FIG. 4: a schematic view illustrating the process of constructing FIX(KOI)-GS1-THR-GS1-Tf, FIX(KOI)-GS15-Tf, FIX (KOI)-GS7-THR-GS7-Tf, FIX(KOI)-GS7-FXa-GS7-Tf, and FIX(KOI)-GS7-FXIa-GS7-Tf expression vectors.

A vector capable of expressing a fusion protein in which FIX(KOI) was coupled to Tf through GS15 linker was constructed as illustrated in FIG. 4.

Specifically, a GS15 linker-subcloned vector was treated with AgeI to obtain a GS15 linker fragment. Separately, the FIX(KOI)-Tf expression vector prepared in Example 2 was treated with the same restriction vector, followed by ligating the GS15 linker fragment thereinto in the presence of T4 DNA ligase (Takara, #2011A) to construct a FIX(KOI)-GS15-Tf expression vector.

Example 4

Construction of FIX(KOI)-Tf Expression Vector Containing GS Linker with Thrombin Digestion Site <4-1> Construction of FIX(KOI)-GS1-THR-GS1-Tf Expression Vector (pcDNA3.1-hygro-FIX(KOI)-GS1-THR-GS1-Tf)

A FIX(KOI)-Tf expression vector containing GS1 and a thrombin digesting site (THR) was constructed as illustrated in FIG. 4.

Specifically, a GS1-THR-GS1-subcloned vector (SK Chemical) was digested with AgeI at 37° C. to obtain a GS1-THR-GS1 fragment while the FIX(KOI)-Tf expression vector prepared in Example 2 was treated with the same restriction enzyme, followed by ligation using T4 DNA ligase to prepare a FIX(KOI)-GS1-THR-GS1-Tf expression vector.

<4-2> Construction of FIX(KOI)-G57-THR-G57-Tf Expression Vector (pcDNA3.1-hygro-FIX(KOI)-G57-THR-G57-Tf)

A FIX(KOI)-Tf expression vector containing two GS7 linkers with a thrombin cleavage site (THR) located therebetween was constructed as illustrated in FIG. 4.

Specifically, a GS7-THR-GS7-subcloned vector (SK Chemical) was digested with AgeI at 37° C. to obtain a GS7-THR-GS7 fragment while the FIX(KOI)-Tf expression vector prepared in Example 2 was treated with the same restriction enzyme, followed by ligation using T4 DNA ligase to prepare a FIX(KOI)-G57-THR-G57-Tf expression vector.

<4-3> Construction of FIX(KOI)-GS1-THR-GS1-del-Tf Expression Vector (pcDNA3.1-hygro-FIX(KOI)-GS1-THR-GS1-del-Tf)

From the expression vector containing GS1 and a thrombin digesting site (THR), prepared in Example 4-1, the AgeI restriction site through which the linker was coupled with Tf was removed.

Specifically, PCR-based mutagenesis described in Example 2 was carried out to remove an AgeI restriction site from the FIX(KOI)-GS1-THR-GS1-Tf expression vector prepared in Example <4-1>. The vector synthesized using mutagenic primers F18 and R14 (SEQ ID NOS: 53 and 54) was amplified in *E. coli* (HIT competent cell, DH5α, #RH617), followed by selection by mini-preparation and restriction digestion. The selected clone was identified to be free of the AgeI restriction site as analyzed by base sequencing using primer F19 (SEQ ID NO: 55).

Example 5

Construction of FIX(KOI)-Tf Expression Vector Containing GS Linker with FXa Cleavage Site <5-1> Construction of FIX(KOI)-GS1-FXa-Tf Expression Vector (pcDNA3.1-hygro-FIX(KOI)-GS1-FXa-Tf)

Figure 5:
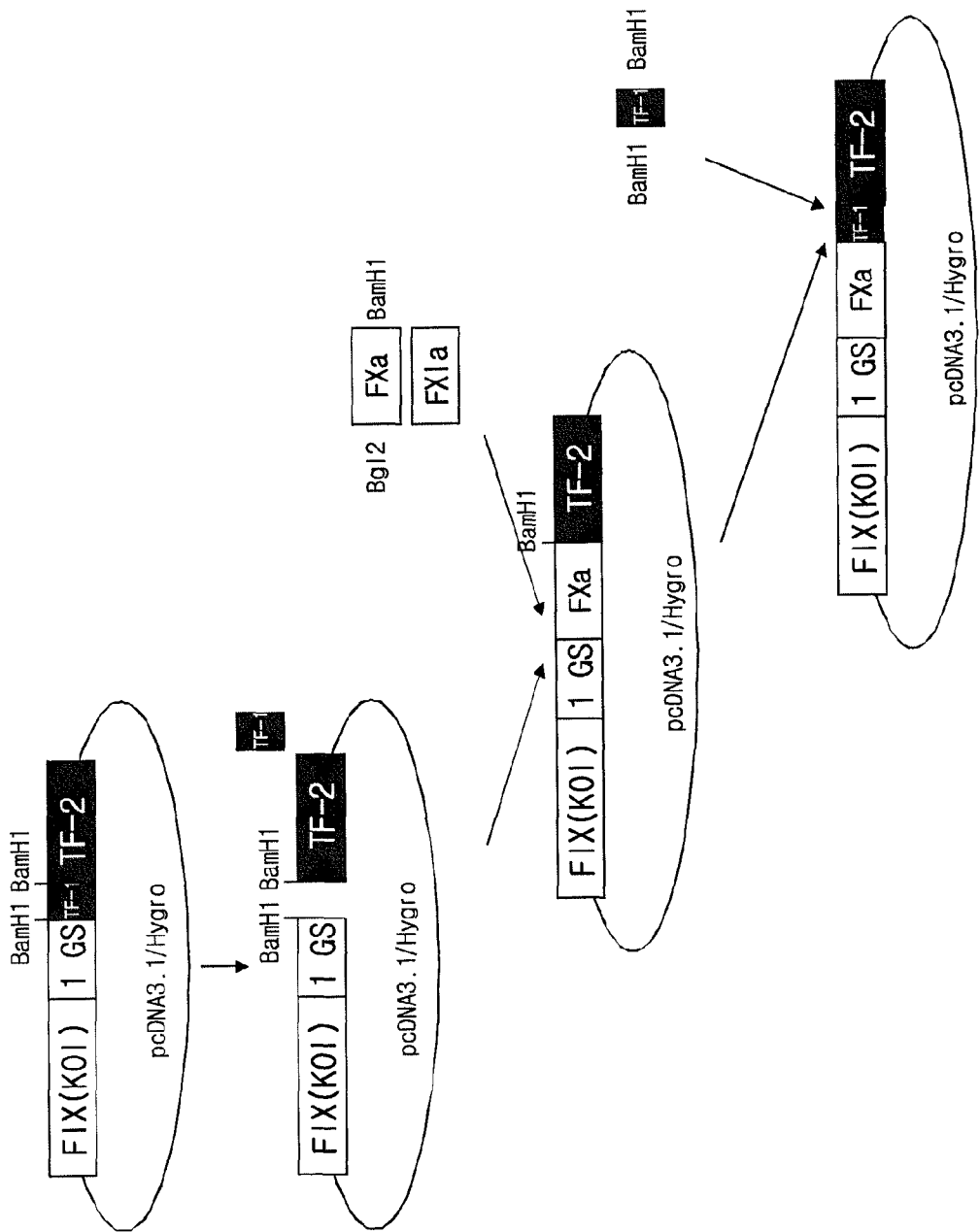
FIG. 5: a schematic view illustrating the process of constructing FIX(KOI)-GS1-FXa-Tf and FIX(KOI)-GS1-FXIa-Tf expression vectors.

A FIX(KOI)-Tf expression vector containing a GS1 linker and an FXa cleavage site (FXa) was constructed as illustrated in FIG. 5.

Specifically, two complementary sequences Oa (SEQ ID NO: 56) and Ob (SEQ ID NO: 57) (each 100 pmol in 5 μL), which constitute the FXa cleavage site, were annealed at 72° C. for 10 min, and treated with BglII and BamHI at 37° C. for 30 min. Meanwhile, the FIX(KOI)-GS1-Tf expression vector prepared in Example <3-1> was treated with BamHI to delete the Tf fragment linked to GS1 (hereinafter, referred to as "Tf-1") therefrom, followed by ligation with the FXa cleavage site using T4 DNA ligase (Takara, #2011A). After confirming that the FXa cleavage site was cloned in the forward direction, the fragment Tf-1, previously removed by BamHI digestion, was re-ligated to the vector at the BamHI site using T4 DNA ligase (Takara, #2011A).

<5-2> Construction of FIX(KOI)-GS7-FXa-GS7-Tf Expression Vector (pcDNA3.1-hygro-FIX(KOI)-G57-FXa-G57-Tf)

A FIX(KOI)-Tf expression vector containing two GS7 linkers with an FXa cleavage site located therebetween was constructed as illustrated in FIG. 4.

Specifically, a GS7-FXa-GS7-subcloned vector was treated with AgeI at 37° C. to obtain a GS7-FXa-GS7 fragment while the FIX(KOI)-Tf expression vector prepared in Example 2 was digested with the same restriction enzyme, followed by ligation using T4 DNA ligase to afford a FIX(KOI)-G57-FXa-G57-Tf expression vector.

The GS7-FXa-GS7-subcloned vector was prepared as follows. Primers Oa (SEQ ID NO: 56) and Ob (SEQ ID NO: 57) were synthesized to contain the amino acid sequence IEGR, a cleavage recognition site for FXa. These synthesized primers (each 5 μL, 100 pmole/μL) were heated at 72° C. for 10 min and cooled, followed by annealing. This linker was ligated to a 7GS-cloned pcDNA3.1/Hygro vector (SK Chemical) which had been sequentially treated with the restriction enzymes BamHI and HpaI, using T4 DNA ligase. The resulting vector was digested with BamHI and HpaI while an insert containing 7GS and Tf was treated with BglII and HpaI, followed by ligation using T4 DNA ligase. The insert was prepared by PCR which was performed on the 7GS-cloned pcDNA3.1/Hygro vector using F16 (SEQ ID NO: 51) and R13 (SEQ ID NO: 50) in the presence of Phusion® High-Fidelity DNA polymerase (Finnzyme, 2 units/μL, #F-530S), with 30 cycles of annealing at 58° C. and extension at 68° C. for 2 min. The PCR product was treated with BglII and HpaI, and purified by gel extraction.

Example 6

Construction of FIX(KOI)-Tf Expression Vector Containing GS Linker with FXIa Cleavage Site <6-1> Construction of FIX(KOI)-GS1-FXIa-Tf expression vector (pcDNA3.1-hygro-FIX(KOI)-GS1-FXIa-Tf)

A FIX(KOI)-Tf expression vector containing a GS1 linker and an FXIa cleavage site (FXIa) was constructed as illustrated in FIG. 5.

Specifically, two complementary sequences Oc (SEQ ID NO: 58) and Od (SEQ ID NO: 59) (each 100 pmol in 5 μL), which constituted the FXIa cleavage site, were reacted at 72° C. for 10 min for annealing, and then treated with BamHI at 37° C. for 30 min. Meanwhile, the FIX(KOI)-GS1-Tf expression vector prepared in Example <3-1> was treated with BamHI to delete the Tf fragment (Tf-1) linked to GS1. The cleavage recognition site for FXIa was ligated to the expression vector using T4 DNA ligase (Takara, #2011A). After the FXIa cleavage site was cloned in the forward direction, the recombinant vector was digested with the restriction enzyme BamHI, and ligated with the fragment Tf-1 at the BamHI site in the presence of T4 DNA ligase (Takara, #2011A).

<6-2> Construction of FIX(KOI)-G57-FXIa-G57-Tf Expression Vector (pcDNA3.1-hygro-FIX(KOI)-G57-FXIa-G57-Tf)

A FIX(KOI)-Tf expression vector containing two GS7 linkers with an FXIa cleavage site located therebetween was constructed as illustrated in FIG. 4.

Specifically, a GS7-FXIa-GS7-subcloned vector was treated with AgeI at 37° C. to obtain a GS7-FXIa-GS7 fragment while the FIX(KOI)-Tf expression vector prepared in Example 2 was digested with the same restriction enzyme, followed by ligation using T4 DNA ligase to afford a FIX(KOI)-GS7-FXIa-GS7-Tf expression vector. The GS7-FXIa-GS7-cloned vector was prepared in the same manner as in Example 5-2 for the FIX(KOI)-GS7-FXa-GS7-Tf expression vector, with the exception of using primers Oc (SEQ ID NO: 58) and Od (SEQ ID NO: 59) designed to have the amino acid sequence of SKLTRAETVF, a cleavage recognition site for FXIa.

Comparative Example 1

Construction of FIX(KOI)-G6V-Albumin Expression Vector (pcDNA3.1-Hygro-FIX(KOI)-G6V-Albumin)

Figure 6:
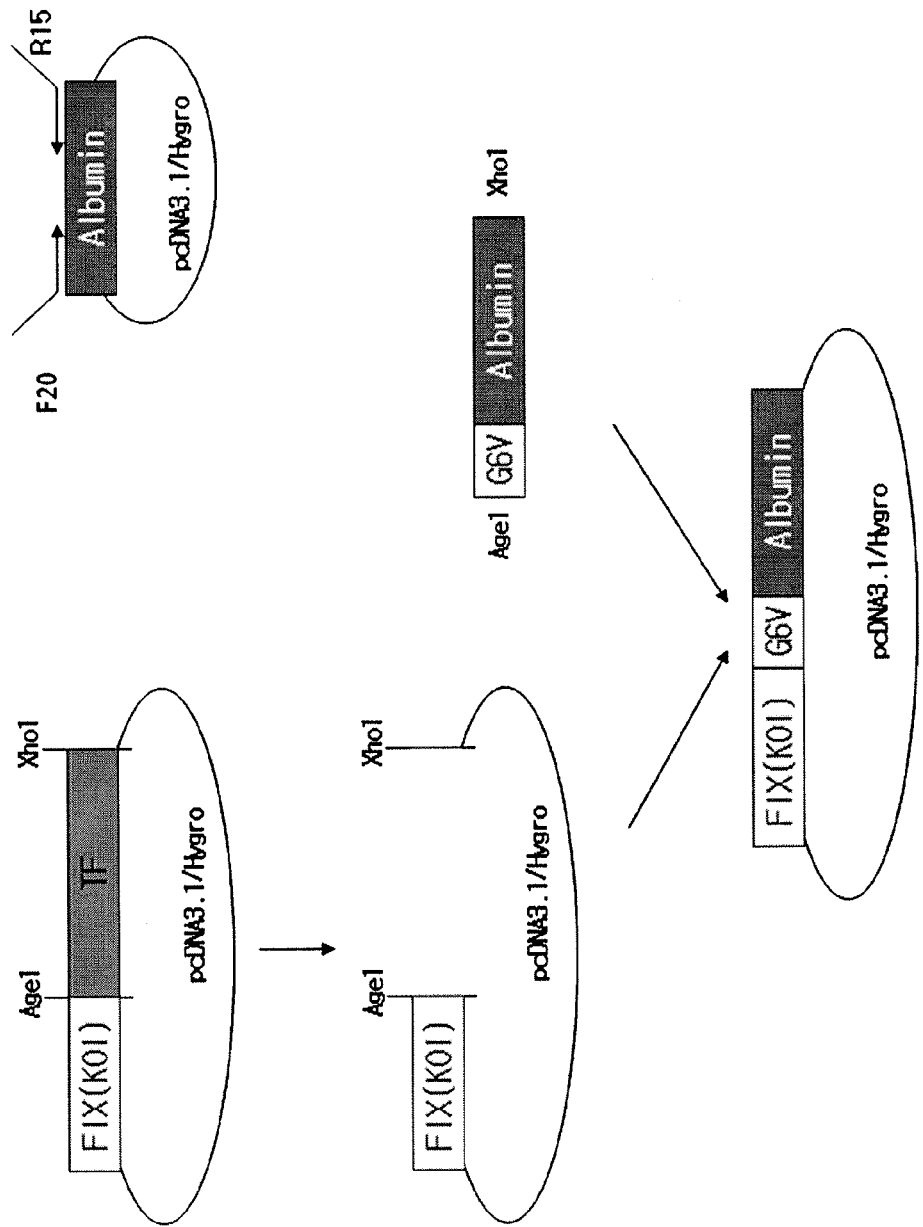
FIG. 6: a schematic view illustrating the process of constructing a FIX(KOI)-G6V-Albumin expression vector.

The FIX(KOI)-G6V-albumin fusion protein disclosed in U. S. Patent Publication No. 20090042787 A1 was prepared according to the procedure illustrated in FIG. 6. First, human albumin cDNA was obtained by RT-PCR using human hepatic mRNA (Clontech) as a template with gene-specific primers F20 and R15 (SEQ ID NOS: 60 and 61). This RT-PCR was carried out by reacting 10 μL of a reverse transcription reacting solution (1 μL 10× reverse transcriptase buffer, 0.6 μL oligo-dT primer, 1 μL dNTP, 0.4 μL water, and 5 μL human hepatic mRNA (10 ng/μL)) at 65° C. for 5 min, at room temperature for 5 min, followed by adding 1 μL 100 mM DTT and 1 μL of a reverse transcriptase buffer and reacting the solution at 42° C. for 1 hr. The sequence of DNA encoding of the human albumin was obtained from the synthesized cDNA as a template using primers F20 and R15. The PCR was carried out by reacting 50 μL of reacting solution (1 μL cDNA, 10 μL 5× Phusion® HF Buffer, primers F20 and R15, each 1 μL, 1 μL 10 mM dNTP, 0.5 μL Phusion® DNA polymerase (FINNZYMES, #F-530S 2 units/μL), and 35.5 μL water) 98° C. for 1 min, and subjected to 30 cycles of 98° C. for 10 sec, 62° C. at 30 sec, and 72° C. for 60 sec, followed by a final thermal treatment at 72° C. for 7 min to terminate the reaction. Separately, the amino acid sequence of the GS linker G6V (GGGGGGV) (SEQ ID NO: 64) disclosed in U. S. Patent Publication No. 20090042787 A1, was prepared by PCR using primer F21 (SEQ ID NO: 62) and primer R16 (SEQ ID NO: 63) for covering the entire sequence of albumin with the obtained albumin serving as a template. PCR was conducted under the conditions of 30 cycles of annealing at 58° C. and extension at 68° C. for 2 min in the presence of Phusion® High-Fidelity DNA polymerase (Finnzyme, 2 units/μL, #F-530S). The PCR product was digested with AgeI and XhoI while the FIX(KOI)-AgeI-TF of Example 2 was treated with AgeI and XhoI, followed by ligation using T4 DNA ligase (Takara, #2011A).

Properties of the expression vectors constructed in the Examples and Comparative Example are summarized in Table 2, below.

Experimental Example 1

Transfection and Expression of Fusion Protein

<1-1> Transfection of Fusion Protein

The FIX(KOI)-Tf expression vectors of Examples 2 to 6 and the FIX(KOI)-G6V-Albumin expression vector of Comparative Example 1 were transfected into CHO-DG44 (VK2) cells, a CHO cell line stably expressing VKORC1 (vitamin K epoxide reductase complex subunit 1) to express the FIX(KOI) fusion protein. CHO-DG44 (VK2) was prepared in-house, by introducing a VKORC1 expression vector into CHO-DG44 cells that were purchased from Invitrogen.

Specifically, the expression vectors synthesized in Examples 2 to 5 and Comparative Example 1 were amplified in *E. coli* (HIT competent cell, DH5α, #RH617), and extracted with the aid of an endotoxin free maxi prep kit (QIAGEN, cat #12362). For expression control, the pcDNA3.1/hygro vector and the pcDNA3.1-hygro-FIX (KOI) vector constructed in Example 1 were employed.

For use in transfection with the vectors, animal cells were prepared as follows. CHO-DG44(VK2) cells were grown for 48 hrs in α-MEM (Lonza, #12-169F) supplemented with 10% FBS (Lonza, #14-501F), 1×HT (Invitrogen, #11067-030), 4 mM L-glutamine (Lonza, #17-605E) and 200 μg/ml hygromycin (Invitrogen, #10687-010), and the medium was centrifuged to remove suspension cells. The cells thus obtained were seeded at a density of $1.5 \times 10^6$ cells/well into 6-well plates. The cells were incubated for 24 hrs in the same medium and transfected using Lipofectamine 2000 (Invitrogen, Cat no. 11668-019) according to the manufacturer's instruction. The transfection DNA was FIX(KOI)-derived DNA 3 μg: β-galactosidase DNA 1 μg per well. Four hours after transfection, the culture medium was replaced by a serum-free medium (OptiMEM) and supplemented with 5

TABLE 2

| Ex. No. | FIX(KOI) Fusion Protein | Linker Sequence | SEQ ID NO: | No. of A.A. in Linker |
|---|---|---|---|---|
| 2 | FIX(KOI)-Tf | G | — | 1 |
| <3-1> | FIX(KOI)-GS1-Tf | GGGGS | 3 | 5 |
| <3-2> | FIX(KOI)-GS15-Tf | (GGGGS)$_{15}$ TG | 4 | 77 |
| <4-1> | FIX(KOI)-GS1-THR-GS1-Tf | GGGGS-LVPRGS-GGGS TG | 5 | 17 |
| <4-2> | FIX(KOI)-GS7-THR-GS7-Tf | (GGGGS)$_7$-LVPRGS-(GGGGS)$_7$TG | 6 | 78 |
| <4-3> | FIX(KOI)-GS1-THR-GS1-del-Tf | GGGGS-LVPRGS-GGGS | 7 | 15 |
| <5-1> | FIX(KOI)-GS1-FXa-Tf | GGGGS-IEGR | 8 | 9 |
| <5-2> | FIX(KOI)-GS7-FXa-GS7-Tf | (GGGGS)$_7$-IEGR-(GGGGS)$_7$ TG | 9 | 76 |
| <6-1> | FIX(KOI)-GS1-FXIa-Tf | GGGGS-SKLTRAETVF | 10 | 15 |
| <6-2> | FIX(KOI)-GS7-FXIa-GS7-Tf | (GGGGS)$_7$-SKLTRAETVF-(GGGGS)$_7$ TG | 11 | 82 |
| C. Ex. 1 | FIX(KOI)-G6V-Albumin | GGGGGGV | 64 | 7 |

µg/ml vitamin K thereto. The transfected cells were cultured for 48 hrs after which the cell medium was sampled and stored at −70° C.

<1-2> Analysis of Expression Pattern by Western Blot

Proteins of the samples obtained in Experimental Example <1-1> were quantified by the Bradford assay, and a 4×LDS sample buffer (Invitrogen #NP0008) and a 7× protease inhibitor cocktail (Roche, Complete Mini, EDTA-free, #1 836 170) were used to adjust a total protein concentration of 1 µg/µL for each sample. 10 µL of the samples were loaded into a 4-12% gel (Invitrogen, NuPAGE® Novex 4-12% Bis-Tris Gel), and subjected to a gel electrophoresis. The gel obtained from the electrophoresis was transferred onto a nitrocellulose membrane (Whatman, PROTRAN #BA83) which was then placed in an omnitray and blocked with a blocking solution (3% BSA in TBS with 0.1% Tween 20) for 1 hr in a rocker. Thereafter, the membrane was incubated with a primary antibody (Cedarlane #CL20040AP) was treated to the membrane at 4° C. for 12 hrs and then with a secondary antibody (anti goat, Santa Cruz #SC-2350) at room temperature for 1 hr before exposure to a film using an ECL solution mix of Amersham (GE Healthcare, #RPN1232).

Figure 7:
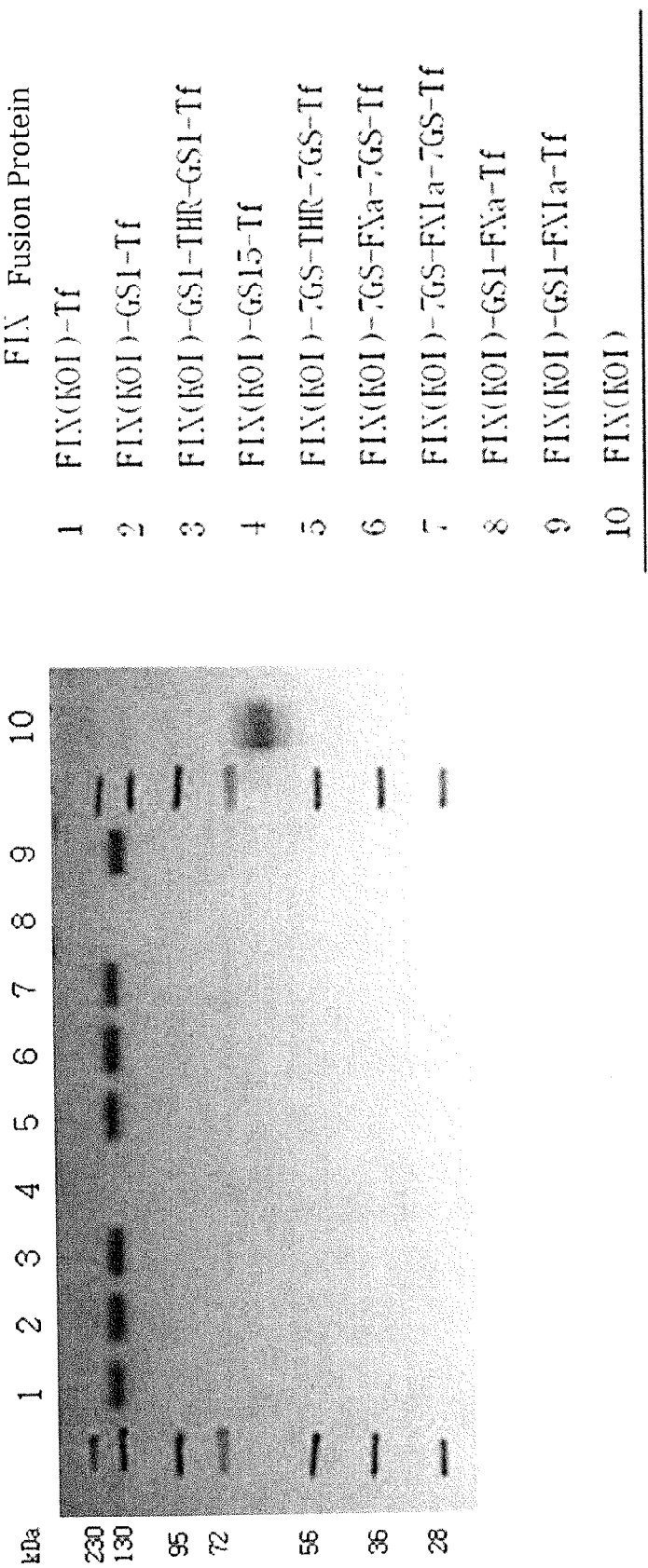
FIG. 7: Western blots of FIX(KOI)-Tf (free of linkers), FIX(KOI)-GS1-Tf, FIX(KOI)-GS1-THR-GS1-Tf, FIX (KOI)-GS15-Tf, FIX(KOI)-GS7-THR-GS7-Tf, FIX(KOI)-GS7-FXa-GS7-Tf, FIX(KOI)-GS7-FXIa-GS7-Tf, FIX (KOI)-GS1-FXa-Tf, FIX(KOI)-GS1-FXIa-Tf, and FIX (KOI) expression vectors.

Western blots are given in FIG. 7. As can be seen in FIG. 7, the FIX(KOI) fusion protein of the present invention was not fragmented, but was found to have the predicted size.

Experimental Example 2

Assay for Specific Activity of FIX(KOI) Fusion Protein

<2-1> Specific Activity of FIX(KOI) Fusion Protein Derivative Family (FIX(KOI)-Tf, FIX(KOI)-GS1-Tf, FIX(KOI)-GS1-THR-GS1-Tf, FIX(KOI)-GS15-Tf, FIX(KOI)-G57-THR-G57-Tf, FIX(KOI)-GS7-FXa-GS7-Tf, FIX(KOI)-G57-FXIa-GS7-Tf, FIX(KOI)-GS1-FXa-Tf, FIX(KOI)-GS1-FXIa-Tf, FIX(KOI)-G6V-Alb), and Native FIX(KOI)

The FIX(KOI) fusion protein samples of Experimental Example 1 and the wild-type FIX(KOI) were assayed for specific activity. Specifically, the samples were measured for FIX protein (antigen) level using a FIX ELISA kit (Cedarlane, Paired Antibodies for Elisa-Factor IX, CL20041K, Lot EIA9-0025R1) and analyzed for the chromogenic activity of FIX using a BIOPHEN Factor 1× assay kit (HYPEN BioMed, Ref. 221802) to determine the clotting activity. Standard human plasma (Dade Behring, REF ORKL13, Lot 503214E) was used as a control for both the analyses. The standard human plasma was serially diluted from 1/100 (100%) to 1/3200 (3.13%) by ½. On the basis of the OD values of the standard, the antibody titers of the samples were calculated. The culture medium for the FIX(KOI) fusion protein was diluted ¼.

Although the quantity of the proteins (antigen) was measured by ELISA, since some of them might lack FIX activity, specific activity (activity to antigen ratio) was obtained by dividing the value obtained from chromogenic activity assay the value obtained from with ELISA.

Figure 8A:
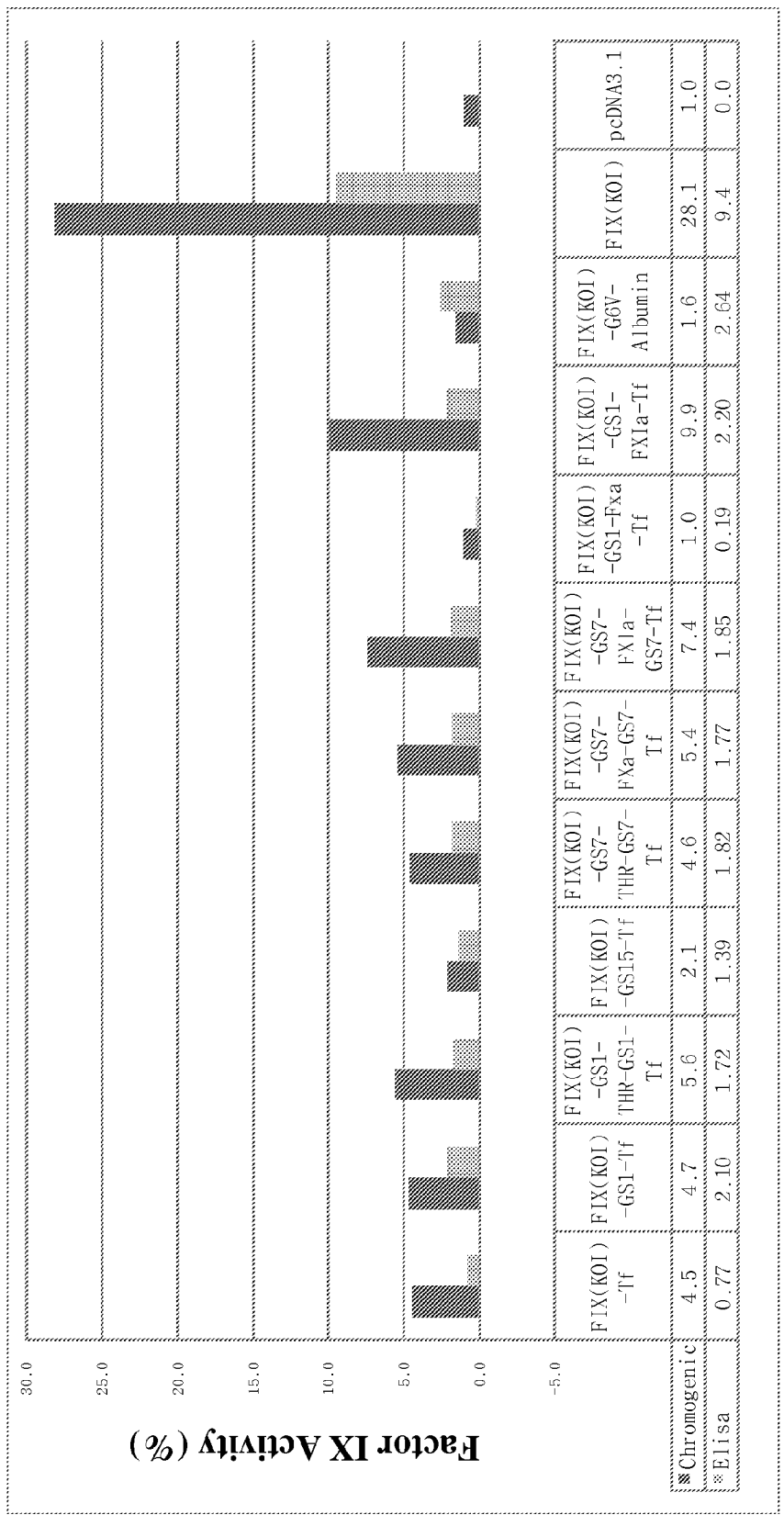
FIG. 8a: a graph showing FIX activities of the fusion proteins expressed from FIX(KOI)-Tf (free of linkers), FIX(KOI)-GS1-Tf, FIX(KOI)-GS1-THR-GS1-Tf, FIX (KOI)-GS15-Tf, FIX(KOI)-GS7-THR-GS7-Tf, FIX(KOI)-GS7-FXa-GS7-Tf, FIX(KOI)-GS7-FXIa-GS7-Tf, FIX (KOI)-GS1-FXa-Tf, FIX(KOI)-GS1-FXIa-Tf, FIX(KOI)-G6V-Albumin, FIX(KOI), and pcDNA3.1/hygro expression vectors, as analyzed by ELISA and chromogenic activity assay.

ELISA and chromogenic assay results of the samples obtained in Examples are summarized and depicted in Table 3 and FIG. 8a, respectively. The specific activity obtained on the basis of the results is given in Table 3 and FIG. 8b.

TABLE 3

| FIX(KOI) Fusion Protein | Activity (%) | Antigen (%) | Specific Activity (Activity/Ag) |
|---|---|---|---|
| FIX(KOI)-Tf | 4.49 | 0.77 | 5.86 |
| FIX(KOI)-GS1-Tf | 4.67 | 2.10 | 2.23 |
| FIX(KOI)-GS15-Tf | 2.14 | 1.39 | 1.53 |
| FIX(KOI)-GS1-THR-GS1-Tf | 5.57 | 1.72 | 3.24 |
| FIX(KOI)-GS7-THR-GS7-Tf | 4.59 | 1.82 | 2.53 |
| FIX(KOI)-GS1-FXa-Tf | 1.04 | 0.19 | 5.58 |
| FIX(KOI)-GS7-FXa-GS7-Tf | 5.44 | 1.77 | 3.07 |
| FIX(KOI)-GS1-FXIa-Tf | 9.94 | 2.20 | 4.52 |
| FIX(KOI)-GS7-FXIa-GS7-Tf | 7.40 | 1.85 | 4.00 |
| FIX(KOI)-G6V-Albumin | 1.62 | 2.64 | 0.61 |
| FIX(KOI) | 28.13 | 9.45 | 2.98 |
| pcDNA3.1 | 1.00 | −0.03 | 0.00 |

Figure 8B:
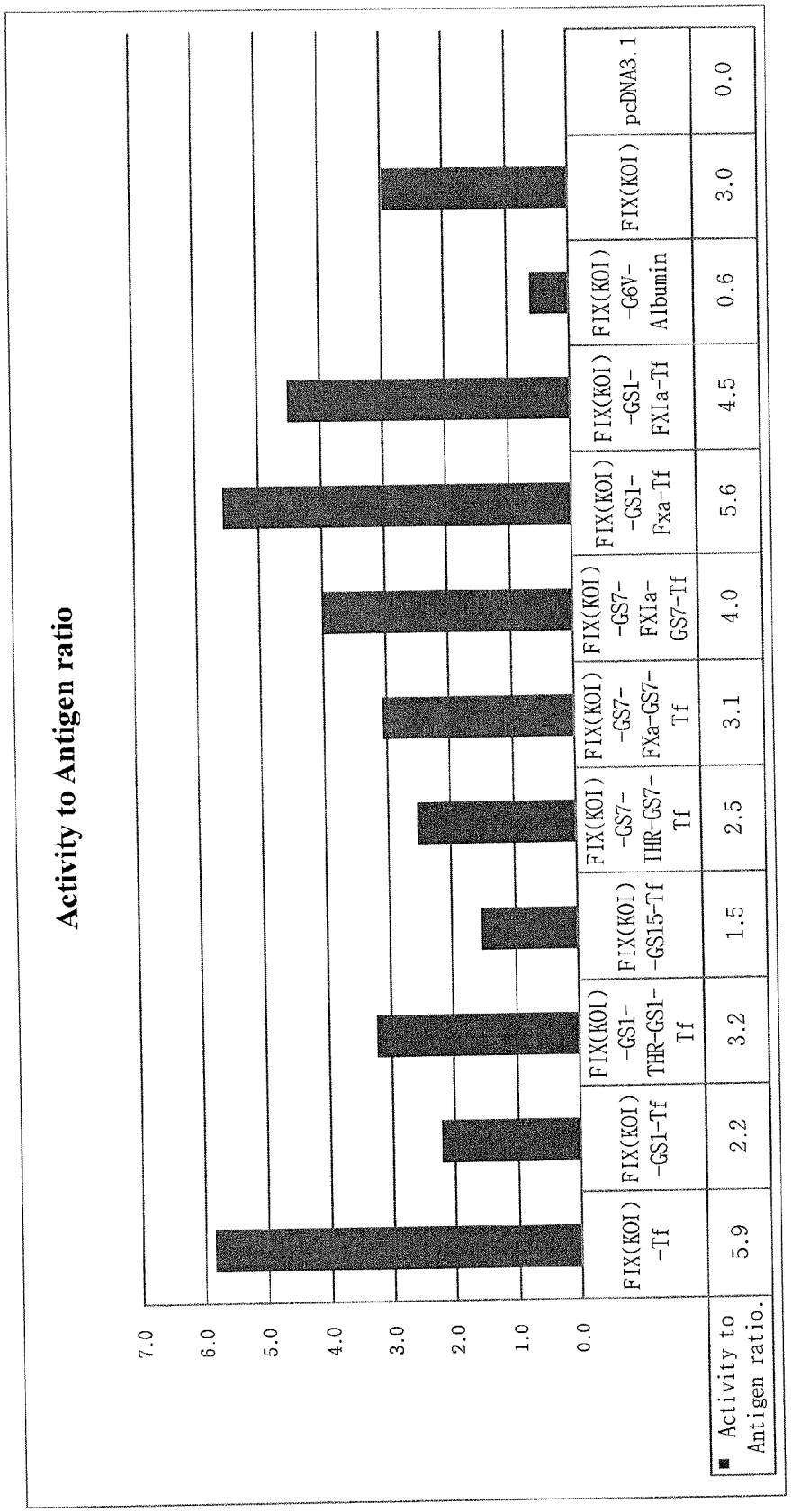

As can be seen in Table 3 and FIG. 8b, the specific activity of FIX(KOI)-transferrin fusion protein was 5.86 which was remarkably increased, compared to that of wild-type FIX (KOI)'s specific activity of 2.98. In addition, the FIX(KOI)-transferrin fusion proteins containing linkers were observed to range in specific activity from 1.53 to 5.58, which was also higher than that of the FIX(KOI)-G6V-Albumin fusion protein.

<2-2> Specific Activity of FIX(KOI) Fusion Protein Derivatives (FIX(KOI)-GS1-THR-GS1-Tf, FIX(KOI)-GS1-THR-GS1-del-Tf), and Wild-Type FIX(KOI)

The fusion proteins FIX(KOI)-GS1-THR-GS1-Tf and FIX(KOI)-GS1-THR-GS1-del-Tf of Experimental Example 1 and the FIX(KOI) fusion protein of the wild-type FIX (KOI) were assayed for specific activity. The samples of Examples <4-1> and <4-3>, the linkers of which were almost identical in amino acid sequence, were measured for FIX protein (antigen) level using a FIX ELISA kit (Cedarlane, Paired Antibodies for Elisa-Factor IX, CL20041K, Lot EIA9-0028R1) and analyzed for the chromogenic activity of FIX using a BIOPHEN Factor 1× assay kit (HYPEN BioMed, Ref. 221802, Lot 01602) to determine clotting activity. Standard human plasma (Dade Behring, REF ORKL13, Lot 503216F) was used as a control for both the analyses, and was diluted in the same manner as in Example <2-1>.

Figure 8C:
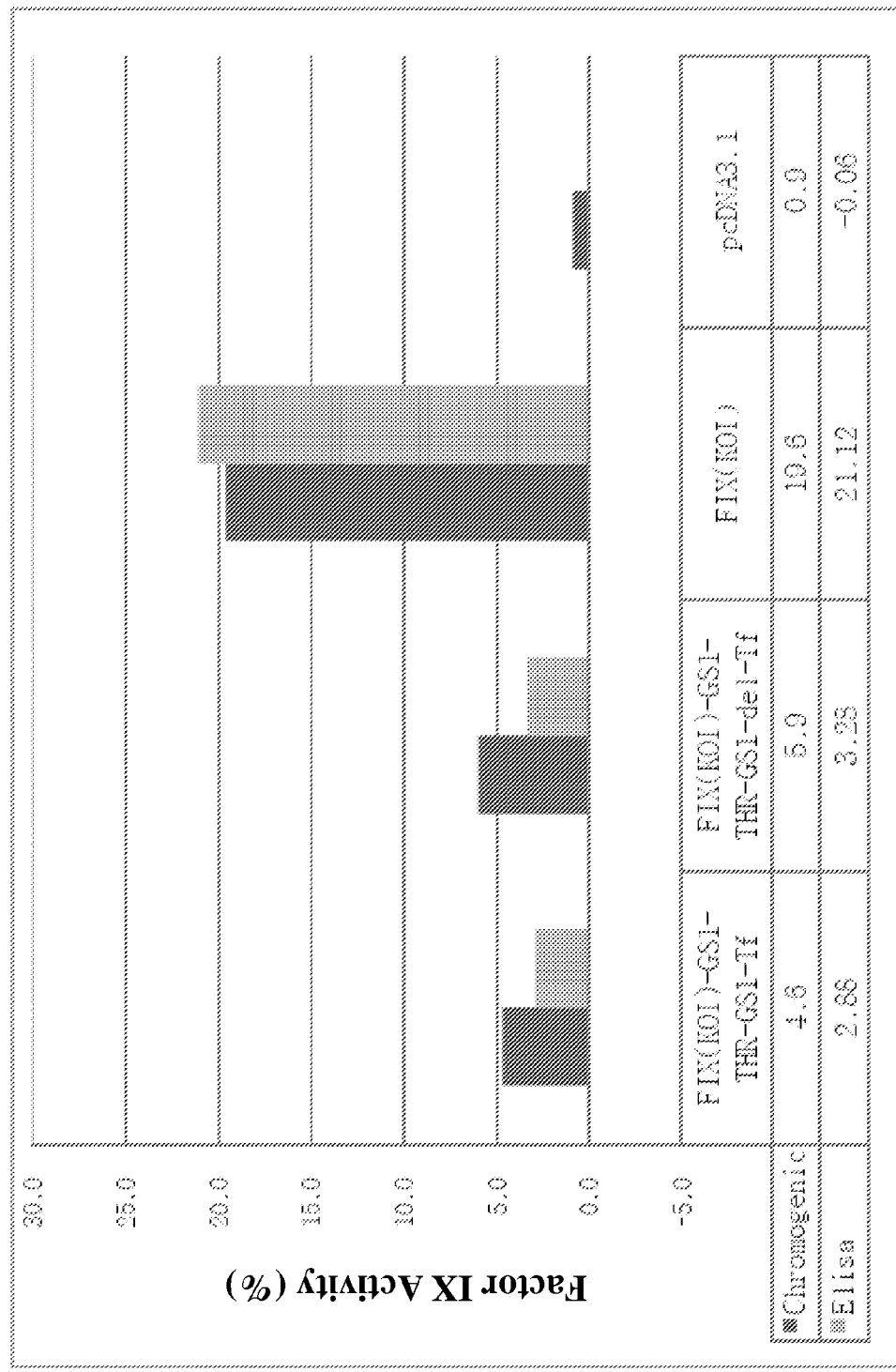
FIG. 8c: a graph showing FIX activities of the fusion proteins expressed from FIX(KOI)-GS1-THR-GS1-Tf, FIX (KOI)-GS1-THR-GS1-del-Tf, FIX(KOI) and pcDNA3.1/hygro expression vectors, as measured by ELISA and chromogenic activity assay.

ELISA and chromogenic activity results of samples of Examples <4-1> and <4-3> are shown in Table 4 and FIG. 8c, and the specific activity based on the results are summarized in Table 4 and FIG. 8d.

TABLE 4

| FIX(KOI) Fusion Protein | Activity (%) | Antigen (%) | Specific Activity (Activity/Ag) |
|---|---|---|---|
| FIX(KOI)-GS1-THR-GS1-Tf | 4.6 | 2.88 | 1.6 |
| FIX(KOI)-GS1-THR-GS1-del-Tf | 5.9 | 3.28 | 1.8 |
| FIX(KOI) | 19.6 | 21.12 | 0.9 |
| pcDNA3.1 | 0.9 | −0.06 | −14.8 |

As can be seen in Table 4 and FIG. 8d, the specific activity of the fusion proteins containing FIX(KOI)-transferrin linkers were found to be in the range of from 1.6 to 1.8, which was increased compared to the wild-type FIX(KOI)'s specific activity of 0.9. In addition, FIX(KOI)-GS1-THR-GS1-TF and FIX(KOI)-GS1-THR-GS1-del-Tf fusion proteins, which contained and lacked an AgeI restriction site, respectively, were found to be similar in specific activity.

In this experimental example, a constant relationship was found neither between the length of the linkers and the specific activity of the FIX(KOI) fusion proteins nor between the cleavage site type of the linker and the specific activity.

What is claimed is:

1. A fusion protein comprising human-derived factor IX (FIX) and human-derived transferrin,
    wherein the fusion protein comprises a linker between the FIX and the transferrin, said linker being the amino acid sequence of SEQ ID NO: 9 or 11;
    wherein the FIX amino acid sequence has 95% or higher identity to the amino acid sequence of SEQ ID NO: 1; and
    wherein the transferrin amino acid sequence has 95% or higher identity to the amino acid sequence of SEQ ID NO: 2.

2. A gene encoding the fusion protein of claim 1.

3. The gene of claim 2, wherein the gene has the nucleotide sequence of SEQ NO: 20 or 21.

4. A recombinant vector comprising the gene of claim 3.

5. An isolated host cell comprising the recombinant vector of claim 4 therein.

6. The host cell of claim 5, wherein the host cell is selected from the group consisting of a CHO cell, a BHK-21 cell, an HEK293 cell, and a HepG2 cell.

* * * * *